(12) United States Patent
Shahaf et al.

(10) Patent No.: US 10,549,052 B2
(45) Date of Patent: Feb. 4, 2020

(54) NASAL DELIVERY DEVICE

(71) Applicant: SIPNOSE LTD., Yokne'am Ilit (IL)

(72) Inventors: Daniel Shahaf, M.P. Emek Ha-Yarden (IL); Iris Shichor, Zichron Yaakov (IL); Yehuda Poran, Kibbutz el-rom (IL); Iftah Poran, Kibbutz el-rom (IL)

(73) Assignee: SIPNOSE LTD., Yokne'am Ilit (IL)

( * ) Notice: Subject to any disclaimer, the term of this patent is extended or adjusted under 35 U.S.C. 154(b) by 1201 days.

(21) Appl. No.: 14/381,241

(22) PCT Filed: Feb. 28, 2013

(86) PCT No.: PCT/IL2013/050171
§ 371 (c)(1),
(2) Date: Aug. 27, 2014

(87) PCT Pub. No.: WO2013/128447
PCT Pub. Date: Sep. 6, 2013

(65) Prior Publication Data
US 2015/0297845 A1    Oct. 22, 2015

Related U.S. Application Data

(60) Provisional application No. 61/603,966, filed on Feb. 28, 2012, provisional application No. 61/603,967, (Continued)

(51) Int. Cl.
*A61M 15/08* (2006.01)
*A61M 15/00* (2006.01)

(52) U.S. Cl.
CPC .......... *A61M 15/08* (2013.01); *A61M 15/009* (2013.01); *A61M 15/0021* (2014.02); *A61M 15/0035* (2014.02); *A61M 2202/064* (2013.01)

(58) Field of Classification Search
CPC .............. A61M 11/02; A61M 15/0096; A61M 2205/3306; A61M 2205/7545;
(Continued)

(56) References Cited

U.S. PATENT DOCUMENTS 5,318,015 A * 6/1994 Mansson ........... A61M 15/0065
128/200.21
5,460,173 A    10/1995 Mulhauser et al.
(Continued)

FOREIGN PATENT DOCUMENTS

WO    2006108558 A1    10/2006
WO    2007143993 A2    12/2007

OTHER PUBLICATIONS

International Search Report and Written Opinion dated Jul. 9, 2013 in corresponding International Application No. PCT/IL2013/050171.

*Primary Examiner* — Bradley H Philips
*Assistant Examiner* — Victoria Murphy

(57) ABSTRACT

The present invention provides a two-step mechanism for delivering a flowable substance to the nasal passages, comprising: a. a nosepiece adapted to be in fluid connection with said nasal passages; b. at least one air-tight enclosure, comprising predetermined amount of compressed gas in the same; said compressed gas is pressurized to predetermined amount of pressure; c. a charging mechanism, fluidly connected with said air-tight enclosure, characterized by at least two configurations: a retracted position and an extended position; where, when said charging mechanism is transformed from said extended position to said retracted position, said charging mechanism is adapted to enable delivery of said pressurized and predetermined amount of compressed gas from at least one first predetermined position in said air-tight enclosure to at least one second predetermined position; d. an activation mechanism, adapted to entrain said
(Continued)

flowable substance within said pressurized and predetermined amount of compressed gas.

13 Claims, 39 Drawing Sheets

Related U.S. Application Data filed on Feb. 28, 2012, provisional application No. 61/707,969, filed on Sep. 30, 2012, provisional application No. 61/728,818, filed on Nov. 21, 2012.

(58) Field of Classification Search
CPC ...... A61M 2205/7509; A61M 2206/14; A61M 2205/583; A61M 2205/581; A61M 2205/3375; A61M 15/08; A61M 15/0093; A61M 15/009; A61M 15/0021; A61M 15/0035; A61M 15/0028; A61M 15/0091
See application file for complete search history.

(56) References Cited

U.S. PATENT DOCUMENTS

| | | | |
|---|---|---|---|
| 6,526,966 B1* | 3/2003 | Peesay | A61J 9/00 128/200.14 |
| 6,779,520 B2 | 8/2004 | Genova et al. | |
| 7,114,496 B1 | 10/2006 | Resnick et al. | |
| 7,722,566 B2 | 5/2010 | Tsutsui | |
| 7,740,014 B2* | 6/2010 | Djupesland | A61B 5/085 128/203.18 |
| 7,806,117 B2 | 10/2010 | Tsutsui | |
| 2002/0056449 A1 | 5/2002 | Wakefield et al. | |
| 2002/0189612 A1 | 12/2002 | Rand | |
| 2003/0005926 A1 | 1/2003 | Jones et al. | |
| 2004/0112378 A1* | 6/2004 | Djupesland | A61B 5/085 128/203.12 |
| 2004/0177849 A1 | 9/2004 | Del Bon | |
| 2008/0092885 A1 | 4/2008 | Von Schuckmann | |
| 2008/0264415 A1* | 10/2008 | Eason | A61M 15/0028 128/203.15 |
| 2009/0064997 A1 | 3/2009 | Li | |
| 2010/0234922 A1 | 9/2010 | Forsell | |

\* cited by examiner

Prior Art

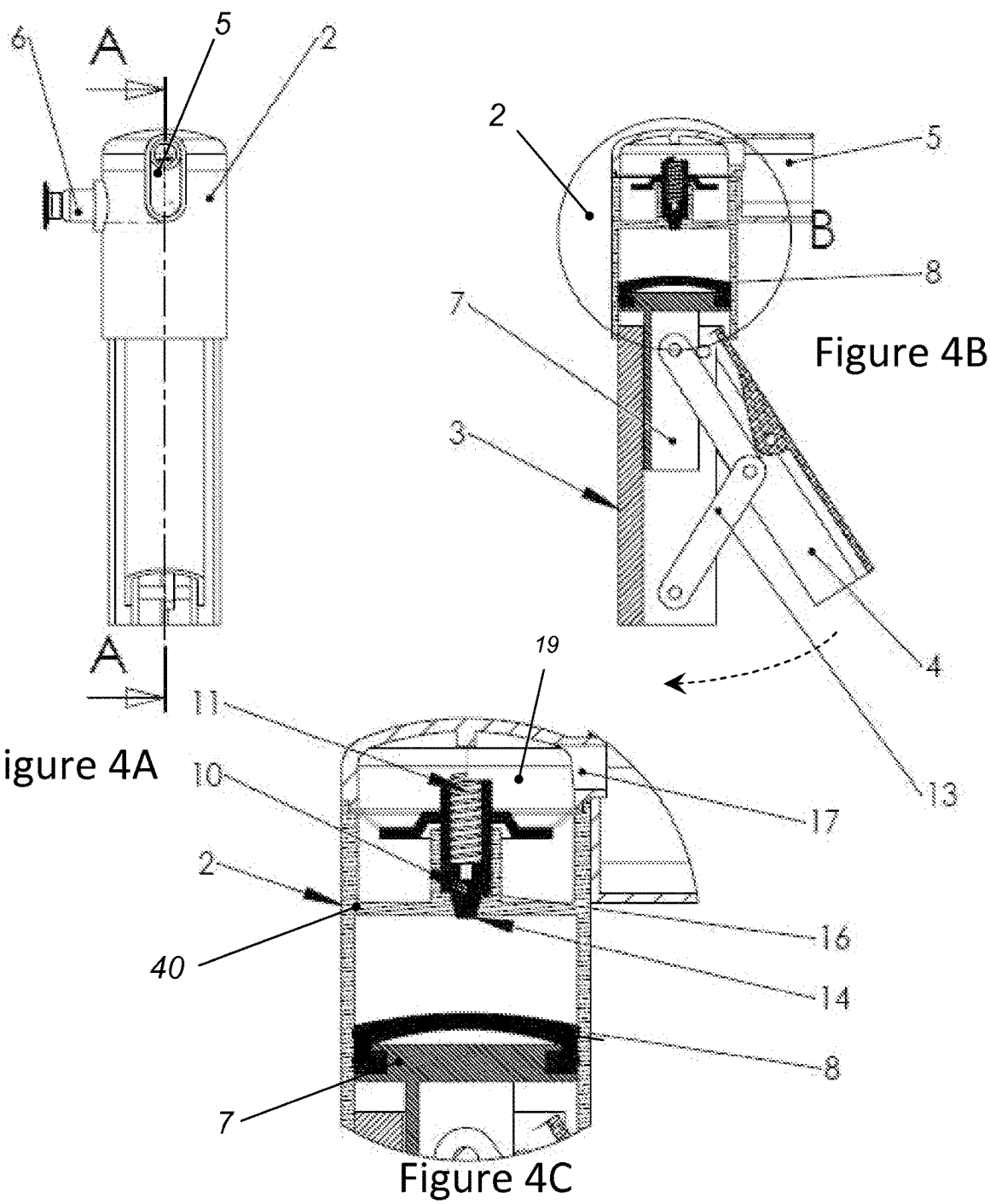

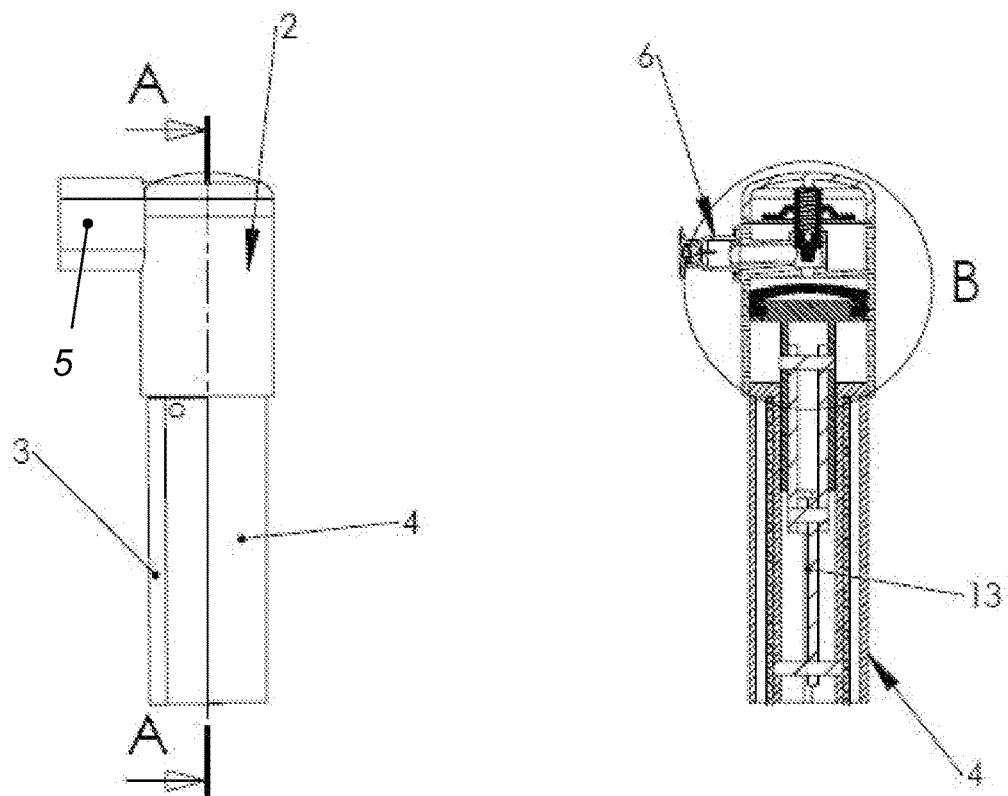
Figure 5A
Figure 5B
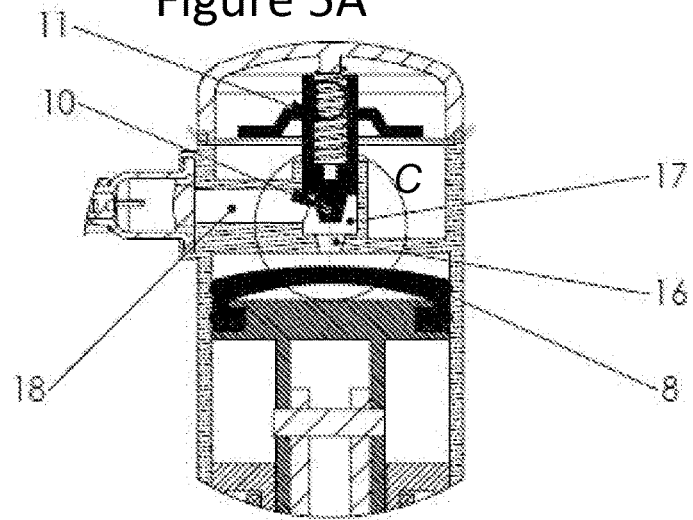
Figure 5C
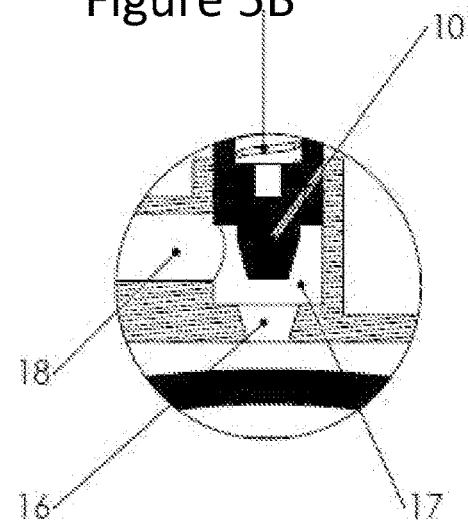
Figure 5D

SECTION A-A

Figure 10

Distance of aerosol distribution

Delivery of Powders (Glass Maze Model)

% of Total MB

SipNose    DirectHaler/    SNBL    APTAR
           Optinose

FIGURE 22

| Applicator | Type of Solution | Average Diameter (μm) |
|---|---|---|
| Minrin | Saline | 47.3 |
| Minrin | Minrin | 73.7 |
| Wolf Tory MAD 300 | Saline | 114 |
| Wolf Tory MAD 300 | Saline | 94.8 |
| Wolf Tory MAD 300 | Saline | 254 |
| Present Device | Saline | 75.8 |
| Present Device | Saline | 71.3 |

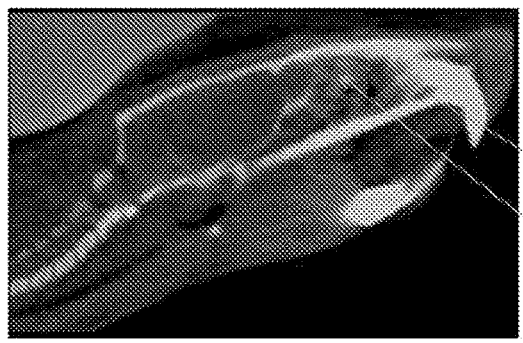 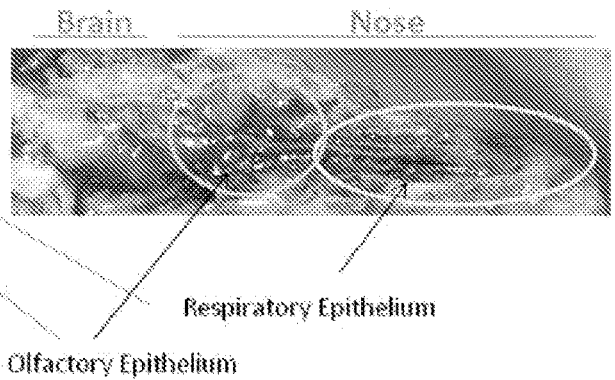
Figure 31A                    Figure 31B
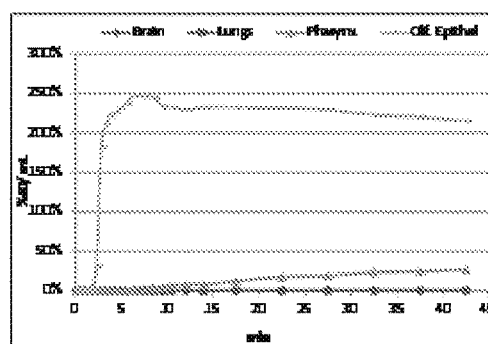 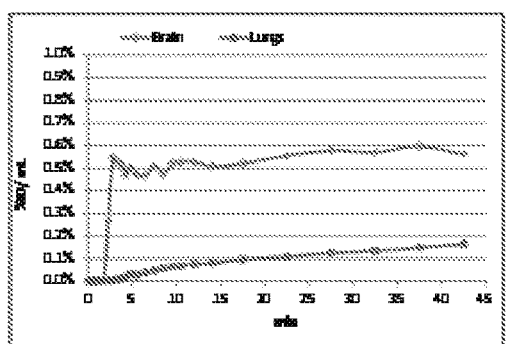
Figure 32A                    Figure 32B

A    B    C

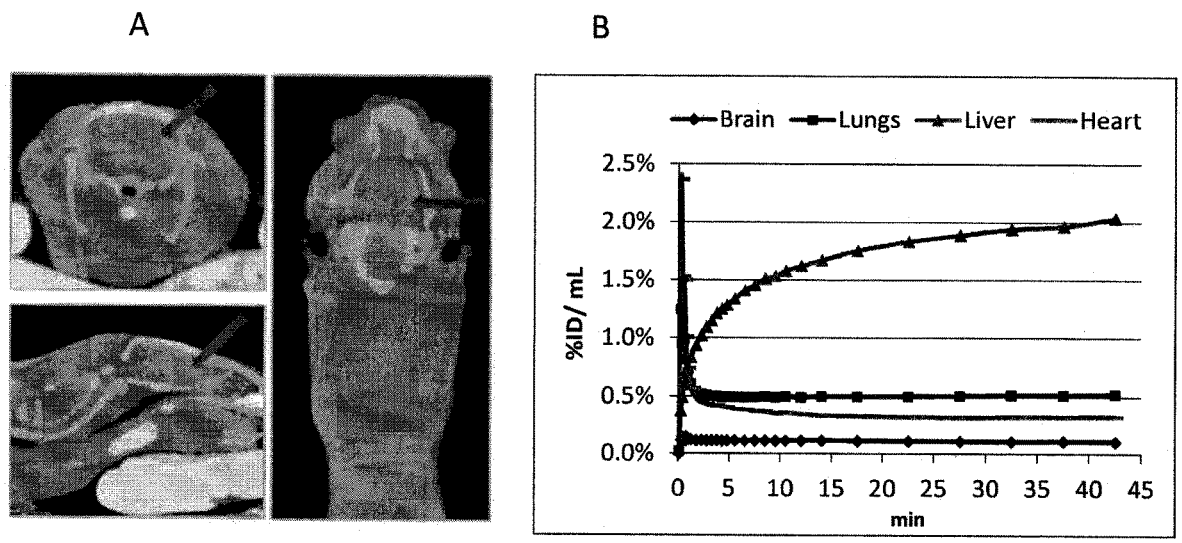
Figure 37
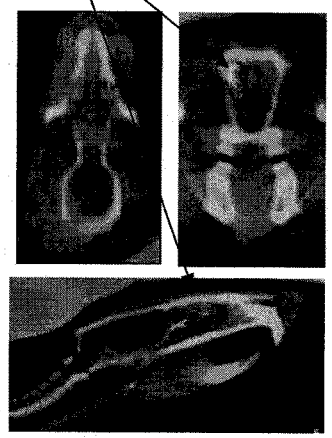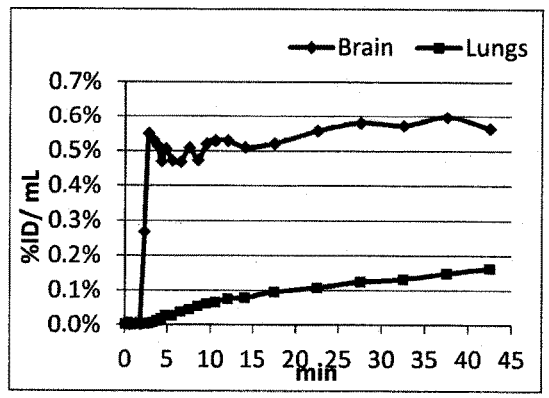
Olfactory epithelium deposition
A   Figure 38   B

NASAL DELIVERY DEVICE

FIELD OF THE INVENTION

The present invention generally pertains to a system and method for delivering substances to the nasal cavities. More specifically the present invention relates to the use of compressed air to carry/entrain flowable substance to the nasal passages. Thus, the present invention uses the energy stored in compressed air or gas as a carrier to deliver medicament to the nasal cavity. Furthermore, the volume of the air being compressed is in the range of the nasal cavity volume. Said volume serves as a carrier of a medicament for better dispersion and more targeted deposition in the nasal cavity.

The core concept of the present invention is the use of compressed air to entrain a substance and deliver the same through the nasal cavity. Furthermore, the core concept of the present invention is to provide a predetermined fixed/constant volume of compressed air, predetermined fixed/constant amount of pressure, predetermined fixed/constant amount of force; regardless of the abilities of the user.

BACKGROUND OF THE INVENTION

Patent application WO2006/108558 discloses a device for dosing and dry nebulization of nebulizable material chosen from a group comprising anti-infective agents and immunomodulators, comprising a nebulization channel, which has a first attachment piece and a second attachment piece, and a source of compressed carrier gas connected to the first attachment piece via a valve for the purpose of sending a carrier gas pressure pulse into the nebulization channel. The device is characterized in that between the first attachment piece and second attachment piece, and above the nebulization channel, a reservoir open only towards the nebulization channel, which contains the nebulizable material, is connected to the nebulization channel such that it is gas-tight with respect to the environment, and that, when the valve is closed, a pressure compensation takes place in the nebulization channel and in the reservoir. The invention also relates to a method for dosing and dry nebulization of such a nebulizable material by means of such a device.

However this device, intended for use in hospitals, requires an external source of compressed gas, and is therefore large and bulky.

Patent application WO2011/080761A1 requires coordination of breathing and activation, and both it and US2010/0300440A1 deliver the medicament via the mouth.

Another device of prior art, disclosed in PCT application no. PCT/IL2011/00702, is a nasal substance delivery device, wherein the substance is delivered to the nasal cavity employing either drinking or breathing to actuate the device.

Another device of the prior art, disclosed in U.S. Pat. No. 7,806,117 is a peroral powder delivery device having a capsule holder for loading the capsule into a body, the capsule holder attached so as to be capable of advancing into and retracting from the inside of the body. The body has a cutter blade to make holes on both ends of the capsule as it advances into the body while being held by the capsule holder. The body also has first and second air passageways having connection ports in communication with the holes in the capsule loaded in the body. The first air passageway has an inhaling port for inhaling the peroral powder in the capsule and the second air passageway has a suction valve that opens by the inhaling force from an inhaling port introducing air into the capsule.

However, the device of U.S. Pat. No. 7,806,117 differs significantly from the present device. Firstly, it is incapable of delivering the dose entrained in a predetermined fixed volume of air, moving with a well-defined speed (under a predetermined pressure). The volume of air in which the peroral powder is entrained and the speed of the air depend on the volume inspired by the user and the rapidity with which the user inhales, both of which differ significantly between, for example, men and women, adults and children, young people and elderly people, and healthy people and those with breathing difficulties.

Furthermore, the device of U.S. Pat. No. 7,806,117 is intended to deliver medication to the mouth (peroral delivery), not to the nose. If the device were modified for nasal delivery by reshaping the mouthpiece into a nosepiece, it would remain unlike the present device. For example, unlike the present device which provides a fixed pressure and air speed, the suction pressure and, therefore, the aid speed driving air flow through the peroral powder and into the nasal passages would be the suction pressure and air speed of the user's inhalation, a pressure and speed that will differ significantly between, for example, adults and children, young people and elderly people, and healthy people and those with breathing difficulties. Similarly, unlike the present device which provides a fixed volume of gas or air, the volume of air inhaled will differ significantly between, for example, men and women, adults and children, young people and elderly people, and healthy people and those with breathing difficulties.

If the device of U.S. Pat. No. 7,806,117 were to be modified to include a second tube, with one tube emplaced in the mouth and the second emplaced in a nostril, oral suction would result in air flowing from the nostril towards the mouth, rather than the desired direction, from the capsule towards the nostril. Inhalation simultaneous with oral suction would result in part of the peroral powder entering the nostril and part entering the mouth, with the fraction entering the nostril depending on the relative strengths of the suction and the inhalation, very far from the controlled delivery of the present device, with the entirety of the dose entering the nostril at a well-defined speed, entrained in a well-defined volume of air.

One of the major advantages of the present invention is the use of a constant, accurate and large volume of air.

Another device of the prior art, disclosed in U.S. Pat. No. 7,722,566 discloses a device that delivers a powdery medicine for a nasal cavity includes positioning guides that cause a capsule to slide as far as a predetermined position and are provided on the side of cutters to make holes on both ends of the capsule provided between the connection port on the side of a nozzle that sprays the powdery medicine into the nasal cavity. The device further includes a connection port on the side of a pump that supplies spray air to the nozzle in order to make the size of the holes made on both ends of the capsule constant, wherein a distance between the connection ports is made shorter than a distance between blade tips of the cutters.

This device differs significantly from the device of the present invention in being a one-step device, wherein compression of an elastic-walled space (the "pump") causes air to flow through the device, through a capsule containing medicament, and into both nostrils. The volume of air delivered by the device of U.S. Pat. No. 7,722,566 is more consistent than the volume of air delivered in U.S. Pat. No. 7,806,117, since it will be, in practice, a relatively consistent fraction of the volume of the pump, the fraction depending on the strength of the user and the physical properties of the elastic walls of the pump. Similarly, the air pressure delivering the air to the nostril and the air speed will be more consistent than U.S. Pat. No. 7,806,117, as they also depend on the strength of the user and the physical properties of the pump. However, the device of U.S. Pat. No. 7,722,566 differs from the present device in that, in the present device, none of the air speed, air volume or air pressure depends on the abilities of the user.

In addition, unlike the present device, the length of time over which the dose is delivered in U.S. Pat. No. 7,722,566 depends on how fast the user squeezes the pump. In the present device, the length of time over which the dose is delivered depends solely on the physical properties, such as shape and size, of the predetermined interior of the device.

Furthermore, the device of U.S. Pat. No. 7,722,566 is a one-step device—the user compresses the pump and the contents of the capsule are delivered. The present device is a two-step device, where the air chamber (the closest equivalent of the pump in U.S. Pat. No. 7,722,566) is charged with a fixed volume of air during a charging step. In an activation step, a valve is opened, the capsule is opened, and the contents of the air chamber are delivered to the nostril, ensuring that air pressure, air speed, air volume and time of delivery are completely consistent in in every activation.

Devices of prior art intended to deliver substances to the nasal passages are most commonly employed to deliver drugs and medicaments locally to the nasal cavity, to the lungs and to the blood, via the lower sections of the nasal passages. Difficulties have been experienced in delivering the substances to the central and upper sections of the nasal passages, such as the middle and upper turbinates. From the middle and upper turbinates, it is possible to deliver drugs to the brain, as pathways in the middle and upper turbinates can deliver medicaments across the thin ethmoid bone separating the nasal passages from the brain, bypassing the blood-brain barrier and allowing the passage of large or hydrophilic molecules that are unable to pass into the cerebrospinal fluid via the blood. The nasal route also enables delivery to the brain of substances that would otherwise be degraded by the digestive system and first pass metabolism in the liver if administered by the oral route. Also, the nasal route could serve as an alternative to parenteral route with greater user compliance, for the delivery of therapeutics to the brain and other tissues as lungs, heart and blood.

Many devices of prior art deliver the desired substance via a mist, usually in a liquid or gas carrier, with all the attendant disadvantages thereof. These include the degradation of medicaments during storage; unwanted interactions of drug with carrier; and the possibility of allergic reactions to the carrier. Also, those delivery applicators usually result in the presence of large droplets which are incapable of reaching the turbinates and possess limited absorption capability and wide dispersions of droplet size, which make control of deposition location difficult and cause variability in absorption rates and characteristics.

A further disadvantage of devices wherein the substance is entrained within an inert carrier (i.e., the pressurized gas) is that the volume and weight of the carrier is substantially larger than the volume and weight of the medicament.

Carrier-free delivery devices have depended on accurate control of breathing by the user, usually involving a prolonged inspiration, often accompanied by coordination of activation with inhalation. Prolonged inhalation is difficult for many patients, such as asthmatics, and coordination of inhalation with activation can be difficult, both for asthmatics and for small children. Also, in most cases, there is a straight correlation between the strength of the inhalation and the amount of medicament delivered.

Other carrier-free dry mist devices either require significant force to operate, beyond the strength of children and of weaker adults, or require a source of compressed gas so that they are large and bulky and are not easily transportable.

It is therefore a long felt need to provide a device that does not require coordination of breathing with activation, that does not require long or deep inspiration, that ensures reproducible and precise dose delivery in every activation and that is capable of delivering either medicaments in a carrier or carrier-free medicaments to the desired turbinates in the nose including the upper turbinates and, optionally, from there to the brain.

SUMMARY OF THE INVENTION

It is one object of the present invention to provide a two-step mechanism for delivering a flowable substance to the nasal passages, said device comprising:
  a. a nosepiece adapted to be in fluid connection with said nasal passages;
  b. at least one air-tight enclosure, comprising predetermined amount of compressed gas in the same; said compressed gas is pressurized to predetermined amount of pressure;
  c. a charging mechanism, fluidly connected with said air-tight enclosure, characterized by at least two configurations: a retracted position and an extended position; where, when said charging mechanism is transformed from said extended position to said retracted position, said charging mechanism is adapted to enable delivery of said pressurized and predetermined amount of compressed gas from at least one first predetermined position in said air-tight enclosure to at least one second predetermined position;
  d. an activation mechanism, adapted to reconfigure said charging mechanism from said extended position to said retracted position so as to entrain said flowable substance within said pressurized and predetermined amount of compressed gas and to deliver the same from said second predetermined position to said nasal passages.

It is another object of the present invention to provide the two-step mechanism, wherein said flowable substance is delivered to at least one selected from a group consisting of respiratory epithelium, olfactory epithelium, brain, lungs, pharynx, heart and any combination thereof through said nasal passages.

It is another object of the present invention to provide the two-step mechanism, wherein said predetermined amount of compressed gas is in volumes of about 5-50 ml and is compressed to a predetermined pressure in the range of about 1.5-10 bar.

It is another object of the present invention to provide the two-step mechanism, additionally comprising at least one container adapted to contain said flowable substance, said container in fluid connection with said charging mechanism and said nosepiece.

It is another object of the present invention to provide the two-step mechanism, additionally comprising a mouthpiece connected to said charging mechanism.

It is another object of the present invention to provide the two-step mechanism, wherein said mouthpiece is connected to said activation mechanism; further wherein said activation mechanism is adapted, upon activation of the same, to entrain said flowable substance within said pressurized and predetermined amount of compressed gas and to deliver the same to said nasal passages.

It is another object of the present invention to provide the two-step mechanism, wherein said activation is application of suction to the same through said mouthpiece.

It is another object of the present invention to provide the device as defined above, wherein said mouthpiece is adapted such that suction on said mouthpiece ensures closure of the mouth.

It is another object of the present invention to provide the device as defined above, wherein said closure of said mouth increases suction on said gas entering said nostril from said two step mechanism.

It is another object of the present invention to provide the two-step mechanism, wherein said reconfiguration from said extended position to said retracted position is performed by applying pressure on said charging mechanism.

It is another object of the present invention to provide the two-step mechanism, wherein said activation mechanism comprises a catch adapted, when said catch is released, to initiate delivery of said flowable substance to said nasal passages.

It is another object of the present invention to provide the two-step mechanism, wherein said activation mechanism comprises a button adapted, when said button is depressed, to initiate delivery of said flowable substance to said nasal passages.

It is another object of the present invention to provide the two-step mechanism, wherein said activation mechanism comprises a predetermined sound pattern adapted, when said predetermined sound pattern is detected, to initiate delivery of said flowable substance to said nasal passages.

It is another object of the present invention to provide the two-step mechanism, wherein said activation mechanism comprises a predetermined light pattern adapted, when said predetermined light pattern is detected, to initiate delivery of said flowable substance to said nasal passages.

It is another object of the present invention to provide the two-step mechanism, wherein said activation mechanism comprises a lever adapted, when said lever is moved from a first position to a second position, to initiate delivery of said flowable substance to said nasal passages.

It is another object of the present invention to provide the two-step mechanism, wherein said activation mechanism comprises a slider adapted, when said slider is moved from a first position to a second position, to initiate delivery of said flowable substance to said nasal passages.

It is another object of the present invention to provide the two-step mechanism, wherein said activation mechanism comprises a rotatable knob adapted, when said rotatable knob is rotated, to initiate delivery of said flowable substance to said nasal passages.

It is another object of the present invention to provide the two-step mechanism, wherein said activation mechanism comprises a latch adapted, when said latch is released, to initiate delivery of said flowable substance to said nasal passages.

It is another object of the present invention to provide the two-step mechanism, wherein said flowable substance comprises a medicament.

It is another object of the present invention to provide the two-step mechanism, wherein when said charging mechanism is transformed from said retracted position to said extended position, said charging mechanism is adapted to transfer gas into at least one said least one first predetermined position.

It is another object of the present invention to provide the two-step mechanism, additionally comprising a valve mechanism in fluid communication with said first predetermined position, said valve mechanism adapted to enable the commencement of delivery of said flowable substance to said nasal passages upon activation of said valve mechanism.

It is another object of the present invention to provide the two-step mechanism, wherein said flowable substance is selected from a group consisting of a liquid, a powder, an aerosol, a slurry, a gel, a suspension and any combination thereof.

It is another object of the present invention to provide the two-step mechanism, wherein said charging mechanism is a piston driven by moving a handle.

It is another object of the present invention to provide the two-step mechanism, wherein said charging mechanism is pressurized gas, contained within an enclosure adapted to enclose pressurized gas.

It is another object of the present invention to provide the two-step mechanism, wherein said flowable substance is contained within a flowable substance container (capsule) emplaceable within said two-step mechanism.

It is another object of the present invention to provide the two-step mechanism, wherein said charging mechanism comprises a piston sealingly contained in a shaft, said piston flexibly connected to a handle, said handle characterized by at least two configurations: a retracted position and an extended position, said shaft fluidly connected to an air-tight enclosure.

It is another object of the present invention to provide the two-step mechanism, wherein said shaft comprises said air-tight enclosure.

It is another object of the present invention to provide the two-step mechanism, wherein said charging mechanism comprises a pressurized gas enclosure adapted to enclose pressurized gas, said pressurized gas enclosure in fluid connection with said nosepiece.

It is another object of the present invention to provide the two-step mechanism, wherein said nosepiece is adapted to be removably emplaced in juxtaposition with a nostril, in a manner selected from a group consisting of sealingly emplaced within a nostril, sealingly emplaced against the opening of the nostril, loosely emplaced within a nostril, loosely emplaced against the opening of the nostril.

It is another object of the present invention to provide the two-step mechanism, wherein said charging mechanism comprises a filter, said filter adapted to remove from the gas at least one selected from a group consisting of particulates, bacteria, viruses, moisture, and undesired particles.

It is another object of the present invention to provide the two-step mechanism, wherein said flowable substance container adapted to contain said flowable substance (flowable substance capsule) is adapted to be removably emplaceable within said device.

It is another object of the present invention to provide the two-step mechanism, wherein said charging mechanism is characterized by three positions, a first position wherein said charging mechanism is retracted, a second position wherein said charging mechanism is partly extended, said capsule is lockable in position and charging is initiatable, and a third position wherein said charging mechanism is fully extended and said capsule is insertable.

It is another object of the present invention to provide the two-step mechanism, wherein said flowable substance capsule is removable from said device when said charging mechanism is in the fully extended position.

It is another object of the present invention to provide the two-step mechanism, wherein said flowable substance capsule is not removable from said device when said charging mechanism is not in said fully extended position.

It is another object of the present invention to provide the two-step mechanism, wherein said charging mechanism is adapted to open said flowable substance capsule.

It is another object of the present invention to provide the two-step mechanism, wherein said charging mechanism is adapted to open said flowable substance capsule during at least some portion of the time during which said charging mechanism is transformed from said extended position to said retracted position.

It is another object of the present invention to provide the two-step mechanism, wherein said charging mechanism is adapted to open said flowable substance capsule at the beginning of the time during which said charging mechanism is transformed from said extended position to said retracted position.

It is another object of the present invention to provide the two-step mechanism, wherein the means to open said flowable substance capsule is independent of said charging mechanism.

It is another object of the present invention to provide the two-step mechanism, wherein the means to open said flowable substance capsule is selected from a rod, a spear, a needle, a knife, a peel-off portion attached to said flowable substance capsule, and any combination thereof.

It is another object of the present invention to provide the two-step mechanism, wherein at least a portion of said nosepiece is removable from said device.

It is another object of the present invention to provide the two-step mechanism, wherein said nosepiece and said flowable substance capsule form a single unit.

It is another object of the present invention to provide the two-step mechanism, wherein said flowable substance capsule contains a single dose of said flowable substance.

It is another object of the present invention to provide the two-step mechanism, wherein said flowable substance capsule comprises a cartridge, said cartridge comprising a plurality of independently-openable containers, each said independently-openable container comprising (a) a single dose of said substance, (b) multiple doses of said substance, (c) different substances, (d) substance, (e) carrier and (f) any combination thereof.

It is another object of the present invention to provide the two-step mechanism, wherein said flowable substance capsule comprises a filter, said filter upstream of said substance, said filter adapted to remove from the gas at least one selected from a group consisting of particulates, bacteria, viruses, moisture, and undesired particles.

It is another object of the present invention to provide the two-step mechanism, wherein said device comprises a unidirectional valve such that gas is enabled to flow from the charging mechanism to the nostril, but is unable to flow in the reverse direction.

It is another object of the present invention to provide the two-step mechanism, wherein at least a portion of said mouthpiece is a member of a group consisting of removable, replaceable and any combination thereof.

It is another object of the present invention to provide the two-step mechanism, wherein said mouthpiece comprises an auxiliary air filter, said filter adapted to remove from gas passing through said filter at least one selected from a group consisting of particulates, bacteria, viruses, moisture, and undesired particles.

It is another object of the present invention to provide the two-step mechanism, wherein said mouthpiece is in fluid connection with a valve mechanism within said device such that suction on said mouthpiece opens said valve mechanism, thereby enabling flow of said pressurized and predetermined amount of compressed gas through said device.

It is another object of the present invention to provide the two-step mechanism, wherein said charging mechanism comprises a pump, said pump in fluid connection with a valve mechanism within said device such that suction on said mouthpiece opens said valve mechanism, thereby enabling flow of said pressurized and predetermined amount of compressed gas through said device.

It is another object of the present invention to provide the two-step mechanism, wherein said activation mechanism comprises a hollow flexible tegument, wherein compressing and releasing said tegument opens said valve mechanism, thereby enabling flow of said pressurized and predetermined amount of compressed gas through said device It is another object of the present invention to provide the two-step mechanism, wherein said predetermined position of said pressurized and predetermined amount of compressed gas is an air-tight enclosure within said device, said air-tight enclosure charged when said charging mechanism is transformed from said extended position to said retracted position, said charging mechanism is adapted to pressurize external gas into said air-tight enclosure.

It is another object of the present invention to provide the two-step mechanism, wherein said predetermined position of said pressurized and predetermined amount of compressed gas is a pressurized gas enclosure adapted to enclose pressurized gas, said pressurized gas enclosure in fluid connection with said nosepiece.

It is another object of the present invention to provide the two-step mechanism, wherein said pressurized gas enclosure and said flowable substance capsule form a single unit.

It is another object of the present invention to provide the two-step mechanism, wherein said pressurized gas enclosure and said flowable substance capsule form separate units.

It is another object of the present invention to provide the two-step mechanism, wherein said pressurized gas enclosure comprises a plurality of compartments.

It is another object of the present invention to provide the two-step mechanism, wherein said flowable substance capsule comprises a plurality of compartments.

It is another object of the present invention to provide the two-step mechanism, wherein at least one said compartment contains a substance different from the substance in at least one other said compartment.

It is another object of the present invention to provide the two-step mechanism, wherein said device is adapted for a predetermined target population.

It is another object of the present invention to provide the two-step mechanism, wherein said predetermined target population is persons of limited physical strength.

It is another object of the present invention to provide the two-step mechanism, wherein said predetermined target population is persons with difficulties coordinating breathing with activation of said device.

It is another object of the present invention to provide the two-step mechanism, wherein delivery factors adapted to provide optimum delivery of said substance are selected from a group consisting of the length of time over which the delivery occurs, the gas speed in the nostril during delivery, the gas speed in the nostril during delivery of the gas with entrained substance, the volume of gas entering the nostril, the excess gas pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the two-step mechanism, wherein parameters selected from a group consisting the size of the chamber, the strength of the spring, the strengths of any adjustable means, the diameter and length of the lower air chamber, the travel of the piston, frictional force between the piston seal (8) and the enclosure, the diameter of the air channel (14), the diameters of the inlet and outlet openings, the mass of the pressurized air, the volume within which the pressurized air is contained are adapted to ensure optimum delivery of said substance to a predetermined location in said nasal passages.

It is another object of the present invention to provide the two-step mechanism, wherein said predetermined location is selected from a group consisting of the lower turbinates, the middle turbinates, the upper turbinates, the ethmoid bone, and any combination thereof.

It is another object of the present invention to provide the two-step mechanism, wherein said container adapted to contain said flowable substance is adapted to be removably connectable to said device.

It is another object of the present invention to provide the two-step mechanism, wherein delivery factors adapted to provide optimum delivery of said substance are selected from a group consisting of the length of time over which the delivery occurs, the air speed in the nostril during delivery, the air speed in the nostril during delivery of the air with entrained substance, the volume of air entering the nostril, the excess air pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the two-step mechanism, wherein said charging mechanism is pressurized air, contained within a container adapted to enclose pressurized air.

It is another object of the present invention to provide the two-step mechanism, additionally comprising indicating means adapted to provide an indication the user if said entrainment of said flowable substance within said enclosed air and transport of the same from said container to said nasal passages has been successful.

It is another object of the present invention to provide the two-step mechanism, wherein said indication is visible by means of a change of color, audible by means of a predetermined sound pattern and any combination thereof.

It is another object of the present invention to provide the two-step mechanism, wherein said pressurized and predetermined amount of compressed gas is inert and will not react with said substance.

It is another object of the present invention to provide the two-step mechanism, wherein said substance is a medicament selected from a group consisting of saline, natural substances, medicaments for treatments for allergic rhinitis, medicaments for treatments for osteoporosis, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists, antagonists, antitussives, medicaments for treatment of motor disorders, antiepileptics, antipsychotics (neuroleptics), sedative-hypnotics, anxiolytics, centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, antihistamine, Astelin, Otrivin, Livostin, Theramax, Avamys, Luffeel, Sinofresh, Nasonex, Nasocort, Veramyst, medicaments for treatment of osteoporosis, Miacalcin, Fortical, Stadol, medicaments for vaccinations and immunizations, Lavin, influenza vaccines including FluMist, NasalFent. calcitonin, parathyroid hormone, neurotransmitters, neuromodulators, acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor, other growth factors, norepinephrine, nitric oxide, Substance P. alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, thiopental, benzocaine, bupivacaine, cocaine, lidocaine, prilocaine, procaine, ropivacaine, tetracaine, agonists, codeine, diphenoxylate, heroin, hydrocodone, 1-alpha-acetyl-methadol, levomethadyl acetate, loperamide, meperidine, methadone, oxycodone, d-propoxyphene, combinations of opioids plus acetaminophen, asa, tramadol, buprenorphine, butorphanol, nalbuphine, nalorphine, naloxone, naltrexone, nalmefene, pentazocine, codeine, dextromethorphan, hydrocodone, medicaments for treatment of Parkinson's disease and motor disorders, amantadine, apomorphine, baclofen, benzodiazepines, benztropine, bromocriptine, carbidopa, cyclobenzaprine, dantrolene, dopamine, entacapone, haloperidol, pergolide, pramiprexole, ropinerole, selegiline (L-deprenyl), trihexyphenidyl, rasagiline, Azilect, ladostigil, rotigotine, Neupro, mono amine oxidase inhibitor, COMT inhibitor, antiepileptics, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem, skeletal muscle relaxants, alprazolam, chlorazepate, chlordiazepoxide, diazepam, flumazenil, lorazepam, oxazepam, amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan, anti ADHD agents, anti ADHD drugs as Methylphenidrate (Ritalin), anti-autism and anti-autism symptoms drugs, medicaments for treatment of Alzheimer's disease, donepezil, galantamine, rivastigmine, tacrine, insulin, insulin detemir, Novolin, Humulin, insulin-like hormone, dopamine agonist, dopamine antagonist and any combination thereof.

It is another object of the present invention to provide a two-step mechanism for delivering a flowable substance to the nasal passages, said device comprising:
  a. a nosepiece adapted to be in fluid connection with said nasal passages;
  b. a charging mechanism fluidly connected with an air-tight enclosure; characterized by at least two configurations: a retracted position and an extended position wherein, when said charging mechanism is transformed from said retracted position to said extended position, said charging mechanism is adapted to withdraw predetermined amount of external gas into said air-tight enclosure; further wherein, when said charging mechanism is transformed from said extended position to said retracted position, said charging mechanism is adapted to pressurize said predetermined amount of external gas to a predetermined amount of pressure in said air-tight enclosure;
  c. an activation mechanism, adapted to reconfigure said charging mechanism from said extended position to said retracted position so as to entrain said flowable substance within said pressurized and predetermined amount of compressed gas and to deliver the same to said nasal passages.

It is another object of the present invention to provide the two-step mechanism, wherein said flowable substance is delivered to at least one selected from a group consisting of respiratory epithelium, olfactory epithelium, brain, lungs, pharynx, heart and any combination thereof through said nasal passages.

It is another object of the present invention to provide the two-step mechanism, wherein said predetermined amount of compressed gas is in volumes of about 5-50 ml and compressed to a predetermined amount of pressure in the range of about 1.5-10 bar.

It is another object of the present invention to provide the two-step mechanism, additionally comprising at least one container adapted to contain said flowable substance, said container in fluid connection with said charging mechanism and said nosepiece.

It is another object of the present invention to provide the two-step mechanism, additionally comprising a mouthpiece connected to said charging mechanism.

It is another object of the present invention to provide the two-step mechanism, wherein said mouthpiece is connected to said activation mechanism; further wherein said activation mechanism is adapted, upon activation of the same, to entrain said flowable substance within said pressurized and predetermined amount of compressed gas and to deliver the same to said nasal passages.

It is another object of the present invention to provide the two-step mechanism, wherein said activation is application of suction to the same through said mouthpiece.

It is another object of the present invention to provide the device as defined above, wherein said mouthpiece is adapted such that suction on said mouthpiece ensures closure of the mouth.

It is another object of the present invention to provide the device as defined above, wherein said closure of said mouth increases suction on said gas entering said nostril from said two step mechanism.

It is another object of the present invention to provide the two-step mechanism, wherein said reconfiguration from said first position to said second position is performed by applying pressure on said charging mechanism.

It is another object of the present invention to provide the two-step mechanism, wherein said activation mechanism comprises a catch adapted, when said catch is released, to initiate delivery of said flowable substance to said nasal passages.

It is another object of the present invention to provide the two-step mechanism, wherein said activation mechanism comprises a button adapted, when said button is depressed, to initiate delivery of said flowable substance to said nasal passages.

It is another object of the present invention to provide the two-step mechanism, wherein said activation mechanism comprises a predetermined sound pattern adapted, when said predetermined sound pattern is detected, to initiate delivery of said flowable substance to said nasal passages.

It is another object of the present invention to provide the two-step mechanism, wherein said activation mechanism comprises a predetermined light pattern adapted, when said predetermined light pattern is detected, to initiate delivery of said flowable substance to said nasal passages.

It is another object of the present invention to provide the two-step mechanism, wherein said activation mechanism comprises a lever adapted, when said lever is moved from a first position to a second position, to an activating position, to initiate delivery of said flowable substance to said nasal passages.

It is another object of the present invention to provide the two-step mechanism, wherein said activation mechanism comprises a slider adapted, when said slider is moved from a first position to a second position, to initiate delivery of said flowable substance to said nasal passages.

It is another object of the present invention to provide the two-step mechanism, wherein said activation mechanism comprises a rotatable knob adapted, when said rotatable knob is rotated, to initiate delivery of said flowable substance to said nasal passages.

It is another object of the present invention to provide the two-step mechanism, wherein said activation mechanism comprises a latch adapted, when said latch is released, to initiate delivery of said flowable substance to said nasal passages.

It is another object of the present invention to provide the two-step mechanism, wherein said activation mechanism comprises a valve adapted, when said charging mechanism is reconfigured from said first position to said second position, to open said first opening to said air-tight enclosure so as to enable said withdrawal of said pressurized and predetermined amount of compressed gas into said air-tight enclosure.

It is another object of the present invention to provide the two-step mechanism, wherein said activation mechanism comprises a valve adapted, when said charging mechanism is reconfigured from said second position to said first position, to close said first opening and to open said second opening so as to enable said entrainment of said flowable substance within said pressurized and predetermined amount of compressed gas and said delivery of the same to said nasal passages.

It is another object of the present invention to provide the two-step mechanism, wherein when said charging mechanism is transformed from said extended position to said retracted position, said charging mechanism is adapted to compress air within at least one said at least one first predetermined position.

It is another object of the present invention to provide the two-step mechanism, wherein when said charging mechanism is transformed from said retracted position to said extended position, said charging mechanism is adapted to transfer external air into at least one said least one first predetermined position.

It is another object of the present invention to provide the two-step mechanism, additionally comprising a valve mechanism in fluid communication with said first predetermined position, said valve mechanism adapted to enable the commencement of delivery of said flowable substance to said nasal passages upon activation of said valve mechanism.

It is another object of the present invention to provide the two-step mechanism, wherein said flowable substance comprises a medicament.

It is another object of the present invention to provide the two-step mechanism, wherein said flowable substance is selected from a group consisting of a liquid, a powder, an aerosol, a slurry, a gel, a suspension and any combination thereof.

It is another object of the present invention to provide the two-step mechanism, wherein said charging mechanism comprises a piston sealingly contained in a shaft, said piston flexibly connected to a handle, said handle characterized by at least two configurations: a retracted position and an extended position, with said shaft fluidly connected to said air-tight enclosure.

It is another object of the present invention to provide the two-step mechanism, wherein said shaft comprises said air-tight enclosure.

It is another object of the present invention to provide the two-step mechanism, wherein said nosepiece is adapted to be removably emplaced in juxtaposition with a nostril, in a manner selected from a group consisting of sealingly emplaced within a nostril, sealingly emplaced against the opening of the nostril, loosely emplaced within a nostril, loosely emplaced against the opening of the nostril.

It is another object of the present invention to provide the two-step mechanism, wherein said charging mechanism comprises a filter, said filter adapted to remove from the external air at least one selected from a group consisting of particulates, bacteria, viruses, moisture, and undesired particles.

It is another object of the present invention to provide the two-step mechanism, wherein said flowable substance container adapted to contain said flowable substance (flowable substance capsule) is adapted to be removably emplaceable within said device.

It is another object of the present invention to provide the two-step mechanism, wherein said charging mechanism is characterized by three positions, a first position wherein said charging mechanism is retracted, a second position wherein said charging mechanism is partly extended, said capsule is lockable in position and charging is initiatable, and a third position wherein said charging mechanism is fully extended and said capsule is insertable.

It is another object of the present invention to provide the two-step mechanism, wherein said flowable substance capsule is removable from said device when said charging mechanism is in the fully extended position.

It is another object of the present invention to provide the two-step mechanism, wherein said flowable substance capsule is not removable from said device when said charging mechanism is not in said fully extended position.

It is another object of the present invention to provide the two-step mechanism, wherein said charging mechanism is adapted to open said flowable substance capsule.

It is another object of the present invention to provide the two-step mechanism, wherein said charging mechanism is adapted to open said flowable substance capsule during at least some portion of the time during which said charging mechanism is transformed from said extended position to said retracted position.

It is another object of the present invention to provide the two-step mechanism, wherein said charging mechanism is adapted to open said flowable substance capsule at the beginning of the time during which said charging mechanism is transformed from said extended position to said retracted position.

It is another object of the present invention to provide the two-step mechanism, wherein the means to open said flowable substance capsule is independent of said charging mechanism.

It is another object of the present invention to provide the two-step mechanism, wherein the means to open said flowable substance capsule is selected from a rod, a spear, a needle, a knife, a peel-off portion attached to said flowable substance capsule, and any combination thereof.

It is another object of the present invention to provide the two-step mechanism, wherein at least a portion of said nosepiece is removable from said device.

It is another object of the present invention to provide the two-step mechanism, wherein said nosepiece and said flowable substance capsule form a single unit.

It is another object of the present invention to provide the two-step mechanism, wherein said flowable substance capsule contains a single dose of said flowable substance.

It is another object of the present invention to provide the two-step mechanism, wherein said flowable substance capsule comprises a cartridge, said cartridge comprising a plurality of independently-openable containers, each said independently-openable container comprising (a) a single dose of said substance, (b) multiple doses of said substance, (c) different substances, (d) substance, (e) carrier and any combination thereof.

It is another object of the present invention to provide the two-step mechanism, wherein said flowable substance capsule comprises a filter, said filter upstream of said substance, said filter adapted to remove from the external air at least one selected from a group consisting of particulates, bacteria, viruses, moisture, and undesired particles.

It is another object of the present invention to provide the two-step mechanism, wherein said device comprises a unidirectional valve such that air is enabled to flow from the charging mechanism to the nostril, but is unable to flow in the reverse direction.

It is another object of the present invention to provide the two-step mechanism, wherein at least a portion of said mouthpiece is a member of a group consisting of removable, replaceable and any combination thereof.

It is another object of the present invention to provide the two-step mechanism, wherein said mouthpiece comprises an auxiliary air filter, said filter adapted to remove from the external air at least one selected from a group consisting of particulates, bacteria, viruses, moisture, and undesired particles.

It is another object of the present invention to provide the two-step mechanism, wherein said mouthpiece is in fluid connection with a valve mechanism within said device such that suction on said mouthpiece opens said valve mechanism, thereby enabling flow of said pressurized and predetermined amount of compressed gas through said device.

It is another object of the present invention to provide the two-step mechanism, wherein said activation mechanism comprises a hollow flexible tegument, wherein compressing and releasing said tegument opens said valve mechanism, thereby enabling flow of said pressurized and predetermined amount of compressed gas through said device.

It is another object of the present invention to provide the two-step mechanism, wherein said activation mechanism comprises one of a group consisting of a compressible spring, a magnetic field, an electric field and a piezoelectric device, said activation mechanism activated by means selected from a group consisting of a releasable catch, a pressable button, a flippable switch, a rotatable knob and a movable lever, said activation mechanism opening said valve mechanism, thereby enabling flow of said pressurized and predetermined amount of compressed gas through said device.

It is another object of the present invention to provide the two-step mechanism, wherein said flowable substance capsule comprises a plurality of compartments.

It is another object of the present invention to provide the two-step mechanism, wherein at least one said compartment contains a substance different from the substance in at least one other said compartment.

It is another object of the present invention to provide the two-step mechanism, wherein delivery factors adapted to provide optimum delivery of said substance are selected from a group consisting of the length of time over which the delivery occurs, the air speed in the nostril during delivery, the air speed in the nostril during delivery of the air with entrained substance, the volume of air entering the nostril, the excess air pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the two-step mechanism, wherein parameters selected from a group consisting of the size of the chamber, the strength of the spring, the strengths of any adjustable means, the diameter and length of the lower air chamber, the diameter of the air channel, the diameters of the inlet and outlet openings, the mass of the pressurized gas, the volume within which the pressurized gas is contained are adapted to ensure optimum delivery of said substance to a predetermined location in said nasal passages.

It is another object of the present invention to provide the two-step mechanism, wherein said predetermined location is selected from a group consisting of the lower turbinates, the middle turbinates, the upper turbinates, the ethmoid bone, and any combination thereof.

It is another object of the present invention to provide the two-step mechanism, wherein said container adapted to contain said flowable substance is adapted to be removably connectable to said device.

It is another object of the present invention to provide the two-step mechanism, wherein said nosepiece is removable from said device.

It is another object of the present invention to provide the two-step mechanism, wherein said container contains a single dose of said flowable substance.

It is another object of the present invention to provide the two-step mechanism, wherein said device comprises a unidirectional valve such that gas is enabled to flow from the charging mechanism to the nostril, but is unable to flow in the reverse direction.

It is another object of the present invention to provide the two-step mechanism, wherein said device is adapted for a predetermined target population.

It is another object of the present invention to provide the two-step mechanism, wherein said predetermined target population is persons of limited physical strength.

It is another object of the present invention to provide the two-step mechanism, wherein said predetermined target population is persons with difficulties coordinating breathing with activation of said device.

It is another object of the present invention to provide the two-step mechanism, wherein said charging mechanism is pressurized gas, contained within a container adapted to enclose pressurized gas.

It is another object of the present invention to provide the two-step mechanism, additionally comprising indicating means adapted to provide an indication the user if said entrainment of said flowable substance within said enclosed air and transport of the same from said container to said nasal passages has been successful.

It is another object of the present invention to provide the two-step mechanism, wherein said indication is visible by means of a change of color, audible by means of a predetermined sound pattern and any combination thereof.

It is another object of the present invention to provide the two-step mechanism, wherein said activation mechanism comprises a pump, said pump in fluid connection with a valve mechanism within said device such that activation mechanism opens said valve mechanism, thereby enabling flow of said pressurized and predetermined amount of compressed gas through said device.

It is another object of the present invention to provide the two-step mechanism, wherein said activation mechanism comprises one of a group consisting of a spring, a magnetic field, an electric field and a piezoelectric device, said activation mechanism activated by means selected from a group consisting of a button, a switch, a knob and a lever, said activation mechanism opening said valve mechanism, thereby enabling flow of said pressurized and predetermined amount of compressed gas through said device.

It is another object of the present invention to provide the two-step mechanism, wherein said predetermined position of said pressurized and predetermined amount of compressed gas is a pressurized gas container adapted to enclose pressurized gas, said pressurized gas container in fluid connection with said nosepiece.

It is another object of the present invention to provide the two-step mechanism, wherein said predetermined amount of compressed gas is inert and will not react with said substance.

It is another object of the present invention to provide the two-step mechanism, wherein said substance is a medicament selected from a group consisting of saline, natural substances, medicaments for treatments for allergic rhinitis, medicaments for treatments for osteoporosis, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists, antagonists, antitussives, medicaments for treatment of motor disorders, antiepileptics, antipsychotics (neuroleptics), sedative-hypnotics, anxiolytics, and centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, antihistamine, Astelin, Otrivin, Livostin, Theramax, Avamys, Luffeel, Sinofresh, Nasonex, Nasocort, Veramyst, medicaments for treatment of osteoporosis, Miacalcin, Fortical, Stadol, medicaments for vaccinations and immunizations, Lavin, influenza vaccines including FluMist, NasalFent. calcitonin, parathyroid hormone, neurotransmitters, neuromodulators, acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor, other growth factors, norepinephrine, nitric oxide, Substance P. alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, thiopental, benzocaine, bupivacaine, cocaine, lidocaine, prilocaine, procaine, ropivacaine, tetracaine, agonists, codeine, diphenoxylate, heroin, hydrocodone, 1-alpha-acetyl-methadol, levomethadyl acetate, loperamide, meperidine, methadone, oxycodone, d-propoxyphene, combinations of opioids plus acetaminophen and asa, tramadol, buprenorphine, butorphanol, nalbuphine, nalorphine, naloxone, naltrexone, nalmefene, pentazocine, codeine, dextromethorphan, hydrocodone, medicaments for treatment of Parkinson's disease and motor disorders, amantadine, apomorphine, baclofen, benzodiazepines, benztropine, bromocriptine, carbidopa, cyclobenzaprine, dantrolene, dopamine, entacapone, haloperidol, pergolide, pramiprexole, ropinerole, selegiline (L-deprenyl), trihexyphenidyl, rasagiline, Azilect, ladostigil, rotigotine, Neupro, mono amine oxidase inhibitor, COMT inhibitor, antiepileptics, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem, skeletal muscle relaxants, alprazolam, chlorazepate, chlordiazepoxide, diazepam, flumazenil, lorazepam, oxazepam, amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan, anti ADHD agents, anti ADHD drugs, Methylphenidrate (Ritalin), anti-autism and anti-autism symptoms drugs, medicaments for treatment of Alzheimer's disease, donepezil, galantamine, rivastigmine, tacrine, insulin, insulin detemir, Novolin, Humulin, insulin-like hormone, dopamine agonist, dopamine antagonist and any combination thereof.

It is another object of the present invention to provide a method for delivering a flowable substance to the nasal passages, comprising steps of:
a. providing a two-step mechanism for delivering a flowable substance to the nasal passages, said device comprising:
   i. a nosepiece adapted to be in fluid connection with said nasal passages;
   ii. at least one air-tight enclosure, comprising predetermined amount of compressed gas in the same; said compressed gas is pressurized to predetermined amount of pressure;
   iii. a charging mechanism fluidly connected with said air-tight enclosure, characterized by at least two configurations: a retracted position and an extended position; where, when said charging mechanism is transformed from said extended position to said retracted position, said charging mechanism is adapted to enable delivery of said pressurized and predetermined amount of compressed gas from at least one first predetermined position in said air-tight enclosure to at least one second predetermined position; and
   iv. an activation mechanism, adapted to entrain said flowable substance within said pressurized and predetermined amount of compressed gas and to deliver the same to said nasal passages;
b. providing said flowable substance, contained within a container;
c. fluidly connecting said container with said charging mechanism and said nosepiece;
d. charging said device by transforming said charging mechanism from said extended position to said retracted position;
e. emplacing said nosepiece in juxtaposition with a nostril in fluid connection with said nasal passages; and
f. activating said device.

It is another object of the present invention to provide the method, comprising an additional step of delivering said flowable substance to at least one selected from a group consisting of respiratory epithelium, olfactory epithelium, brain, lungs, pharynx, heart and any combination thereof through said nasal passages.

It is another object of the present invention to provide the method, comprising an additional step of adapting said device to provide said predetermined amount of compressed gas in volumes of about 5-50 ml and compressed to a predetermined amount of pressure in the range of about 1.5 to about 10 bar.

It is another object of the present invention to provide the method, comprising an additional step of providing at least one container adapted to contain said flowable substance, said container in fluid connection with said charging mechanism and said nosepiece.

It is another object of the present invention to provide the method, comprising an additional step of providing a mouthpiece connected to said charging mechanism.

It is another object of the present invention to provide the method, comprising an additional step of connecting said mouthpiece to said activation mechanism; further wherein said activation mechanism are adapted, upon activation of the same, to entrain said flowable substance within said pressurized and predetermined amount of compressed gas and to deliver the same to said nasal passages.

It is another object of the present invention to provide the method, comprising an additional step of activating said two-step mechanism by application of suction to the same through said mouthpiece.

It is another object of the present invention to provide the method as defined above, additionally comprising a step of adapting said mouthpiece such that suction on said mouthpiece ensures closure of the mouth.

It is another object of the present invention to provide the method as defined above, wherein said closure of said mouth increases suction on said gas entering said nostril from said two step mechanism It is another object of the present invention to provide the method, comprising an additional step of performing said reconfiguration from said first position to said second position by applying pressure on said charging mechanism.

It is another object of the present invention to provide the method, comprising an additional step of providing said activation mechanism comprising a catch adapted, when said catch is released, to initiate delivery of said flowable substance to said nasal passages.

It is another object of the present invention to provide the method, comprising an additional step of providing said activation mechanism comprising a button adapted, when said button is depressed, to initiate delivery of said flowable substance to said nasal passages.

It is another object of the present invention to provide the method, comprising an additional step of adapting said activation mechanism such that, when at least one predetermined sound pattern is detected, delivery of said flowable substance to said nasal passages is initiated.

It is another object of the present invention to provide the method, comprising an additional step of adapting said activation mechanism such that, when at least one predetermined light pattern detected, delivery of said flowable substance to said nasal passages is initiated.

It is another object of the present invention to provide the method, comprising an additional step of providing said activation mechanism comprising a lever adapted, when said lever is moved from a first position to a second position, to an activating position, to initiate delivery of said flowable substance to said nasal passages.

It is another object of the present invention to provide the method, comprising an additional step of providing said activation mechanism comprising a slider adapted, when said slider is moved from a first position to a second position, to initiate delivery of said flowable substance to said nasal passages.

It is another object of the present invention to provide the method, comprising an additional step of providing said activation mechanism comprising a rotatable knob adapted, when said rotatable knob is rotated, to initiate delivery of said flowable substance to said nasal passages.

It is another object of the present invention to provide the method, comprising an additional step of providing said activation mechanism comprising a latch adapted, when said latch is released, to initiate delivery of said flowable substance to said nasal passages.

It is another object of the present invention to provide the method, comprising an additional step of providing said flowable substance comprising a medicament.

It is another object of the present invention to provide the method, comprising an additional step of, when said charging mechanism is transformed from said retracted position to said extended position, adapting said charging mechanism to transfer gas into at least one said least one first predetermined position.

It is another object of the present invention to provide the method, comprising an additional step of providing a valve mechanism in fluid communication with said first predetermined position, said valve mechanism adapted to enable the commencement of delivery of said flowable substance to said nasal passages upon activation of said valve mechanism.

It is another object of the present invention to provide the method, comprising an additional step of selecting said flowable substance from a group consisting of a liquid, a powder, an aerosol, a slurry, a gel, a suspension and any combination thereof.

It is another object of the present invention to provide the method, comprising an additional step of providing said charging mechanism comprising a piston driven by moving a handle.

It is another object of the present invention to provide the method, comprising an additional step of providing said charging mechanism comprising pressurized gas, contained within an enclosure adapted to enclose pressurized gas.

It is another object of the present invention to provide the method, comprising an additional step of containing said flowable substance within a flowable substance container (capsule) emplaceable within said two-step mechanism.

It is another object of the present invention to provide the method, comprising an additional step of providing said charging mechanism comprising a piston sealingly contained in a shaft, said piston flexibly connected to a handle, said handle characterized by at least two configurations: a retracted position and an extended position, said shaft fluidly connected to an air-tight enclosure.

It is another object of the present invention to provide the method, comprising an additional step of providing said shaft comprising said air-tight enclosure.

It is another object of the present invention to provide the method, comprising an additional step of providing said charging mechanism comprising a pressurized gas enclosure adapted to enclose pressurized gas, said pressurized gas enclosure in fluid connection with said nosepiece.

It is another object of the present invention to provide the method, comprising an additional step of adapting said nosepiece to be removably emplaced in juxtaposition with a nostril, in a manner selected from a group consisting of sealingly emplaced within a nostril, sealingly emplaced against the opening of the nostril, loosely emplaced within a nostril, loosely emplaced against the opening of the nostril.

It is another object of the present invention to provide the method, comprising an additional step of providing said charging mechanism comprising a filter, said filter adapted to remove from the gas at least one selected from a group consisting of particulates, bacteria, viruses, moisture, and undesired particles.

It is another object of the present invention to provide the method, comprising an additional step of adapting said flowable substance container to contain said flowable substance (flowable substance capsule) is adapted to be removably emplaceable within said device.

It is another object of the present invention to provide the method, comprising an additional step of characterizing said charging mechanism by three positions, a first position wherein said charging mechanism is retracted, a second position wherein said charging mechanism is partly extended, said capsule is lockable in position and charging is initiatable, and a third position wherein said charging mechanism is fully extended and said capsule is insertable.

It is another object of the present invention to provide the method, comprising an additional step of providing said flowable substance capsule such that the same is removable from said device when said charging mechanism is in the fully extended position.

It is another object of the present invention to provide the method, comprising an additional step of providing said flowable substance capsule such that it the same is not removable from said device when said charging mechanism is not in said fully extended position.

It is another object of the present invention to provide the method, comprising an additional step of adapting said charging mechanism to open said flowable substance capsule.

It is another object of the present invention to provide the method, comprising an additional step of adapting said charging mechanism to open said flowable substance capsule during at least some portion of the time during which said charging mechanism is transformed from said extended position to said retracted position.

It is another object of the present invention to provide the method, comprising an additional step of adapting said charging mechanism is adapted said flowable substance capsule at the beginning of the time during which said charging mechanism is transformed from said extended position to said retracted position.

It is another object of the present invention to provide the method, comprising an additional step of providing the means to open said flowable substance capsule independently of said charging mechanism.

It is another object of the present invention to provide the method, comprising an additional step of selecting the means to open said flowable substance capsule from a rod, a spear, a needle, a knife, a peel-off portion attached to said flowable substance capsule, and any combination thereof.

It is another object of the present invention to provide the method, comprising an additional step of providing at least a portion of said nosepiece such that the same is removable from said device.

It is another object of the present invention to provide the method, comprising an additional step of providing said nosepiece and said flowable substance capsule forming a single unit.

It is another object of the present invention to provide the method, comprising an additional step of providing said flowable substance capsule containing a single dose of said flowable substance.

It is another object of the present invention to provide the method, comprising an additional step of providing said flowable substance capsule comprising a cartridge, said cartridge comprising a plurality of independently-openable containers, each said independently-openable container comprising (a) a single dose of said substance, (b) multiple doses of said substance, (c) different substances, (d) substance, (e) carrier and (f) any combination thereof.

It is another object of the present invention to provide the method, comprising an additional step of providing said flowable substance capsule comprising a filter, said filter upstream of said substance, said filter adapted to remove from the gas at least one selected from a group consisting of particulates, bacteria, viruses, moisture, and undesired particles.

It is another object of the present invention to provide the method, comprising an additional step of providing said device comprising a unidirectional valve such that gas is enabled to flow from the charging mechanism to the nostril, but is unable to flow in the reverse direction.

It is another object of the present invention to provide the method as defined above, comprising an additional step of providing at least a portion of said mouthpiece such that the same is a member of a group consisting of removable, replaceable and any combination thereof.

It is another object of the present invention to provide the method, comprising an additional step of providing said mouthpiece comprising an auxiliary air filter, said filter adapted to remove from gas passing through said filter at least one selected from a group consisting of particulates, bacteria, viruses, moisture, and undesired particles.

It is another object of the present invention to provide the method as defined above, comprising an additional step of providing said mouthpiece in fluid connection with a valve mechanism within said device such that suction on said mouthpiece opens said valve mechanism, thereby enabling flow of said pressurized and predetermined amount of compressed gas through said device.

It is another object of the present invention to provide the method as defined above, comprising an additional step of providing said charging mechanism comprising a pump, said pump in fluid connection with a valve mechanism within said device such that suction on said mouthpiece opens said valve mechanism, thereby enabling flow of said pressurized and predetermined amount of compressed gas through said device.

It is another object of the present invention to provide the method as defined above, comprising an additional step of providing said activation mechanism comprising a hollow flexible tegument, wherein compressing and releasing said tegument opens said valve mechanism, thereby enabling flow of said pressurized and predetermined amount of compressed gas through said device It is another object of the present invention to provide the method as defined above, comprising an additional step of providing said predetermined position of said pressurized and predetermined amount of compressed gas such that the same is an air-tight enclosure within said device, said air-tight enclosure charged when said charging mechanism is transformed from said extended position to said retracted position, said charging mechanism is adapted to pressurize external gas into said air-tight enclosure.

It is another object of the present invention to provide the method as defined above, comprising an additional step of providing said predetermined position of said pressurized and predetermined amount of compressed gas such that the same is a pressurized gas enclosure adapted to enclose pressurized gas, said pressurized gas enclosure in fluid connection with said nosepiece.

It is another object of the present invention to provide the method as defined above, comprising an additional step of providing said pressurized gas enclosure and said flowable substance capsule forming a single unit.

It is another object of the present invention to provide the method as defined above, comprising an additional step of providing said pressurized gas enclosure and said flowable substance capsule forming separate units.

It is another object of the present invention to provide the method as defined above, comprising an additional step of providing said pressurized gas enclosure comprising a plurality of compartments.

It is another object of the present invention to provide the method as defined above, comprising an additional step of providing said flowable substance capsule comprising a plurality of compartments.

It is another object of the present invention to provide the method as defined above, comprising an additional step of providing at least one said compartment containing a substance different from the substance in at least one other said compartment.

It is another object of the present invention to provide the method as defined above, comprising an additional step of adapting said device for a predetermined target population.

It is another object of the present invention to provide the method as defined above, comprising an additional step of selecting said predetermined target population to be persons of limited physical strength.

It is another object of the present invention to provide the method as defined above, comprising an additional step of selecting said predetermined target population to be persons with difficulties coordinating breathing with activation of said device.

It is another object of the present invention to provide the method as defined above, comprising an additional step of selecting delivery factors adapted to provide optimum delivery of said substance from a group consisting of the length of time over which the delivery occurs, the gas speed in the nostril during delivery, the gas speed in the nostril during delivery of the gas with entrained substance, the volume of gas entering the nostril, the excess gas pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the method as defined above, comprising an additional step of selecting parameters from a group consisting the size of the chamber, the strength of the spring, the strengths of any adjustable means, the diameter and length of the lower air chamber, the travel of the piston, frictional force between the piston seal (8) and the enclosure, the diameter of the air channel (14), the diameters of the inlet and outlet openings, the mass of the pressurized air, the volume within which the pressurized air is contained are adapted to ensure optimum delivery of said substance to a predetermined location in said nasal passages.

It is another object of the present invention to provide the method as defined above, comprising an additional step of selecting said predetermined location from a group consisting of the lower turbinates, the middle turbinates, the upper turbinates, the ethmoid bone, and any combination thereof.

It is another object of the present invention to provide the method as defined above, comprising an additional step of providing said container adapted to contain said flowable substance adapted to be removably connectable to said device.

It is another object of the present invention to provide the method as defined above, comprising an additional step of selecting delivery factors adapted to provide optimum delivery of said substance from a group consisting of the length of time over which the delivery occurs, the air speed in the nostril during delivery, the air speed in the nostril during delivery of the air with entrained substance, the volume of air entering the nostril, the excess air pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the method as defined above, comprising an additional step of selecting said charging mechanism to be pressurized air, contained within a container adapted to enclose pressurized air.

It is another object of the present invention to provide the method as defined above, comprising an additional step of providing indicating means adapted to provide an indication to the user if said entrainment of said flowable substance within said enclosed air and transport of the same from said container to said nasal passages has been successful.

It is another object of the present invention to provide the method as defined above, comprising an additional step of making said indication visible by means of a change of color, audible by means of a predetermined sound pattern and any combination thereof.

It is another object of the present invention to provide the method as defined above, comprising an additional step of providing said predetermined amount of compressed gas inert and non-reactive with said substance.

It is another object of the present invention to provide the method as defined above, comprising an additional step of selecting said substance as a medicament from a group consisting of saline, natural substances, medicaments for treatments for allergic rhinitis, medicaments for treatments for osteoporosis, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists, antagonists, antitussives, medicaments for treatment of motor disorders, antiepileptics, antipsychotics (neuroleptics), sedative-hypnotics, anxiolytics, and centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, antihistamine, Astelin, Otrivin, Livostin, Theramax, Avamys, Luffeel, Sinofresh, Nasonex, Nasocort, Veramyst, medicaments for treatment of osteoporosis, Miacalcin, Fortical, Stadol, medicaments for vaccinations and immunizations, Lavin, influenza vaccines including FluMist, NasalFent. calcitonin, parathyroid hormone, neurotransmitters, neuromodulators, acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor, other growth factors, norepinephrine, nitric oxide, Substance P. alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, thiopental, benzocaine, bupivacaine, cocaine, lidocaine, prilocaine, procaine, ropivacaine, tetracaine, agonists, codeine, diphenoxylate, heroin, hydrocodone, 1-alpha-acetyl-methadol, levomethadyl acetate, loperamide, meperidine, methadone, oxycodone, d-propoxyphene, combinations of opioids plus acetaminophen and asa, tramadol, buprenorphine, butorphanol, nalbuphine, nalorphine, naloxone, naltrexone, nalmefene, pentazocine, codeine, dextromethorphan, hydrocodone, medicaments for treatment of Parkinson's disease and motor disorders, amantadine, apomorphine, baclofen, benzodiazepines, benztropine, bromocriptine, carbidopa, cyclobenzaprine, dantrolene, dopamine, entacapone, haloperidol, pergolide, pramiprexole, ropinerole, selegiline (L-deprenyl), trihexyphenidyl, rasagiline, Azilect, ladostigil, rotigotine, Neupro, mono amine oxidase inhibitor, COMT inhibitor, antiepileptics, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem, skeletal muscle relaxants, alprazolam, chlorazepate, chlordiazepoxide, diazepam, flumazenil, lorazepam, oxazepam, amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan, anti ADHD agents, anti ADHD drugs, Methylphenidrate (Ritalin), anti-autism and anti-autism symptoms drugs, medicaments for treatment of Alzheimer's disease, donepezil, galantamine, rivastigmine, tacrine, insulin, insulin detemir, Novolin, Humulin, insulin-like hormone, dopamine agonist, dopamine antagonist and any combination thereof.

It is another object of the present invention to provide a method for delivering a flowable substance to the nasal passages, comprising steps of:
  a. providing a two-step mechanism for delivering a flowable substance to the nasal passages, said device comprising:
    i. a nosepiece adapted to be in fluid connection with said nasal passages;
    ii. a charging mechanism fluidly connected with an air-tight enclosure; characterized by at least two configurations: a retracted position and an extended position wherein, when said charging mechanism is transformed from said retracted position to said extended position, said charging mechanism is adapted to withdraw predetermined amount of external gas into said air-tight enclosure; further wherein, when said charging mechanism is transformed from said extended position to said retracted position, said charging mechanism is adapted to pressurize said predetermined amount of external gas to a predetermined amount of pressure in said air-tight enclosure; and
    iii. an activation mechanism, adapted to reconfigure said charging mechanism from said extended position to said retracted position so as to entrain said flowable substance within said pressurized and predetermined amount of compressed gas and to deliver the same to said nasal passages;
  b. providing said flowable substance, contained within a container;
  c. fluidly connecting said container with said charging mechanism and said nosepiece;
  d. charging said device by transforming said charging mechanism from said retracted position to said extended position;
  e. emplacing said nosepiece in juxtaposition with a nostril in fluid connection with said nasal passages; and
  f. activating said device.

It is another object of the present invention to provide the method as defined above, comprising an additional step of delivering said flowable substance to at least one selected from a group consisting of respiratory epithelium, olfactory epithelium, brain, lungs, pharynx, heart and any combination thereof through said nasal passages.

It is another object of the present invention to provide the method as defined above, comprising an additional step of adapting said device to provide predetermined amount of compressed gas is in volumes of about 5-50 ml and compressed to a predetermined amount of pressure in the range of about 1.5-10 bar.

It is another object of the present invention to provide the method as defined above, comprising an additional step of providing at least one container adapted to contain said flowable substance, said container in fluid connection with said charging mechanism and said nosepiece.

It is another object of the present invention to provide the method as defined above, comprising an additional step of providing a mouthpiece connected to said charging mechanism.

It is another object of the present invention to provide the method as defined above, comprising an additional step of connecting said mouthpiece to said activation mechanism; further wherein said activation mechanism are adapted, upon activation of the same, to entrain said flowable substance within said pressurized and predetermined amount of compressed gas and to deliver the same to said nasal passages.

It is another object of the present invention to provide the method as defined above, comprising an additional step of activating said two-step mechanism by application of suction to the same through said mouthpiece.

It is another object of the present invention to provide the method as defined above, additionally comprising a step of adapting said mouthpiece such that suction on said mouthpiece ensures closure of the mouth.

It is another object of the present invention to provide the method as defined above, wherein said closure of said mouth increases suction on said gas entering said nostril from said two step mechanism It is another object of the present invention to provide the method as defined above, comprising an additional step of performing said reconfiguration from said first position to said second position by applying pressure on said charging mechanism.

It is another object of the present invention to provide the method as defined above, comprising an additional step of providing an activation mechanism adapted to reconfigure said charging mechanism from at least one of said first position to second position and from said second position to said first position.

It is another object of the present invention to provide the method as defined above, comprising an additional step of providing said activation mechanism comprising a catch adapted, when said catch is released, to initiate delivery of said flowable substance to said nasal passages.

It is another object of the present invention to provide the method as defined above, comprising an additional step of providing said activation mechanism comprising a button adapted, when said button is depressed, to initiate delivery of said flowable substance to said nasal passages.

It is another object of the present invention to provide the method as defined above, comprising an additional step of providing said activation mechanism comprising a predetermined sound pattern adapted, when said predetermined sound pattern is detected, to initiate delivery of said flowable substance to said nasal passages.

It is another object of the present invention to provide the method as defined above, comprising an additional step of providing said activation mechanism comprising a predetermined light pattern adapted, when said predetermined light pattern is detected, to initiate delivery of said flowable substance to said nasal passages.

It is another object of the present invention to provide the method as defined above, comprising an additional step of providing said activation mechanism comprising a lever adapted, when said lever is moved from a first position to a second position, to an activating position, to initiate delivery of said flowable substance to said nasal passages.

It is another object of the present invention to provide the method as defined above, comprising an additional step of providing said activation mechanism comprising a slider adapted, when said slider is moved from a first position to a second position, to initiate delivery of said flowable substance to said nasal passages.

It is another object of the present invention to provide the method as defined above, comprising an additional step of providing said activation mechanism comprising a rotatable knob adapted, when said rotatable knob is rotated, to initiate delivery of said flowable substance to said nasal passages.

It is another object of the present invention to provide the method as defined above, comprising an additional step of providing said activation mechanism comprising a latch adapted, when said latch is released, to initiate delivery of said flowable substance to said nasal passages.

It is another object of the present invention to provide the method as defined above, comprising an additional step of providing said activation mechanism comprising a valve adapted, when said charging mechanism is reconfigured from said first position to said second position, to open said first opening to said air-tight enclosure so as to enable said withdrawal of said pressurized and predetermined amount of compressed gas into said air-tight enclosure.

It is another object of the present invention to provide the method as defined above, comprising an additional step of providing said activation mechanism comprising a valve adapted, when said charging mechanism is reconfigured from said second position to said first position, to close said first opening and to open said second opening so as to enable said entrainment of said flowable substance within said pressurized and predetermined amount of compressed and said delivery of the same to said nasal passages.

It is another object of the present invention to provide the method as defined above, comprising an additional step of, when said charging mechanism is transformed from said retracted position to said extended position, adapting said charging mechanism to transfer gas into at least one said least one first predetermined position.

It is another object of the present invention to provide the method as defined above, comprising an additional step of providing a valve mechanism in fluid communication with said first predetermined position, said valve mechanism adapted to enable the commencement of delivery of said flowable substance to said nasal passages upon activation of said valve mechanism.

It is another object of the present invention to provide the method as defined above, comprising an additional step of selecting said flowable substance from a group consisting of a liquid, a powder, an aerosol, a slurry, a gel, a suspension and any combination thereof.

It is another object of the present invention to provide the method as defined above, comprising an additional step of providing said charging mechanism comprising a piston driven by moving a handle.

It is another object of the present invention to provide the method as defined above, comprising an additional step of providing said charging mechanism comprising pressurized gas, contained within an enclosure adapted to enclose pressurized gas.

It is another object of the present invention to provide the method as defined above, comprising an additional step of containing said flowable substance within a flowable substance container (capsule) emplaceable within said two-step mechanism.

It is another object of the present invention to provide the method as defined above, comprising an additional step of providing said charging mechanism comprising a piston sealingly contained in a shaft, said piston flexibly connected to a handle, said handle characterized by at least two configurations: a retracted position and an extended position, said shaft fluidly connected to an air-tight enclosure.

It is another object of the present invention to provide the method as defined above, comprising an additional step of providing said shaft comprising said air-tight enclosure.

It is another object of the present invention to provide the method as defined above, comprising an additional step of providing said charging mechanism comprising a pressurized gas enclosure adapted to enclose pressurized gas, said pressurized gas enclosure in fluid connection with said nosepiece.

It is another object of the present invention to provide the method as defined above, comprising an additional step of adapting said nosepiece to be removably emplaced in juxtaposition with a nostril, in a manner selected from a group consisting of sealingly emplaced within a nostril, sealingly emplaced against the opening of the nostril, loosely emplaced within a nostril, loosely emplaced against the opening of the nostril.

It is another object of the present invention to provide the method as defined above, comprising an additional step of providing said charging mechanism comprising a filter, said filter adapted to remove from the gas at least one selected from a group consisting of particulates, bacteria, viruses, moisture, and undesired particles.

It is another object of the present invention to provide the method as defined above, comprising an additional step of adapting said flowable substance container to contain said flowable substance (flowable substance capsule) is adapted to be removably emplaceable within said device.

It is another object of the present invention to provide the method as defined above, comprising an additional step of characterizing said charging mechanism by three positions, a first position wherein said charging mechanism is retracted, a second position wherein said charging mechanism is partly extended, said capsule is lockable in position and charging is initiatable, and a third position wherein said charging mechanism is fully extended and said capsule is insertable.

It is another object of the present invention to provide the method as defined above, comprising an additional step of providing said flowable substance capsule such that the same is removable from said device when said charging mechanism is in the fully extended position.

It is another object of the present invention to provide the method as defined above, comprising an additional step of providing said flowable substance capsule such that it the same is not removable from said device when said charging mechanism is not in said fully extended position.

It is another object of the present invention to provide the method as defined above, comprising an additional step of adapting said charging mechanism to open said flowable substance capsule.

It is another object of the present invention to provide the method as defined above, comprising an additional step of adapting said charging mechanism to open said flowable substance capsule during at least some portion of the time during which said charging mechanism is transformed from said extended position to said retracted position.

It is another object of the present invention to provide the method as defined above, comprising an additional step of adapting said charging mechanism is adapted said flowable substance capsule at the beginning of the time during which said charging mechanism is transformed from said extended position to said retracted position.

It is another object of the present invention to provide the method as defined above, comprising an additional step of providing the means to open said flowable substance capsule independently of said charging mechanism.

It is another object of the present invention to provide the method as defined above, comprising an additional step of selecting the means to open said flowable substance capsule from a rod, a spear, a needle, a knife, a peel-off portion attached to said flowable substance capsule, and any combination thereof.

It is another object of the present invention to provide the method as defined above, comprising an additional step of providing at least a portion of said nosepiece such that the same is removable from said device.

It is another object of the present invention to provide the method as defined above, comprising an additional step of providing said nosepiece and said flowable substance capsule forming a single unit.

It is another object of the present invention to provide the method as defined above, comprising an additional step of providing said flowable substance capsule containing a single dose of said flowable substance.

It is another object of the present invention to provide the method as defined above, comprising an additional step of providing said flowable substance capsule comprising a cartridge, said cartridge comprising a plurality of independently-openable containers, each said independently-openable container comprising (a) a single dose of said substance, (b) multiple doses of said substance, (c) different substances, (d) substance, (e) carrier and (f) any combination thereof.

It is another object of the present invention to provide the method as defined above, comprising an additional step of providing said flowable substance capsule comprising a filter, said filter upstream of said substance, said filter adapted to remove from the gas at least one selected from a group consisting of particulates, bacteria, viruses, moisture, and undesired particles.

It is another object of the present invention to provide the method as defined above, comprising an additional step of providing said device comprising a unidirectional valve such that gas is enabled to flow from the charging mechanism to the nostril, but is unable to flow in the reverse direction.

It is another object of the present invention to provide the method as defined above, comprising an additional step of providing at least a portion of said mouthpiece such that the same is a member of a group consisting of removable, replaceable and any combination thereof.

It is another object of the present invention to provide the method as defined above, comprising an additional step of providing said mouthpiece comprising an auxiliary air filter, said filter adapted to remove from gas passing through said filter at least one selected from a group consisting of particulates, bacteria, viruses, moisture, and undesired particles.

It is another object of the present invention to provide the method as defined above, comprising an additional step of providing said mouthpiece in fluid connection with a valve mechanism within said device such that suction on said mouthpiece opens said valve mechanism, thereby enabling flow of said pressurized and predetermined amount of compressed gas through said device.

It is another object of the present invention to provide the method as defined above, comprising an additional step of providing said charging mechanism comprising a pump, said pump in fluid connection with a valve mechanism within said device such that suction on said mouthpiece opens said valve mechanism, thereby enabling flow of said pressurized and predetermined amount of compressed gas through said device.

It is another object of the present invention to provide the method as defined above, comprising an additional step of providing said activation mechanism comprising a hollow flexible tegument, wherein compressing and releasing said tegument opens said valve mechanism, thereby enabling flow of said pressurized and predetermined amount of compressed gas through said device It is another object of the present invention to provide the method as defined above, comprising an additional step of providing said predetermined position of said pressurized and predetermined amount of compressed gas such that the same is an air-tight enclosure within said device, said air-tight enclosure charged when said charging mechanism is transformed from said extended position to said retracted position, said charging mechanism is adapted to pressurize external gas into said air-tight enclosure.

It is another object of the present invention to provide the method as defined above, comprising an additional step of providing said predetermined position of said pressurized and predetermined amount of compressed gas such that the same is a pressurized gas enclosure adapted to enclose pressurized gas, said pressurized gas enclosure in fluid connection with said nosepiece.

It is another object of the present invention to provide the method as defined above, comprising an additional step of providing said pressurized gas enclosure and said flowable substance capsule forming a single unit.

It is another object of the present invention to provide the method as defined above, comprising an additional step of providing said pressurized gas enclosure and said flowable substance capsule forming separate units.

It is another object of the present invention to provide the method as defined above, comprising an additional step of providing said pressurized gas enclosure comprising a plurality of compartments.

It is another object of the present invention to provide the method as defined above, comprising an additional step of providing said flowable substance capsule comprising a plurality of compartments.

It is another object of the present invention to provide the method as defined above, comprising an additional step of providing at least one said compartment containing a substance different from the substance in at least one other said compartment.

It is another object of the present invention to provide the method as defined above, comprising an additional step of adapting said device for a predetermined target population.

It is another object of the present invention to provide the method as defined above, comprising an additional step of selecting said predetermined target population to be persons of limited physical strength.

It is another object of the present invention to provide the method as defined above, comprising an additional step of selecting said predetermined target population to be persons with difficulties coordinating breathing with activation of said device.

It is another object of the present invention to provide the method as defined above, comprising an additional step of selecting delivery factors adapted to provide optimum delivery of said substance from a group consisting of the length of time over which the delivery occurs, the gas speed in the nostril during delivery, the gas speed in the nostril during delivery of the gas with entrained substance, the volume of gas entering the nostril, the excess gas pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the method as defined above, comprising an additional step of selecting parameters from a group consisting of the size of the chamber, the strength of the spring, the strengths of any adjustable means, the diameter and length of the lower air chamber, the diameter of the air channel, the diameters of the inlet and outlet openings, the mass of the pressurized gas, the volume within which the pressurized gas is contained are adapted to ensure optimum delivery of said substance to a predetermined location in said nasal passages.

It is another object of the present invention to provide the method as defined above, comprising an additional step of selecting said predetermined location from a group consisting of the lower turbinates, the middle turbinates, the upper turbinates, the ethmoid bone, and any combination thereof.

It is another object of the present invention to provide the method as defined above, comprising an additional step of providing said container adapted to contain said flowable substance adapted to be removably connectable to said device.

It is another object of the present invention to provide the method as defined above, comprising an additional step of said nosepiece is removable from said device.

It is another object of the present invention to provide the method as defined above, comprising an additional step of providing said container containing a single dose of said flowable substance.

It is another object of the present invention to provide the method as defined above, comprising an additional step of adapting said device for a predetermined target population.

It is another object of the present invention to provide the method as defined above, comprising an additional step of selecting said predetermined target population to be persons of limited physical strength.

It is another object of the present invention to provide the method as defined above, comprising an additional step of selecting said predetermined target population to be persons with difficulties coordinating breathing with activation of said device.

It is another object of the present invention to provide the method as defined above, comprising an additional step of selecting said charging mechanism to be pressurized gas, contained within a container adapted to enclose pressurized gas.

It is another object of the present invention to provide the method as defined above, comprising an additional step of providing indicating means adapted to provide an indication the user if said entrainment of said flowable substance within said enclosed air and transport of the same from said container to said nasal passages has been successful.

It is another object of the present invention to provide the method as defined above, comprising an additional step of making said indication visible by means of a change of color, audible by means of a predetermined sound pattern and any combination thereof.

It is another object of the present invention to provide the method as defined above, comprising an additional step of providing said activation mechanism comprising a pump, said pump in fluid connection with a valve mechanism within said device such that activation mechanism opens said valve mechanism, thereby enabling flow of said pressurized and predetermined amount of compressed gas through said device It is another object of the present invention to provide the method as defined above, comprising an additional step of selecting said activation mechanism from of a group consisting of a spring, a magnetic field, an electric field and a piezoelectric device, said activation mechanism activated by means selected from a group consisting of a button, a switch, a knob and a lever, said activation mechanism opening said valve mechanism, thereby enabling flow of said pressurized and predetermined amount of compressed gas through said device.

It is another object of the present invention to provide the method as defined above, comprising an additional step of selecting said predetermined position of said pressurized and predetermined amount of compressed gas to be a pressurized gas container adapted to enclose pressurized gas, said pressurized gas container in fluid connection with said nosepiece.

It is another object of the present invention to provide the method as defined above, comprising an additional step of selecting said pressurized and predetermined amount of compressed gas such that it is inert and will not react with said substance.

It is another object of the present invention to provide the method as defined above, comprising an additional step of selecting said substance as a medicament from a group consisting of saline, natural substances, medicaments for treatments for allergic rhinitis, medicaments for treatments for osteoporosis, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists, antagonists, antitussives, medicaments for treatment of motor disorders, antiepileptics, antipsychotics (neuroleptics), sedative-hypnotics, anxiolytics, centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, antihistamine, Astelin, Otrivin, Livostin, Theramax, Avamys, Luffeel, Sinofresh, Nasonex, Nasocort, Veramyst, medicaments for treatment of osteoporosis, Miacalcin, Fortical, Stadol, medicaments for vaccinations and immunizations, Lavin, influenza vaccines including FluMist, NasalFent. calcitonin, parathyroid hormone, neurotransmitters, neuromodulators, acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor and other growth factors), norepinephrine, nitric oxide, Substance P. alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, thiopental, benzocaine, bupivacaine, cocaine, lidocaine, prilocaine, procaine, ropivacaine, tetracaine, agonists, codeine, diphenoxylate, heroin, hydrocodone, 1-alpha-acetyl-methadol, levomethadyl acetate, loperamide, meperidine, methadone, oxycodone, d-propoxyphene, combinations of opioids plus acetaminophen and asa, tramadol, buprenorphine, butorphanol, nalbuphine, nalorphine, naloxone, naltrexone, nalmefene, pentazocine, codeine, dextromethorphan, hydrocodone, medicaments for treatment of Parkinson's disease and motor disorders, amantadine, apomorphine, baclofen, benzodiazepines, benztropine, bromocriptine, carbidopa, cyclobenzaprine, dantrolene, dopamine, entacapone, haloperidol, pergolide, pramiprexole, ropinerole, selegiline (L-deprenyl), trihexyphenidyl, rasagiline, Azilect, ladostigil, rotigotine, Neupro, mono amine oxidase inhibitor, COMT inhibitor, antiepileptics, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem, skeletal muscle relaxants, alprazolam, chlorazepate, chlordiazepoxide, diazepam, flumazenil, lorazepam, oxazepam, amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan, anti ADHD agents, anti ADHD drugs, Methylphenidrate (Ritalin), anti-autism and anti-autism symptoms drugs, medicaments for treatment of Alzheimer's disease, donepezil, galantamine, rivastigmine, tacrine, insulin, insulin detemir, Novolin, Humulin, insulin-like hormone, dopamine agonist, dopamine antagonist and any combination thereof.

It is another object of the present invention to provide a device for delivering a flowable substance to the nasal passages comprising:

a. a distal end and a proximal end interconnected to one another by a main longitudinal axis; said distal end comprising:
  i. a nosepiece adapted to be in fluid connection with said nasal passages; and said proximal end comprising a charging mechanism fluidly connected with said nosepiece, said charging mechanism comprising:
  ii. a shaft located parallel to said main longitudinal axis, comprising;
  iii. an air-tight enclosure; and,
  iv. a handle rotatably connected to said shaft, said handle characterized by at least two positions, a retracted position and an extended position; where, when said handle is transformed from said retracted position to said extended position, said charging mechanism is adapted to withdraw predetermined amount of external gas into said air-tight enclosure; further wherein, when said handle is transformed from said extended position to said retracted position, said charging mechanism is adapted to pressurize said predetermined amount of external gas in said air-tight enclosure to a predetermined amount of pressure;
b. an activation mechanism adapted to reconfigure said charging mechanism from said extended position to said retracted position so as to entrain said flowable substance within said pressurized and predetermined amount of compressed gas and to deliver the same to said nasal passages.

It is another object of the present invention to provide the device as defined above, additionally comprising at least one mouthpiece adapted to be emplaced in the mouth of a user.

It is another object of the present invention to provide the device as defined above, wherein said mouthpiece is connected to said activation mechanism; further wherein said activation mechanism is adapted, upon activation of the same, to entrain said flowable substance within said pressurized and predetermined amount of compressed gas and to deliver the same to said nasal passages. It is another object of the present invention to provide the device as defined above, wherein said activation is application of suction to the same through said mouthpiece.

It is another object of the present invention to provide the device as defined above, wherein said mouthpiece is adapted such that suction on said mouthpiece ensures closure of the mouth. It is another object of the present invention to provide the device as defined above, wherein said closure of said mouth increases suction on said gas entering said nostril from said two step mechanism.

It is another object of the present invention to provide the device as defined above, additionally comprising at least one container adapted to contain said flowable substance, said container in fluid connection with said air-tight enclosure and said nosepiece.

It is another object of the present invention to provide the device as defined above, wherein said flowable substance is delivered to at least one selected from a group consisting of respiratory epithelium, olfactory epithelium, brain, lungs, pharynx, heart and any combination thereof through said nasal passages.

It is another object of the present invention to provide the device as defined above, wherein said compressed enclosed air is in volumes of about 5-50 ml and compressed to a predetermined amount of pressure in the range of about 1.5-10 bar.

It is another object of the present invention to provide the device as defined above, wherein said charging mechanism further comprises a piston sealingly contained in said shaft, said piston flexibly connected to said handle, said piston driven by said handle.

It is another object of the present invention to provide the device as defined above, wherein when said charging mechanism is transformed from said extended position to said retracted position, said charging mechanism is adapted to compress air within at least one said at least one first predetermined position.

It is another object of the present invention to provide the device as defined above, wherein when said charging mechanism is transformed from said retracted position to said extended position, said charging mechanism is adapted to transfer external air into at least one said least one first predetermined position.

It is another object of the present invention to provide the device as defined above, additionally comprising a valve mechanism in fluid communication with said first predetermined position, said valve mechanism adapted to enable the commencement of delivery of said flowable substance to said nasal passages upon activation of said valve mechanism.

It is another object of the present invention to provide the device as defined above, wherein said flowable substance comprises a medicament.

It is another object of the present invention to provide the device as defined above, wherein said flowable substance is selected from a group consisting of a liquid, a powder, an aerosol, a slurry, a gel, a suspension and any combination thereof.

It is another object of the present invention to provide the device as defined above, wherein said nosepiece is adapted to be removably emplaced within a nostril, in a manner selected from a group consisting of sealingly emplaced within a nostril, sealingly emplaced against the opening of the nostril, loosely emplaced within a nostril, loosely emplaced against the opening of the nostril.

It is another object of the present invention to provide the device as defined above, wherein said charging mechanism comprises a filter, said filter adapted to remove from the external air at least one selected from a group consisting of particulates, bacteria, viruses, moisture, and undesired particles.

It is another object of the present invention to provide the device as defined above, wherein said flowable substance container adapted to contain said flowable substance (flowable substance capsule) is adapted to be removably emplaceable within said device.

It is another object of the present invention to provide the device as defined above, wherein said charging mechanism is characterized by three positions, a first position wherein said charging mechanism is retracted, a second position wherein said charging mechanism is partly extended, said capsule is lockable in position and charging is initiatable, and a third position wherein said charging mechanism is fully extended and said capsule is insertable.

It is another object of the present invention to provide the device as defined above, wherein said flowable substance capsule is removable from said device when said charging mechanism is in the fully extended position.

It is another object of the present invention to provide the device as defined above, wherein said flowable substance capsule is not removable from said device when said charging mechanism is not in said fully extended position.

It is another object of the present invention to provide the device as defined above, wherein said charging mechanism is adapted to open said flowable substance capsule.

It is another object of the present invention to provide the device as defined above, wherein said charging mechanism is adapted to open said flowable substance capsule during at least some portion of the time during which said charging mechanism is transformed from said extended position to said retracted position.

It is another object of the present invention to provide the device as defined above, wherein said charging mechanism is adapted to open said flowable substance capsule at the beginning of the time during which said charging mechanism is transformed from said extended position to said retracted position.

It is another object of the present invention to provide the device as defined above, wherein the means to open said flowable substance capsule is independent of said charging mechanism.

It is another object of the present invention to provide the device as defined above, wherein the means to open said flowable substance capsule is selected from a rod, a spear, a needle, a knife, a peel-off portion attached to said flowable substance capsule, and any combination thereof.

It is another object of the present invention to provide the device as defined above, wherein at least a portion of said nosepiece is removable from said device.

It is another object of the present invention to provide the device as defined above, wherein said nosepiece and said flowable substance capsule form a single unit.

It is another object of the present invention to provide the device as defined above, wherein said flowable substance capsule contains a single dose of said flowable substance.

It is another object of the present invention to provide the device as defined above, wherein said flowable substance capsule comprises a cartridge, said cartridge comprising a plurality of independently-openable containers, each said independently-openable container comprising (a) a single dose of said substance, (b) multiple doses of said substance, (c) different substances, (d) substance, (e) carrier and any combination thereof.

It is another object of the present invention to provide the device as defined above, wherein said flowable substance capsule comprises a filter, said filter upstream of said substance, said filter adapted to remove from the external air at least one selected from a group consisting of particulates, bacteria, viruses, moisture, and undesired particles.

It is another object of the present invention to provide the device as defined above, wherein said device comprises a unidirectional valve such that air is enabled to flow from the charging mechanism to the nostril, but is unable to flow in the reverse direction.

It is another object of the present invention to provide the device as defined above, wherein at least a portion of said mouthpiece is a member of a group consisting of removable, replaceable and any combination thereof.

It is another object of the present invention to provide the device as defined above, wherein said mouthpiece comprises an auxiliary air filter, said filter adapted to remove from the external air at least one selected from a group consisting of particulates, bacteria, viruses, moisture, and undesired particles.

It is another object of the present invention to provide the device as defined above, wherein said mouthpiece is in fluid connection with a valve mechanism within said device such that suction on said mouthpiece opens said valve mechanism, thereby enabling flow of said pressurized and predetermined amount of compressed gas through said device.

It is another object of the present invention to provide the device as defined above, wherein said activation mechanism comprises a hollow flexible tegument, wherein compressing and releasing said tegument opens said valve mechanism, thereby enabling flow of said pressurized and predetermined amount of compressed gas through said device.

It is another object of the present invention to provide the device as defined above, wherein said activation mechanism comprises one of a group consisting of a compressible spring, a magnetic field, an electric field and a piezoelectric device, said activation mechanism activated by means selected from a group consisting of a releasable catch, a pressable button, a flippable switch, a rotatable knob and a movable lever, said activation mechanism opening said valve mechanism, thereby enabling flow of said pressurized and predetermined amount of compressed gas through said device.

It is another object of the present invention to provide the device as defined above, wherein said flowable substance capsule comprises a plurality of compartments.

It is another object of the present invention to provide the device as defined above, wherein at least one said compartment contains a substance different from the substance in at least one other said compartment.

It is another object of the present invention to provide the device as defined above, wherein said device is adapted for a predetermined target population.

It is another object of the present invention to provide the device as defined above, wherein said predetermined target population is persons of limited physical strength.

It is another object of the present invention to provide the device as defined above, wherein said predetermined target population is persons with difficulties coordinating breathing with activation of said device.

It is another object of the present invention to provide the device as defined above, wherein delivery factors adapted to provide optimum delivery of said substance are selected from a group consisting of the length of time over which the delivery occurs, the air speed in the nostril during delivery, the air speed in the nostril during delivery of the air with entrained substance, the volume of air entering the nostril, the excess air pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the device as defined above, additionally comprising indicating means adapted to provide an indication the user if said entrain of said flowable substance within said enclosed air and transport the same from said container to said nasal passages has been successful.

It is another object of the present invention to provide the device as defined above, wherein said indication is visible by means of a change of color, audible by means of a predetermined sound pattern and any combination thereof.

It is another object of the present invention to provide the device as defined above, wherein said compressed gas, is inert and will not react with said substance.

It is another object of the present invention to provide the device as defined above, wherein said substance is a medicament selected from a group consisting of saline, natural substances, medicaments for treatments for allergic rhinitis, medicaments for treatments for osteoporosis, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists, antagonists, antitussives, medicaments for treatment of motor disorders, antiepileptics, antipsychotics (neuroleptics), sedative-hypnotics, anxiolytics, centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, antihistamine, Astelin, Otrivin, Livostin, Theramax, Avamys, Luffeel, Sinofresh, Nasonex, Nasocort, Veramyst, medicaments for treatment of osteoporosis, Miacalcin, Fortical, Stadol, medicaments for vaccinations and immunizations, Lavin, influenza vaccines including FluMist, NasalFent. calcitonin, parathyroid hormone, neurotransmitters, neuromodulators, acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor, other growth factors, norepinephrine, nitric oxide, Substance P. alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, thiopental, benzocaine, bupivacaine, cocaine, lidocaine, prilocaine, procaine, ropivacaine, tetracaine, agonists, codeine, diphenoxylate, heroin, hydrocodone, 1-alpha-acetyl-methadol, levomethadyl acetate, loperamide, meperidine, methadone, oxycodone, d-propoxyphene, combinations of opioids plus acetaminophen and asa, tramadol, buprenorphine, butorphanol, nalbuphine, nalorphine, naloxone, naltrexone, nalmefene, pentazocine, codeine, dextromethorphan, hydrocodone, medicaments for treatment of Parkinson's disease and motor disorders, amantadine, apomorphine, baclofen, benzodiazepines, benztropine, bromocriptine, carbidopa, cyclobenzaprine, dantrolene, dopamine, entacapone, haloperidol, pergolide, pramiprexole, ropinerole, selegiline (L-deprenyl), trihexyphenidyl, rasagiline, Azilect, ladostigil, rotigotine, Neupro, mono amine oxidase inhibitor, COMT inhibitor, antiepileptics, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem, a skeletal muscle relaxants, alprazolam, chlorazepate, chlordiazepoxide, diazepam, flumazenil, lorazepam, oxazepam, amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan, anti ADHD agents, anti ADHD drugs, Methylphenidrate (Ritalin), anti-autism and anti-autism symptoms drugs, medicaments for treatment of Alzheimer's disease, donepezil, galantamine, rivastigmine, tacrine, insulin, insulin detemir, Novolin, Humulin, insulin-like hormone, dopamine agonist, dopamine antagonist and any combination thereof.

It is another object of the present invention to provide a device for delivering a flowable substance to the nasal passages comprising:
  a. a distal end and a proximal end interconnected by a main longitudinal axis; said distal end comprising:
    i. a nosepiece adapted to be in fluid connection with said nasal passages; said proximal end comprising a charging mechanism fluidly connected with said nosepiece, said charging mechanism comprising:
      i. a shaft;
      ii. at least one air-tight enclosure, comprising predetermined amount of compressed gas in the same; said compressed gas is pressurized to predetermined amount of pressure;
      iii. a handle rotatably connected to said shaft, said handle characterized by at least two positions, a retracted position and an extended position; where, when said handle is transformed from said extended position to said retracted position, said handle is adapted to enable delivery of said pressurized and predetermined amount of compressed gas from at least one first predetermined position in said air-tight enclosure to at least one second predetermined position;
  b. an activation mechanism, adapted to reconfigure said handle from said extended position to said retracted position so as to entrain said flowable substance within said pressurized and predetermined amount of compressed gas and to deliver the same to said nasal passages.

It is another object of the present invention to provide the device as defined above, wherein said flowable substance is delivered to at least one selected from a group consisting of respiratory epithelium, olfactory epithelium, brain, lungs, pharynx, heart and any combination thereof through said nasal passages.

It is another object of the present invention to provide the device as defined above, wherein said compressed enclosed air is in volumes of about 5-50 ml and compressed to a predetermined amount of pressure in the range of about 1.5-10 bar.

It is another object of the present invention to provide the device as defined above, additionally comprising at least one container adapted to contain said flowable substance, said container in fluid connection with said charging mechanism and said nosepiece.

It is another object of the present invention to provide the device as defined above, additionally comprising a mouthpiece connected to said charging mechanism to be emplaced in the mouth of a user.

It is another object of the present invention to provide the device as defined above, wherein said mouthpiece is connected to said activation mechanism; further wherein said activation mechanism is adapted, upon activation of the same, to entrain said flowable substance within said pressurized and predetermined amount of compressed gas and to deliver the same to said nasal passages.

It is another object of the present invention to provide the device as defined above, wherein said activation is application of suction to the same through said mouthpiece.

It is another object of the present invention to provide the device as defined above, wherein said mouthpiece is adapted such that suction on said mouthpiece ensures closure of the mouth. It is another object of the present invention to provide the device as defined above, wherein said closure of said mouth increases suction on said gas entering said nostril from said two step mechanism.

It is another object of the present invention to provide the device as defined above, wherein when said charging mechanism is transformed from said extended position to said retracted position, said charging mechanism is adapted to compress gas within at least one said at least one first predetermined position.

It is another object of the present invention to provide the device as defined above, wherein when said charging mechanism is transformed from said retracted position to said extended position, said charging mechanism is adapted to transfer gas into at least one said least one first predetermined position.

It is another object of the present invention to provide the device as defined above, additionally comprising a valve mechanism in fluid communication with said first predetermined position, said valve mechanism adapted to enable the commencement of delivery of said flowable substance to said nasal passages upon activation of said valve mechanism.

It is another object of the present invention to provide the device as defined above, wherein said flowable substance comprises a medicament.

It is another object of the present invention to provide the device as defined above, wherein said flowable substance is selected from a group consisting of a liquid, a powder, an aerosol, a slurry, a gel, a suspension and any combination thereof.

It is another object of the present invention to provide the device as defined above, wherein said charging mechanism is a piston driven by moving a handle.

It is another object of the present invention to provide the device as defined above, wherein said charging mechanism is pressurized gas, contained within an enclosure adapted to enclose pressurized gas.

It is another object of the present invention to provide the device as defined above, wherein said flowable substance is contained within a flowable substance container emplaceable within said two-step mechanism.

It is another object of the present invention to provide the device as defined above, wherein said charging mechanism comprises a piston sealingly contained in a shaft, said piston flexibly connected to a handle, said handle characterized by at least two configurations: a retracted position and an extended position, said shaft fluidly connected to an air-tight enclosure.

It is another object of the present invention to provide the device as defined above, wherein said shaft comprises said air-tight enclosure.

It is another object of the present invention to provide the device as defined above, wherein said charging mechanism comprises a pressurized gas enclosure adapted to enclose pressurized gas, said pressurized gas enclosure in fluid connection with said nosepiece.

It is another object of the present invention to provide the device as defined above, wherein said nosepiece is adapted to be removably emplaced within a nostril, in a manner selected from a group consisting of sealingly emplaced within a nostril, sealingly emplaced against the opening of the nostril, loosely emplaced within a nostril, loosely emplaced against the opening of the nostril.

It is another object of the present invention to provide the device as defined above, wherein said charging mechanism comprises a filter, said filter adapted to remove from the gas at least one selected from a group consisting of particulates, bacteria, viruses, moisture, and undesired particles.

It is another object of the present invention to provide the device as defined above, wherein said flowable substance container adapted to contain said flowable substance (flowable substance capsule) is adapted to be removably emplaceable within said device.

It is another object of the present invention to provide the device as defined above, wherein said charging mechanism is characterized by three positions, a first position wherein said charging mechanism is retracted, a second position wherein said charging mechanism is partly extended, said capsule is lockable in position and charging is initiatable, and a third position wherein said charging mechanism is fully extended and said capsule is insertable.

It is another object of the present invention to provide the device as defined above, wherein said flowable substance capsule is removable from said device when said charging mechanism is in the fully extended position.

It is another object of the present invention to provide the device as defined above, wherein said flowable substance capsule is not removable from said device when said charging mechanism is not in said fully extended position.

It is another object of the present invention to provide the device as defined above, wherein said charging mechanism is adapted to open said flowable substance capsule.

It is another object of the present invention to provide the device as defined above, wherein said charging mechanism is adapted to open said flowable substance capsule during at least some portion of the time during which said charging mechanism is transformed from said extended position to said retracted position.

It is another object of the present invention to provide the device as defined above, wherein said charging mechanism is adapted to open said flowable substance capsule at the beginning of the time during which said charging mechanism is transformed from said extended position to said retracted position.

It is another object of the present invention to provide the device as defined above, wherein the means to open said flowable substance capsule is independent of said charging mechanism.

It is another object of the present invention to provide the device as defined above, wherein the means to open said flowable substance capsule is selected from a rod, a spear, a needle, a knife, a peel-off portion attached to said flowable substance capsule, and any combination thereof.

It is another object of the present invention to provide the device as defined above, wherein at least a portion of said nosepiece is removable from said device.

It is another object of the present invention to provide the device as defined above, wherein said nosepiece and said flowable substance capsule form a single unit.

It is another object of the present invention to provide the device as defined above, wherein said flowable substance capsule contains a single dose of said flowable substance.

It is another object of the present invention to provide the device as defined above, wherein said flowable substance capsule comprises a cartridge, said cartridge comprising a plurality of independently-openable containers, each said independently-openable container comprising (a) a single dose of said substance, (b) multiple doses of said substance, (c) different substances, (d) substance, (e) carrier and (f) any combination thereof.

It is another object of the present invention to provide the device as defined above, wherein said flowable substance capsule comprises a filter, said filter upstream of said substance, said filter adapted to remove from the gas at least one selected from a group consisting of particulates, bacteria, viruses, moisture, and undesired particles.

It is another object of the present invention to provide the device as defined above, wherein said device comprises a unidirectional valve such that gas is enabled to flow from the charging mechanism to the nostril, but is unable to flow in the reverse direction.

It is another object of the present invention to provide the device as defined above, wherein at least a portion of said mouthpiece is a member of a group consisting of removable, replaceable and any combination thereof.

It is another object of the present invention to provide the device as defined above, wherein said mouthpiece comprises an auxiliary air filter, said filter adapted to remove from gas passing through said filter at least one selected from a group consisting of particulates, bacteria, viruses, moisture, and undesired particles.

It is another object of the present invention to provide the device as defined above, wherein said mouthpiece is in fluid connection with a valve mechanism within said device such that suction on said mouthpiece opens said valve mechanism, thereby enabling flow of said pressurized and predetermined amount of compressed gas through said device.

It is another object of the present invention to provide the device as defined above, wherein said charging mechanism comprises a pump, said pump in fluid connection with a valve mechanism within said device such that suction on said mouthpiece opens said valve mechanism, thereby enabling flow of said pressurized and predetermined amount of compressed gas through said device.

It is another object of the present invention to provide the device as defined above, wherein said activation mechanism comprises a hollow flexible tegument, wherein compressing and releasing said tegument opens said valve mechanism, thereby enabling flow of said pressurized and predetermined amount of compressed gas through said device.

It is another object of the present invention to provide the device as defined above, wherein said activation mechanism comprises one of a group consisting of a compressible spring, a magnetic field, an electric field and a piezoelectric device, said activation mechanism activated by means selected from a group consisting of a releasable catch, a pressable button, a flippable switch, a rotatable knob and a movable lever, said activation mechanism opening said valve mechanism, thereby enabling flow of said pressurized and predetermined amount of compressed gas through said device.

It is another object of the present invention to provide the device as defined above, wherein said predetermined position of said pressurized and predetermined amount of compressed gas is an air-tight enclosure within said device, said air-tight enclosure charged when said charging mechanism is transformed from said extended position to said retracted position, said charging mechanism is adapted to pressurize external gas into said air-tight enclosure.

It is another object of the present invention to provide the device as defined above, wherein said predetermined position of said pressurized and predetermined amount of compressed gas is a pressurized gas enclosure adapted to enclose pressurized gas, said pressurized gas enclosure in fluid connection with said nosepiece.

It is another object of the present invention to provide the device as defined above, wherein said pressurized gas enclosure and said flowable substance capsule form a single unit.

It is another object of the present invention to provide the device as defined above, wherein said pressurized gas enclosure and said flowable substance capsule form separate units.

It is another object of the present invention to provide the device as defined above, wherein said pressurized gas enclosure comprises a plurality of compartments.

It is another object of the present invention to provide the device as defined above, wherein said flowable substance capsule comprises a plurality of compartments.

It is another object of the present invention to provide the device as defined above, wherein at least one said compartment contains a substance different from the substance in at least one other said compartment.

It is another object of the present invention to provide the device as defined above, wherein said device is adapted for a predetermined target population.

It is another object of the present invention to provide the device as defined above, wherein said predetermined target population is persons of limited physical strength.

It is another object of the present invention to provide the device as defined above, wherein said predetermined target population is persons with difficulties coordinating breathing with activation of said device.

It is another object of the present invention to provide the device as defined above, wherein delivery factors adapted to provide optimum delivery of said substance are selected from a group consisting of the length of time over which the delivery occurs, the gas speed in the nostril during delivery, the gas speed in the nostril during delivery of the gas with entrained substance, the volume of gas entering the nostril, the excess gas pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

It is another object of the present invention to provide the device as defined above, wherein either one of said nosepiece or said mouthpiece are rotatable around said main longitudinal axis.

It is another object of the present invention to provide the device as defined above, wherein either one of said nosepiece or said mouthpiece are rotatable around said main longitudinal axis.

It is another object of the present invention to provide the device as defined above, additionally comprising indicating means adapted to provide an indication the user if said entrain of said flowable substance within said enclosed air and transport the same from said container to said nasal passages has been successful.

It is another object of the present invention to provide the device as defined above, wherein said indication is visible by means of a change of color, audible by means of a predetermined sound pattern and any combination thereof.

It is another object of the present invention to provide the device as defined above, wherein said compressed gas, is inert and will not react with said substance.

It is another object of the present invention to provide the device as defined above, wherein said substance is a medicament selected from a group consisting of saline, natural substances, medicaments for treatments for allergic rhinitis, medicaments for treatments for osteoporosis, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists, antagonists, antitussives, medicaments for treatment of motor disorders, antiepileptics, antipsychotics (neuroleptics), sedative-hypnotics, anxiolytics, centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, antihistamine, Astelin, Otrivin, Livostin, Theramax, Avamys, Luffeel, Sinofresh, Nasonex, Nasocort, Veramyst, medicaments for treatment of osteoporosis, Miacalcin, Fortical, Stadol, medicaments for vaccinations and immunizations, Lavin, and influenza vaccines including FluMist, NasalFent. calcitonin, parathyroid hormone, neurotransmitters, neuromodulators, acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor and other growth factors), norepinephrine, nitric oxide, Substance P. alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, thiopental, benzocaine, bupivacaine, cocaine, lidocaine, prilocaine, procaine, ropivacaine, tetracaine, agonists, codeine, diphenoxylate, heroin, hydrocodone, 1-alpha-acetyl-methadol, levomethadyl acetate, loperamide, meperidine, methadone, oxycodone, d-propoxyphene, combinations of opioids plus acetaminophen and asa, tramadol, buprenorphine, butorphanol, nalbuphine, nalorphine, naloxone, naltrexone, nalmefene, pentazocine, codeine, dextromethorphan, hydrocodone, medicaments for treatment of Parkinson's disease and motor disorders, amantadine, apomorphine, baclofen, benzodiazepines, benztropine, bromocriptine, carbidopa, cyclobenzaprine, dantrolene, dopamine, entacapone, haloperidol, pergolide, pramiprexole, ropinerole, selegiline (L-deprenyl), trihexyphenidyl, rasagiline, Azilect, ladostigil, rotigotine, Neupro, mono amine oxidase inhibitor, COMT inhibitor, antiepileptics, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem skeletal muscle relaxants, alprazolam, chlorazepate, chlordiazepoxide, diazepam, flumazenil, lorazepam, oxazepam, amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, antischizophrenic drugs, anti depression drugs, Comtan, anti ADHD agents, anti ADHD drugs, Methylphenidrate (Ritalin), anti-autism and anti-autism symptoms drugs, medicaments for treatment of Alzheimer's disease, donepezil, galantamine, rivastigmine, tacrine, insulin, insulin detemir, Novolin, Humulin, insulin-like hormone, dopamine agonist, dopamine antagonist and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein FIGS. 1A-C schematically illustrate devices of prior art;

FIGS. 3-10 schematically illustrate one embodiment of the present invention;

FIG. 21 shows a comparison of deposition of liquid aerosolized dye between the present device and a commercially available device;

FIG. 22 illustrates a comparison of the present device with commercially available devices;

FIG. 28 shows closure of the velum during use of the present device;

FIGS. 31A-B show the location of deposition of material in the nasal passages of a rat after application with the present device;

FIGS. 32-34 illustrate the location of deposition of material in the nasal passages and brain of rats after application with the present device;

FIG. 37 shows the location of deposition of material in the rat after application via I/V;

FIG. 38 shows the location of deposition of material in the rat after application via the present device;

DETAILED DESCRIPTION OF THE PREFERRED EMBODIMENTS

Figure 1A:
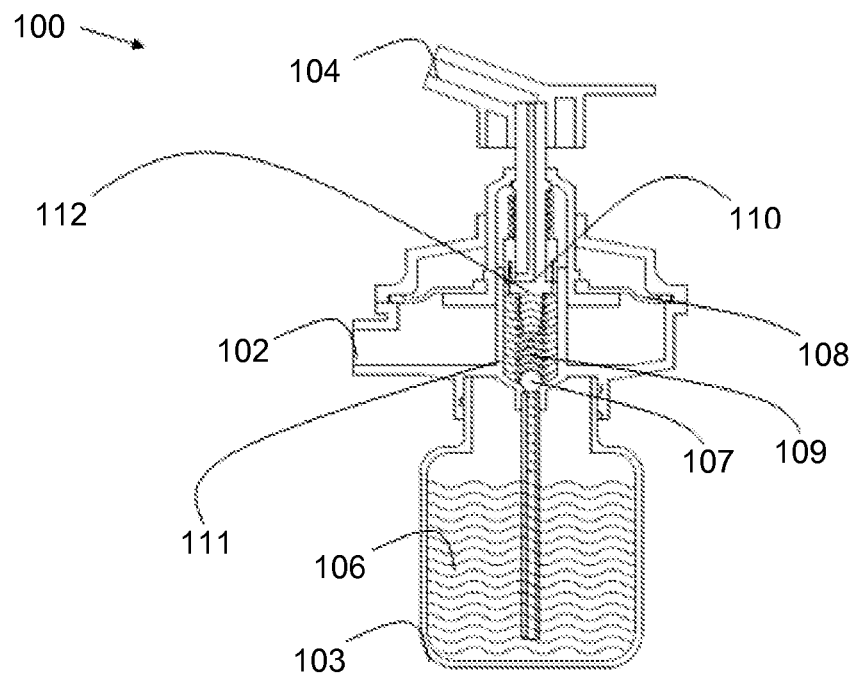

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for delivering substances to the nasal cavities. More specifically the present invention relates to the use of compressed air (or any other gas) to carry/entrain flowable substance to the nasal passages. Thus, the present invention uses the energy stored in the compressed air or other gas as a carrier to deliver the medicament to the nasal cavity.

One of the main objects of the present invention is the ability to provide a device which delivers accurate, constant and reproducible medicament doses.

Furthermore, one of the advantages of the device of the present invention is the use of compressed air which enables better deposition and dispersion of the substance (e.g., medicament) in the nasal cavity to the area of interest.

According to one embodiment of the present invention, the volume of air used is in the range of about 5-50 ml and will be compressed to about 1.5-10 bar.

More specifically the present invention relates to the use of compressed air to carry/entrain flowable substance to the nasal passages. Thus, the present invention uses the energy stored in compressed air or gas as a carrier to deliver medicament to the nasal cavity. Furthermore, the volume of the air being compressed is in the range of the nasal cavity volume. Said volume serves as a carrier of a medicament for better dispersion and more targeted deposition in the nasal cavity.

Another advantage of the present invention is, as disclosed above, the use of a constant, accurate and large volume of air (in the volume range of the nasal cavity). Therefore, as will be described hereinafter, the activation of the device (the 'activation mechanism, e.g., suction, voice, mechanical) is merely to trigger the operation of the device (i.e., initiate the flow of substance in the device towards the nasal cavity). Thus, in the e.g., suction activation, the application of suction or others as above from the user will trigger either (a) the withdrawal of a constant volume of external air into the device to entrain the substance to the nasal cavity; or (b) enables the delivery of predetermined amount of compressed air (already enclosed within the device) to entrain the substance to the nasal cavity. The air volume and the compressed air pressure are predetermined thus allow maximal reproducibility in terms of amount of drug released into the nasal cavity, volume of aerosol, aerosol droplets size and the velocity of droplets.

Thus, according to a preferred embodiment of the present invention, both the pressure to which the gas/air (i.e., the carrier entraining the substance) is compressed and the volume of said gas/sir can be fined tuned and tailored to fit the delivery destination (e.g., respiratory epithelium, olfactory epithelium, brain, lungs, pharynx, heart and any combination thereof).

One of the advantages of the device of the present invention is the fact that the carrier of the substance (e.g., medicament)—i.e., the compressed air or gas, is inert and will not react with the substance.

Another advantage of the device of the present invention is the fact that the ratio of carrier (i.e., compressed air or gas) and substance is relatively high.

It should be pointed out that the substance (e.g., medicament) is delivered to nasal passages so as to be delivered to at least one selected from a group consisting of respiratory epithelium, olfactory epithelium, brain, lungs, pharynx, heart and any combination thereof through the nasal passages.

The core concept of the present invention is the use of compressed air to entrain a substance and deliver the same through the nasal cavity so as to be delivered to at least one selected from a group consisting of respiratory epithelium, olfactory epithelium, brain, lungs, pharynx, heart and any combination thereof through the nasal passages. According to one embodiment, the substance is delivered to the middle and upper turbinates, from whence it can cross, via the thin ethmoid bone, into the brain, thus bypassing the blood/brain barrier and efficiently delivering substances, especially medicaments, to the brain.

The term 'capsule' hereinafter refers to a container adapted to contain a flowable substance. The term flowable refers hereinafter to any liquids, gas, aerosol, powders and any combination thereof substances. The term will also be referred hereinafter as flowable substance capsule.

The term 'plurality' hereinafter refers to an integer greater than or equal to one.

The term 'olfactory epithelium' hereinafter refers to a specialized epithelial tissue inside the nasal cavity. The olfactory epithelium lies on the upper top portion of the nasal cavity behind the nostrils.

The term 'flowable substance' hereinafter refers to any substance capable of flowing, such a substance can be a granular material, including a powder; a liquid; a gel; a slurry; a suspension; and any combination thereof.

The term 'gas' refers to any fluid that can be readily compressed. Gases as used herein include, but are not limited to, air, nitrogen, oxygen, carbon dioxide, helium, neon and xenon. Devices charged by hand will normally use air as the carrier gas. Preferred gases for use with compressed-gas charging are air, nitrogen and carbon dioxide.

The term 'about' refers hereinafter to a range of 25% below or above the referred value. The present device will be referred to hereinafter as SipNose.

In FIGS. 3-17, like numbers indicate like parts.

Figure 1B:
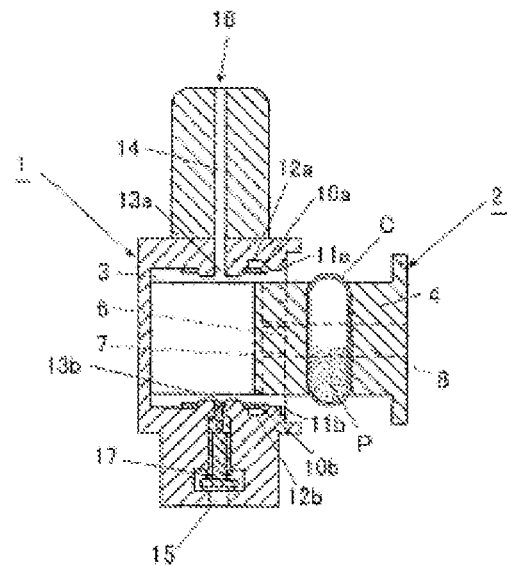
Figure 1C:
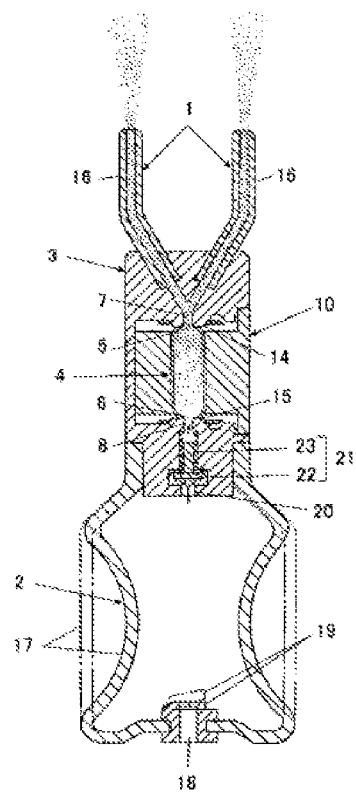

FIGS. 1A-C illustrate devices of prior art, discussed in detail hereinbelow, intended to deliver medicaments to the nasal passages.

The device of the present invention is intended to deliver substances to the nasal passages, especially the central and upper sections thereof, such as the middle and upper turbinates (FIGS. 2, 220 and 230), rather than to the lower turbinates (240). It is also intended especially to deliver drugs to the brain, as receptors in the middle and upper turbinates can deliver medicaments across the thin ethmoid bone (250) separating the nasal passages from the brain, bypassing the blood-brain barrier and allowing the passage of large or hydrophilic molecules that are unable to pass into the cerebrospinal fluid via the blood. The nasal route also enables delivery to the brain of substances that would otherwise be degraded by the digestive system and first pass metabolism in the liver if administered by the oral route.

Most devices of the prior art deliver a low volume of air, significantly lower than the volume of the nostrils. In the present device, the deliverable volume of air is limited only by the size of the charging chamber and, in practice can be on the order of the volume of the nostrils and can approach the volume of the nasal passages. Furthermore, while in the prior art device, the amount of suction applied by the user is the barrier for the amount of air entering the device, in the present device, the suction (or any other activating mechanism) is merely to enable the triggering of withdrawal of compressed air into the device. The amount (i.e., the volume) of compressed air does not depend on the amount of suction applied to the device by the user.

Another advantage of the present device is that using the mouthpiece for activation ensures that the mouth is closed during dosing. This increases the air pressure achievable in the nasal passages since no air can "leak out" through an open mouth. Furthermore, the suction necessary to activate embodiments of the device reduces the volume of air entering the patient's system by separating the mouth from the nasal passages and the lungs, thereby improving uptake.

The device of the present invention can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

Thus, according to one embodiment of the present invention, the use of compressed air to entrain the flowable substance enables delivery the substance to the olfactory epithelium and from there to the brain.

A further advantage of most embodiments of the device of the present invention is that the carrier that delivers the substance to the inside of the nostril is air; no further carrier is needed.

Therefore, application can be in powder form, in liquid form or in any other formulation known in the art. The substance can be stored in its most convenient form, either as a liquid, an aerosol, a powder, a slurry, a suspension, or a gel, if thin enough. The substance can be stored either with or without a carrier; the carrier can be a liquid, a gas or a powder. Preferably, the substance is stored without carrier; however, in some embodiments, the substance is stored in a carrier. If stored with a carrier, the carrier can be a gas, a liquid or a particulate powder.

It can be packaged to minimize degradation, for example, by packaging it in vacuum or under an inert atmosphere. In most embodiments, the substance to be delivered will be stored in single-use containers such as, but not limited to, blister packs so that a single, controllable dose can be delivered with each use of the device.

The substance as delivered can comprise a powder, a mixture of liquid and powder, a mixture of gas and powder, a mixture of powders, a liquid, a mixture of liquid and gas, a mixture of liquids, a gas, or a mixture of gases.

Use of an inert gas for the carrier for delivery of the medication obviates the possibility of interactions between the user and the delivery carrier; allergies to carriers, especially in medications used for chronic illnesses, is a growing problem. Furthermore, the delivery carrier is in contact with the medicament for no more than a few seconds and more commonly for no more than a few milliseconds, thereby minimizing degradation of the medicament due to interactions with the delivery carrier.

A further advantage of embodiments where the substance is stored without carrier is that the volume and weight of the substance will be small, enabling easier and more convenient storage and easier and more convenient use.

The delivery carrier is commonly a gas. Devices charged by hand will normally use air as the carrier gas. Preferred gases for use with compressed-gas charging are air, nitrogen and carbon dioxide.

When medicaments are stored in a liquid carrier, such as those used in metered dose inhalers, the formulation as stored is on the order of 99% carrier; a given number of doses of a medicament in a formulation without carrier, such as a formulation stored in blister packs, occupies only about 1% of the volume that the same number of doses of the same medicament occupies if the formulation includes a carrier, such as a formulation intended for use in a metered dose inhaler canister.

In most embodiments, the substance will be a medicament.

Examples of types of drugs and materials to be delivered to or through the nose are, but not limited to: treatments for allergic rhinitis; treatments for osteoporosis; vaccinations and immunizations; sexual dysfunction drugs; treatments for B12 deficiency; smoking cessation; treatment of gynecological problems; treatment of other women's health issues; general anesthetics; local anesthetics; opioid analgesics; agonist-antagonists and antagonists; antitussives; drugs used in the treatment of motor disorders; antiepileptics; drugs used in affective disorders; antipsychotics (neuroleptics); sedative-hypnotics, anxiolytics, and centrally acting muscle relaxants; treatments for anxiety disorders; skeletal muscle relaxants; treatments for Parkinson's disease; treatments for Alzheimer's disease;

Medicaments for treatment of allergic rhinitis include, but are not limited to: steroids, including corticosteroids, Flonase®, Patanase®, Beconase®, antihistamine, Astelin, Otrivin®, Livostin®, Theramax®, Avamys®, Luffeel®, Sinofresh®, Nasonex®, Nasocort® and Veramyst®.

Medicaments for treatment of osteoporosis include, but are not limited to, Miacalcin®, Fortical® and Stadol®.

Medicaments for vaccinations and immunizations include, but are not limited to: Lavin, and influenza vaccines including FluMist®.

Medicaments for smoking cessation include, but are not limited to: NasalFent.

Other medicaments which can be delivered include, but are not limited to, calcitonin and parathyroid hormone.

Neurotransmitters and neuromodulators that can be delivered include, but are not limited to: acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex®, Migranal®, zolmitriptan, Zomig®, Gamma-aminobutyric acid (GABA), glutamate (glu), glycine, histamine, leptin, nerve growth factor and other growth factors), norepinephrine, nitric oxide, and Substance P.

General anesthetics which can be delivered include, but are not limited to: alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze®, and thiopental.

Local anesthetics which can be delivered include, but are not limited to: benzocaine, bupivacaine, cocaine, lidocaine, prilocaine, procaine, ropivacaine, and tetracaine.

Opioid analgesics, agonist-antagonists, and antitussives which can be delivered include, but are not limited to: agonists, codeine, diphenoxylate, fentanyl, heroin and other opioids, hydrocodone, 1-alpha-acetyl-methadol, levomethadyl acetate, loperamide, meperidine, methadone, morphine, oxycodone, d-propoxyphene, combinations of opioids plus acetaminophen and asa, and tramadol.

Agonist/antagonists and antagonists which can be delivered include, but are not limited to: buprenorphine, butorphanol, nalbuphine, nalorphine, naloxone, naltrexone, nalmefene, pentazocine, codeine, dextromethorphan, and hydrocodone.

Drugs used in the treatment of Parkinson's disease and motor disorders which can be delivered include, but are not limited to: amantadine, apomorphine, baclofen, benzodiazepines, benztropine, bromocriptine, carbidopa, cyclobenzaprine, dantrolene, dopamine, entacapone, haloperidol, L-DOPA, pergolide, pramiprexole, ropinerole, selegiline (L-deprenyl), trihexyphenidyl, rasagiline, Azilect®, ladostigil, rotigotine, Neupro®, mono amine oxidase inhibitor, and COMT inhibitor.

Antiepileptics which can be delivered include, but are not limited to: acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin and midazolam.

Drugs used in affective disorders which can be delivered include, but are not limited to: antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate and valproic acid.

Antipsychotics (neuroleptics) which can be delivered include, but are not limited to: chlorpromazine (CPZ), clozapine, fluphenazine, haloperidol, olanzapine, quetiapine, risperidone, sertindole, thioridazine, thiothixene and ziprasidone.

Sedative-hypnotics, anxiolytics, and centrally acting muscle relaxants which can be delivered include, but are not limited to: alprazolam, chloral hydrate, diphenhydramine, flumazenil, flurazepam, hydroxyzine, lorazepam, oxazepam, phenobarbital, temazepam, triazolam, zaleplon and zolpidem.

Anxiety disorders and skeletal muscle relaxants which can be delivered include, but are not limited to: alprazolam, chlorazepate, chlordiazepoxide, diazepam, flumazenil (antagonist), lorazepam, and oxazepam.

Other drugs which can be delivered include, but are not limited to: amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan®, entacapone, anti ADHD agents, anti ADHD drugs such as Methylphenidrate (Ritalin®), and anti-autism and anti-autism symptoms drugs.

Treatment of Alzheimer's disease which can be delivered include, but are not limited to: donepezil, galantamine, rivastigmine, tacrine, insulin, insulin detemir, Novolin®, Humulin®, insulin-like hormone, dopamine agonist and dopamine antagonist.

FIGS. 1A-C illustrates a device of prior art. In the device of prior art in FIG. 1A 100, the device comprises a nose piece 104 (to be placed within the nasal cavity of the patient), a mouth piece 102 (to be placed within the mouth of the patient), and a container 103 for accommodating the flowable substance 106 to be delivered to the nasal cavity of the patient. The actuation mechanism (for activating the device and delivering flowable substance to the patient's nasal passages) comprises a first unidirectional valve 107, a membrane 108, an intermediate compartment 111 (for accommodating a unit dose amount of flowable substance to be delivered to the patient's nasal passages), at least one spring 109 and a second valve means 110.

Prior to the actuation of device 100, the unidirectional valve 107 enables the filling of intermediate compartment 111 with the unit dose amount of flowable substance 106. This is enabled due to the fact that after said flowable substance is released to the nasal passages, vacuum is created in said intermediate compartment 111, which 'draws' said flowable substance 106 through unidirectional valve 107.

In the device of prior art in FIG. 1B, a capsule holder 2 is adapted to hold capsule C. The capsule holder comprises cutting blades 10A, 10B for cutting both ends of the capsule C. Plate 4 in capsule holder 2 slidably holds capsule C in the longitudinal direction. Groove 8 slidably engages plate 4 for sliding capsule holder 2 in and out of body 1. Protrusions 6 and 7 are stops for the capsule holder 2 and the plate 4. Positioning guides 11A and 11B ensure that capsule C is properly positioned for cutting blades 10A and 10B. Pockets 12A and 2B are adapted to hold the cut-off ends of capsule C. The body 1 comprises two air passages, where 15 is the entrance and 13B the exit to one air passage and 16 is the entrance and 13A the exit to air passage 16. The lower air passage comprises valve 17.

In use, a capsule is placed in capsule holder 2 and capsule holder 2 is pushed into space 3, with blades 10A and 10B removing the ends of capsule C during the process. The user then places the protrusion comprising air passage 14 in the mouth and sucks on it. This raises valve 17; air enters the device through entrance 15, passes around valve 17, held open by the user's suction pressure, and through capsule C. In capsule C, the air entrains the medicament. The air then passes through air passage 14, through exit 16 and into the mouth. Clearly, and unlike the present device, the air speed during use, the air pressure and the volume of air generated are highly dependent on the characteristics of the user, which are not even consistent for a given user, let alone being consistent for different users.

FIG. 1C illustrates another device of the prior art, wherein an elastic-walled section of the device, the "pump" 2 is compressed to deliver the air through air passage 20, through capsule 4, air passages 1 and into the nostrils.

The volume of air delivered by this device is more consistent than the volume of air delivered in the device of FIG. 1B, since it will be, in practice, a relatively consistent fraction of the volume of the pump, the fraction depending on the strength of the user and the physical properties of the elastic walls of the pump. Similarly, the air pressure delivering the air to the nostril and the air speed will be more consistent than FIG. 1B, as they also depend on the strength of the user and the physical properties of the pump. However, the device of FIG. 1C differs from the present device in that, in the present device, none of the air speed, air volume or air pressure depends on the abilities of the user. Thus, for example, the volume of compressed air in the present device is fixed and constant regardless of the amount of suction (or any other activation) the user applies on the device. In the same manner, the amount of pressure applied on the compressed air does not, again, depend on the abilities of the user.

In addition, unlike the present device, the length of time over which the dose is delivered in the device of FIG. 1C depends on how fast the user squeezes the pump. In the present device, the length of time over which the dose is delivered depends solely on the physical properties, such as shape and size, of the interior of the device.

Furthermore, the device of FIG. 1C is a one-step device—the user compresses the pump and the contents of the capsule are delivered. The present device is a two-step device, where the air chamber (the closest equivalent of the pump 2 in FIG. 1C) is charged with a fixed volume of air during a charging step. In an activation step, a valve is opened, the capsule is opened, and the contents of the air chamber are delivered to the nostril, ensuring that air pressure, air speed, air volume and time of delivery are completely consistent between doses.

Figure 2:
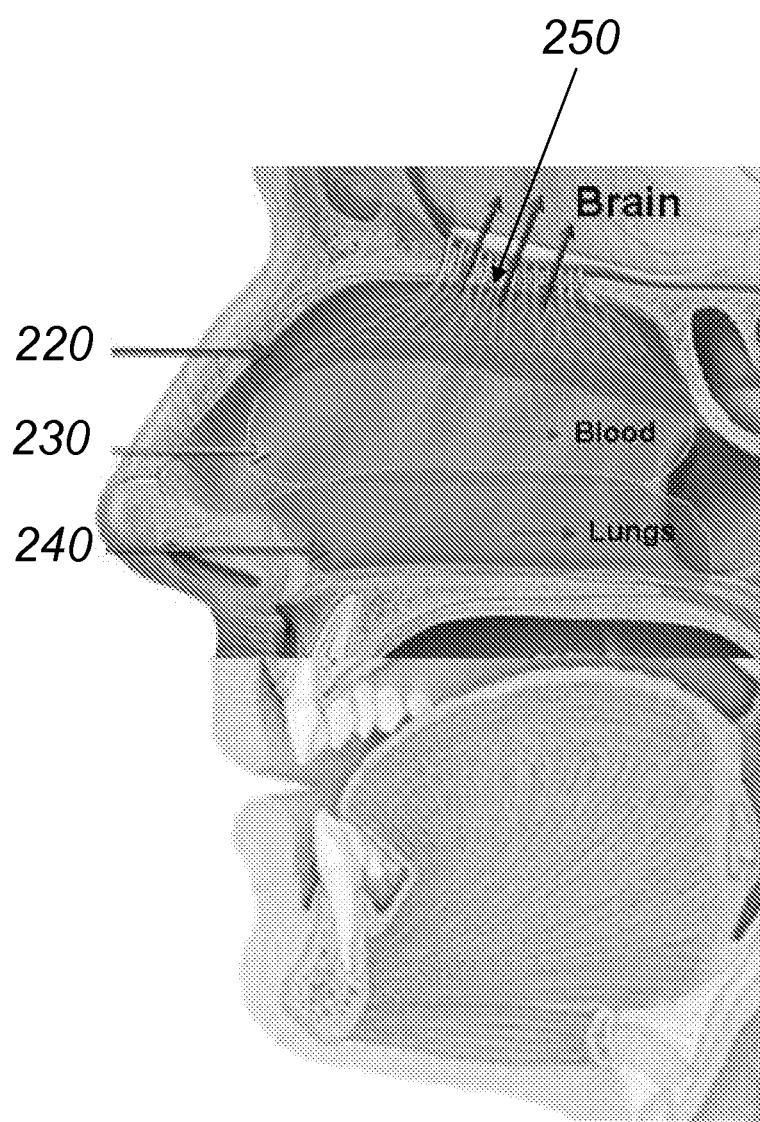
FIG. 2 schematically illustrates locations for deposition of substances entering the nostrils.

FIG. 2 illustrates locations for deposition of substances entering the nostrils. Typical locations are deposition in the lungs after passage through the lower turbinates (240), thereby enabling transfer of the substance across the walls of the alveoli of the lungs; deposition in the mucous membranes lining the nasal passages, especially the lower (240), middle (230) and upper (220) turbinates, facilitating transfer of the substance to the blood; and deposition in the olfactory mucous membranes of the upper turbinates (220) facilitating transfer, via the thin ethmoid bone (not shown) to the brain.

In the device of the present invention, delivery of the substance to the nasal passages is a two step process. In the first step, as described hereinbelow, the device is charged and, in the second step, described hereinbelow, the device is activated so that the substance is delivered to the nostrils.

Figure 3A:
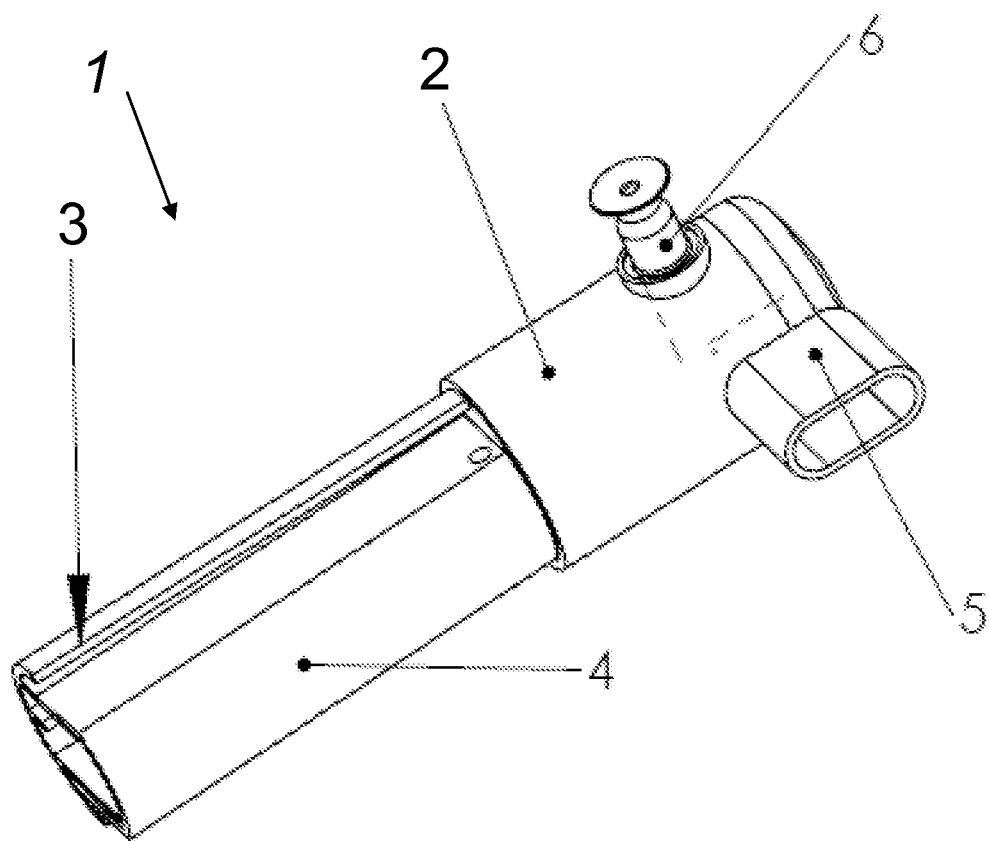
Figure 3B:
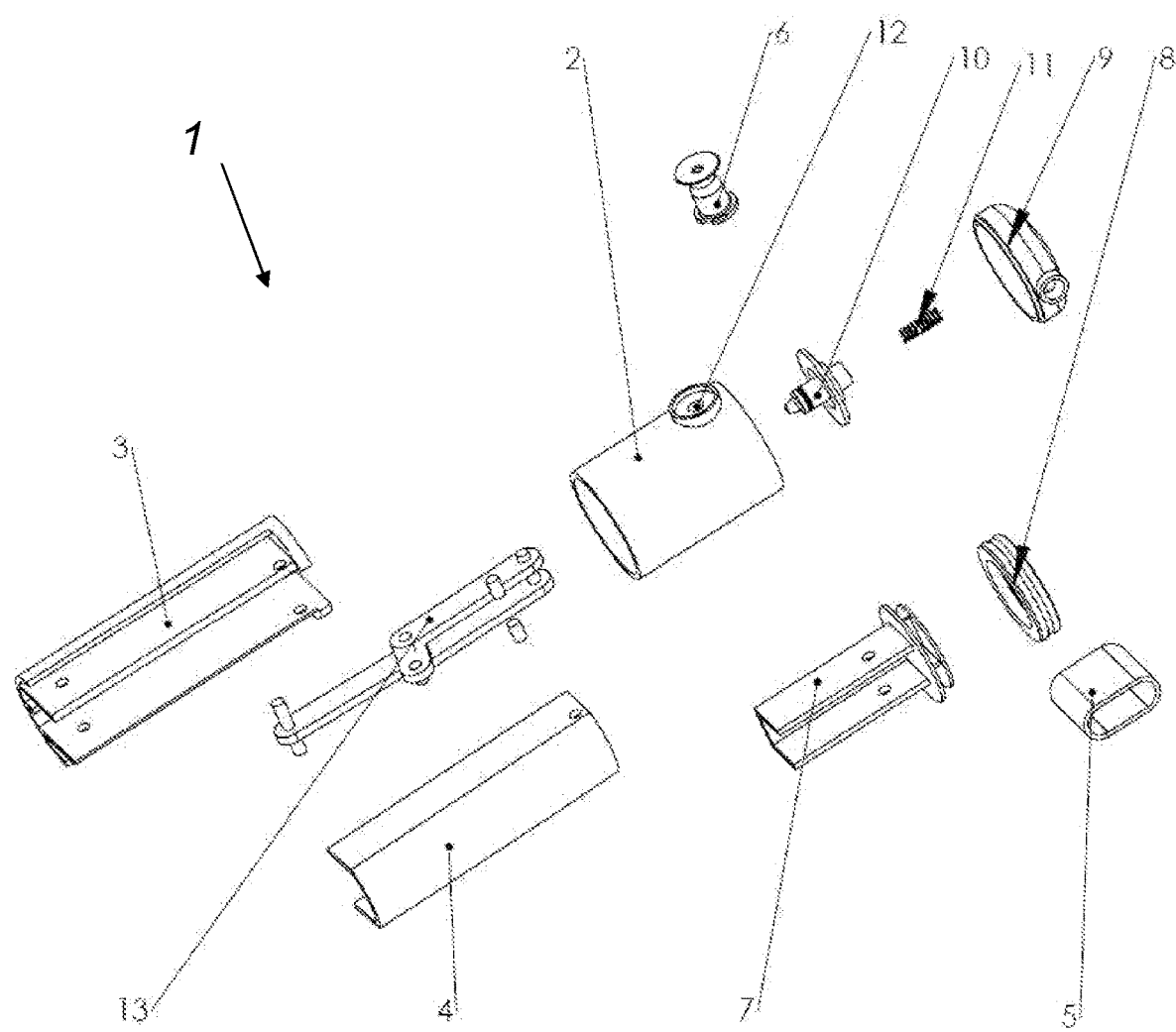

FIG. 3 illustrates an embodiment (1) of the present invention. FIG. 3A illustrates the device assembled, while an exploded view is presented in FIG. 3B. The device comprises a proximal end with a fixed part (3) and a handle (4) mounted to the fixed part, the handle enabled to pivot about a pivoting means (not shown) at the upper end. The proximal end is fixedly connected to the distal end, comprising an air-tight enclosure (2). At the distal end, mounted on one side of the air-tight enclosure (2) is a nosepiece (6) enabling dispensing of the flowable substance into a nostril, and a mouthpiece (5) enabling firing (i.e., activation) of the device. The mouthpiece (5) is rotatable at least about the air-tight enclosure, and, in some embodiments, is also rotatable about an axis perpendicular to the air-tight enclosure and passing through the mouthpiece, thereby enabling the mouthpiece to be aligned with the mouth and the nosepiece to be aligned with the nostril, enabling the user to comfortably insert the nosepiece into either nostril and allowing a better fit of the device to a variety of users.

The piston travels within a shaft; in most embodiments, the air-tight enclosure (2) forms the shaft within which the piston travels.

FIG. 3B illustrates the device in an exploded view. The piston driver (13), which, in this embodiment, is hinged in the middle, is connected at its bottom end to the fixed part of the proximal end (3) and, in the middle, to the handle (4) such that, when the handle is squeezed, the upper end of the piston driver (13) is driven upward into the air-tight enclosure (2), which is closed by a cap (9), rotatable about the air-tight enclosure (2). The upper end of the piston driver (13) is rotatably fixed to a piston (7 and 8), which fits snugly, sealingly and slidably into the air-tight enclosure (2). The piston comprises a base (7) and a sealing ring (8), the sealing ring (8) ensuring that air does not pass from one side of the sealing ring to the other. Slidably mounted between the top of the piston (7) and the cap (9) is an air-flow regulator (10), which is held against the top of the piston (7) by a spring (11). Mouthpiece (5) is rotatable towards and away from the nosepiece (6) so as to be adjustable to different mouth-nose distances of different patients.

FIG. 4A illustrates a side view of the device, with the nosepiece (6) visible on the left and the mouthpiece (5) at the front of the enclosure (2). FIG. 4B illustrates a cross-section of the assembled device along line A-A of FIG. 4A, including the distal end of the device and part of the proximal end. FIG. 4B illustrates the assembled device with the handle (4) extended, preparatory to preparing to deliver the substance to the user. The piston (7 and 8) is at the bottom of the enclosure section of the device, with the sealing ring (8) snugly, sealingly and slidably resting against the interior of the enclosure (2). The piston base (7) is slidably connected to the proximal end (3). The piston driver (13) is pivotally attached to the proximal end (3) at the bottom of the of the piston driver, pivotally attached to the handle (4) in the middle of the piston driver, and pivotally attached to the piston base (7) at the top of the piston driver. By this means, the piston driver is adapted to move the piston (7 and 8) towards the cap (upward in FIG. 4B) when the handle is closed. Closure of the handle (4) is indicated in FIG. 4B by the dashed arrow.

FIG. 4C illustrates a close-up view of the interior of the enclosure (2), indicated by the circle B in FIG. 4B, when the handle (not shown) is in the extended position. With the handle (not shown) in the extended position, the piston (7), with its sealing ring (8), is at the bottom of its travel. Above the piston is the air-flow regulator (10), pressed downward against a separator (40) by the spring (11). In this position, the air-flow regulator (10) fits snugly into an opening (14), and there is no fluid connection between the nosepiece air passage (lower air passage) (16), which is fluidly connected through the nosepiece (not shown) to the external air, and the piston air space. Suction on the mouthpiece enables the airflow regulator (10) to rise against the spring (11), enabling air trapped above the piston to flow through the air channel (14).

In FIGS. 4B and 4C, the piston (7) is shown at the bottom of its travel.

FIG. 5A illustrates a side view of the device, rotated 90° from the view in FIG. 4A, such that the mouthpiece (5) is now seen at the left side of the enclosure (2), with the nosepiece (not shown) behind the device. The proximal end (3) is seen at the left and the handle (4), in the retracted position, at the right. FIG. 5B illustrates a cross-section of the device along the line A-A in FIG. 5A, including the distal end of the device and part of the proximal end, with the nosepiece (6) at the left and the piston driver (13) in the lower center, with the handle (4) at lower right. FIG. 5C illustrates a close-up view of the interior of the enclosure (2), indicated by the circle B in FIG. 5B, when the handle (4) is in the retracted position. In FIG. 5C, suction through the mouthpiece (not shown) has forced the air-flow regulator (10) up against the spring (11), opening air channel 16, so that there is a fluid connection between air space above the piston (the piston chamber), the lower air passage (18), the bore of the nosepiece (6) and the external air. FIG. 5D illustrates a close-up view of the lower part of the air-flow regulator (10), indicated by the circle C in FIG. 5C.

In FIGS. 5B and 5C, the piston (7) is shown at the top of its travel.

When the valve mechanism (10) moves upward, air above the piston flows through air channel 16, through vestibule 17, lower air passage 18, through the flowable substance container (flowable substance capsule or capsule) (not shown), from thence through the bore of the nosepiece (5), and from thence into the nostril.

FIG. 6 illustrates the nosepiece (6). FIG. 6A illustrates a side view of the nosepiece (6), and FIG. 6B, a view of the end, from the outside. FIG. 6C illustrates a cross-section of the nosepiece (6), along the line A-A, including the distal end of the device and part of the proximal end. The nosepiece (6) has a cap (20) with a bore, providing a fluid connection between the nostril and substance container (25). The substance is preferably stored in the container (25) as a liquid or as a dry powder. Attached to the lower part of the body is the lower cap of the nosepiece (24), which is removed prior to application. The capsule base (22) is provided with means for piercing the flowable substance capsule (21). The inner capsule contains means (27) adapted to increase turbulence of the air on its way through and out of the capsule.

Figure 6A:
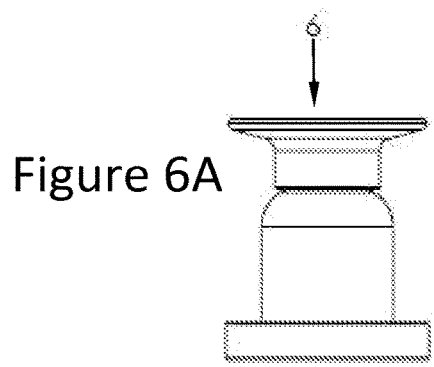
Figure 6B:
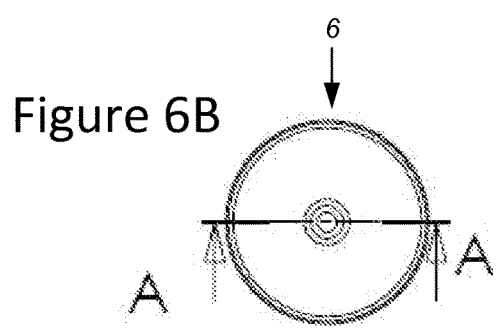
Figure 6C:
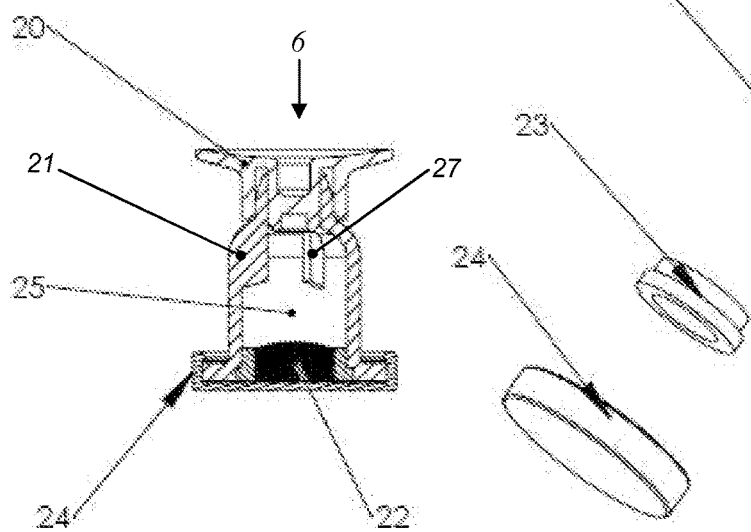
Figure 6D:
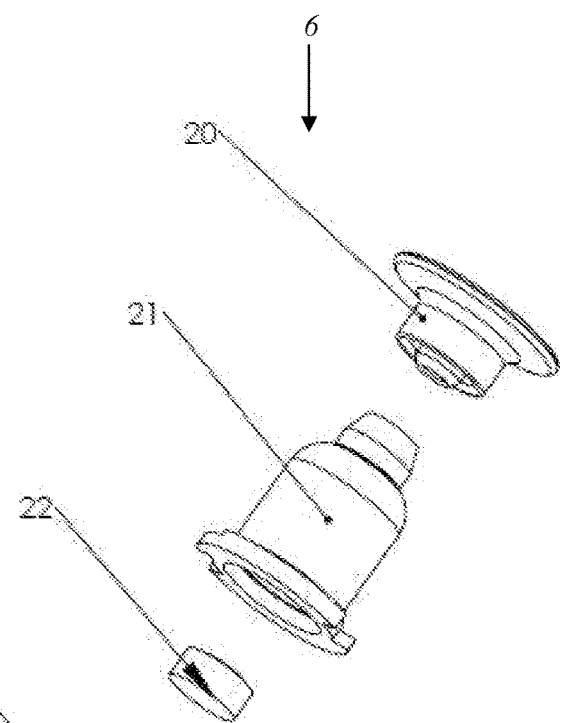

FIG. 6D illustrates an exploded view of the inlet. The nosepiece base (24) is attached to a flowable substance capsule holder (23), which holds the flowable substance capsule (21) snugly and removably. The flowable substance capsule (21) is adapted to be pierced while the capsule is adjusted to its activated position. On the flowable substance capsule (21) is mounted a cap (20) with a bore which fluidly connects the nosepiece interior air space with the exterior of the device.

Figure 7A:
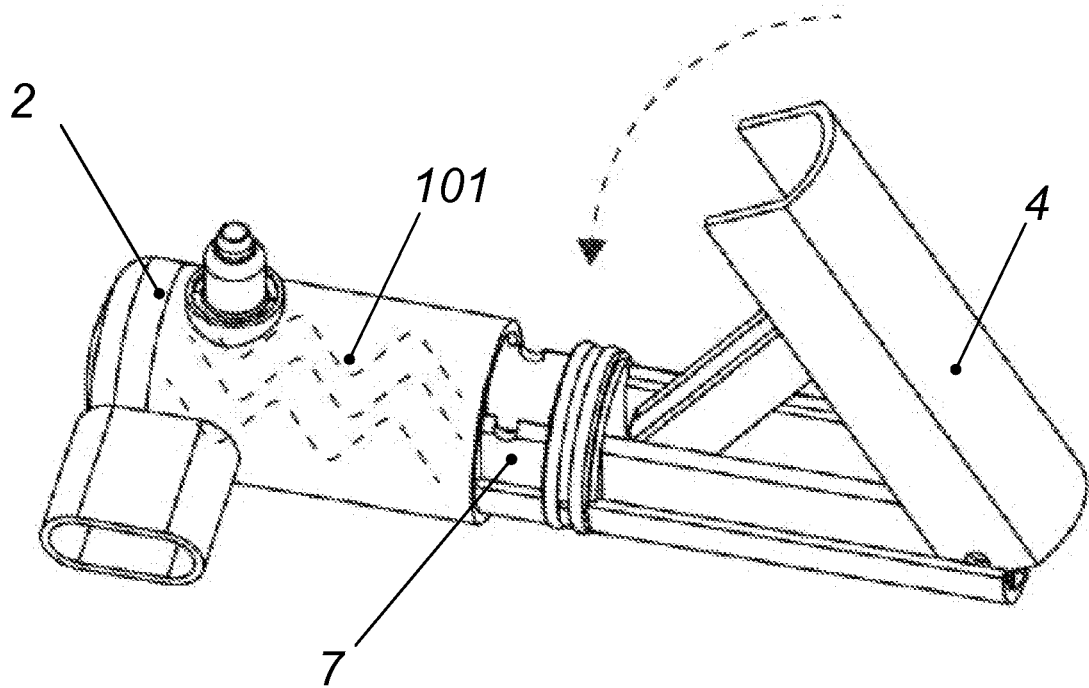
Figure 7B:
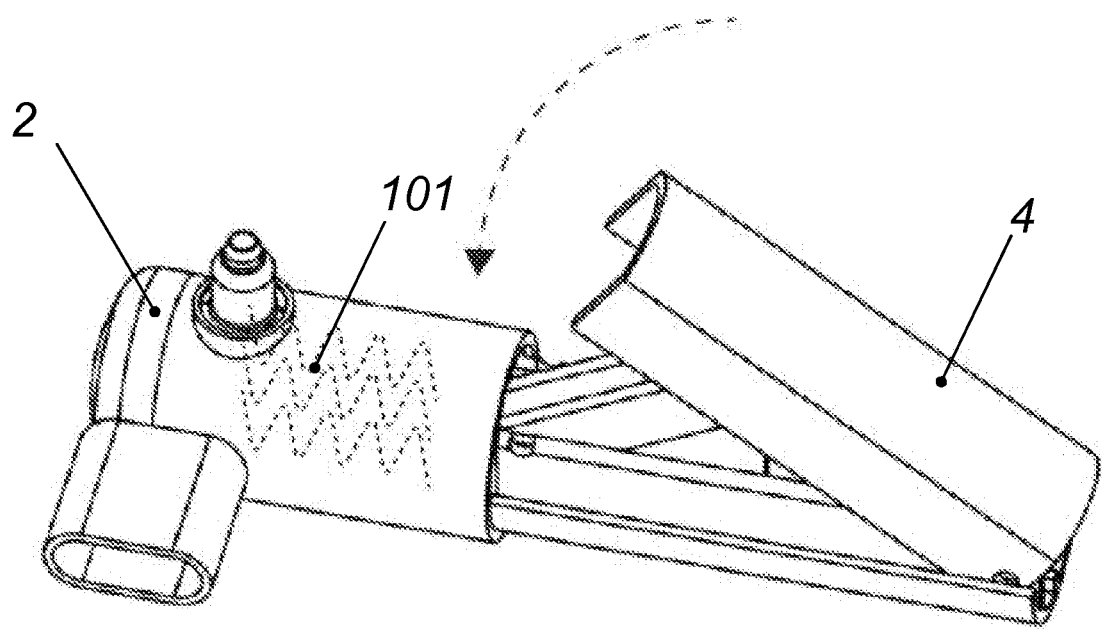
Figure 7C:
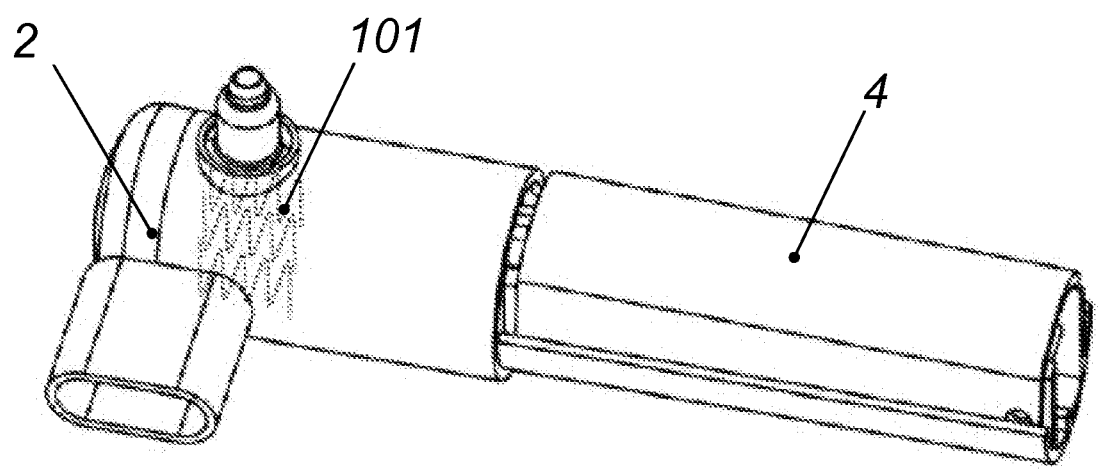

FIG. 7 illustrates charging the device. In FIG. 7A, charging is initiated by extending the handle (4), after opening of an air passage (not shown) in the handle which fluidly connects the space above the piston with the exterior air. After the handle (4) is in the fully extended position and air (101) has filled the chamber above the piston at near atmospheric pressure, the air passage is closed and a flowable substance capsule (21, not shown in the figure) is placed in the flowable substance capsule holder (23, not shown in the figure). As the handle (4) moves in the direction of the arrow, toward the retracted position (FIG. 7B), the air (101) is compressed. When the handle is in the fully retracted position (FIG. 7C), the air (101) has been fully compressed. In all embodiments of the present device, charging can be carried out at any speed, from sufficiently slowly to be considered as a quasi-static process to a fast process, without influencing the activation and performance of the device. An advantage of slow charging is that slow charging requires little strength in the user, thereby enabling the device to be used by persons with little strength, such as children or the frail elderly.

When the charging mechanism is retracted, it is in a first position, when partly extended, it is in a second position and, when fully extended, it is in a third position. In embodiments with three positions, when the device is in the fully-extended position, the medicament capsule can be inserted in the device. The charging mechanism can then be retracted to the second position, wherein the medicament capsule, if properly inserted, can be locked in place, thus enabling the user to ensure that the medicament capsule has been properly inserted. From the second position, the charging mechanism can be retracted to the retracted position, thereby charging the device.

In some embodiments, the device is fired by suction by the user on the mouthpiece (5), as described hereinbelow.

Figure 8A:
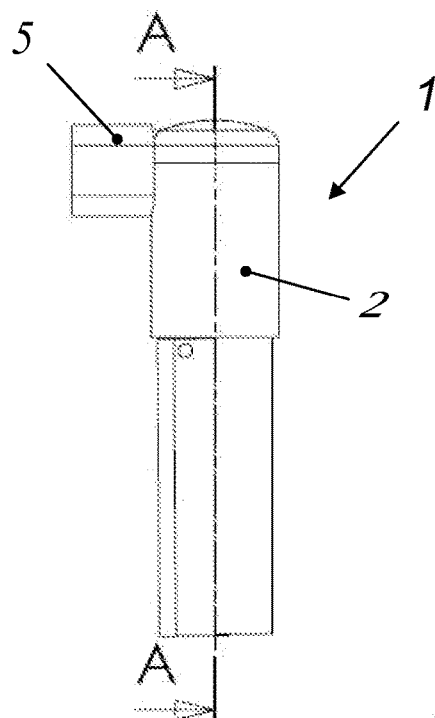
Figure 8B:
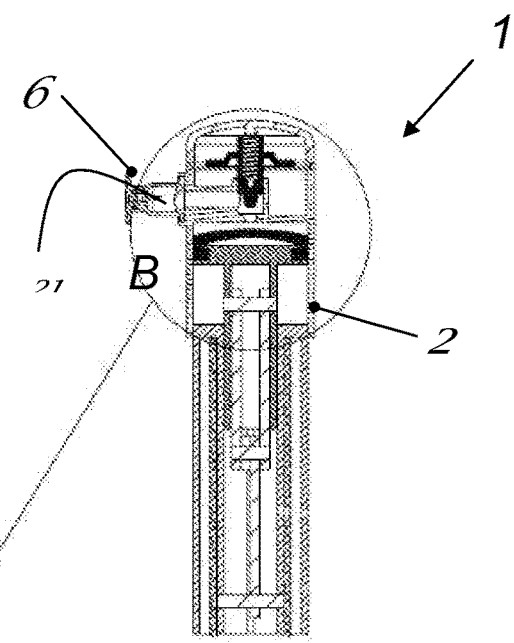
Figure 8C:
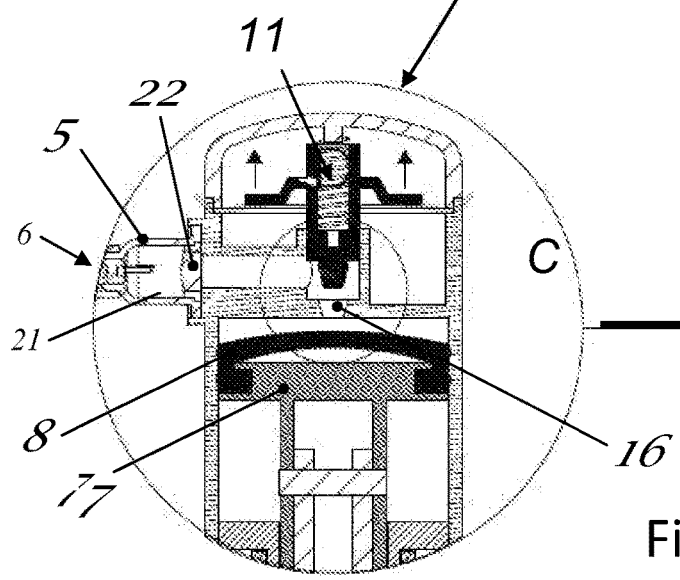
Figure 8D:
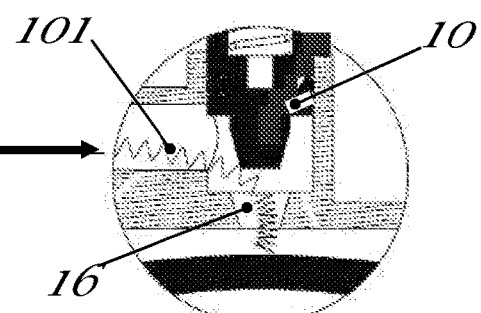
Figure 8E:
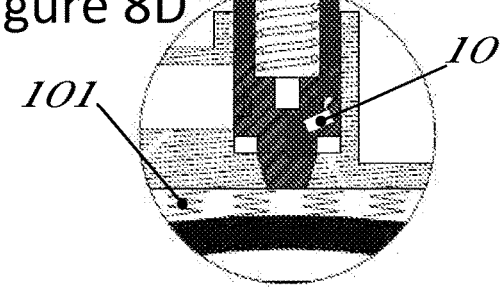

FIG. 8A illustrates another embodiment of the device in a position with the handle in the retracted position, showing the enclosure (2) and the mouthpiece (5). FIG. 8B illustrates a cross-section of the device along the line A-A, including the distal end of the device and part of the proximal end, while FIG. 8C illustrates a close-up of the circled area B in FIG. 8B, and FIG. 8D is a close-up of the circled area C in FIG. 8C. In FIGS. 9B and 9C, the device is shown with the valve mechanism (10, not illustrated in the figure) forced upward against the spring (11) by air pressure due to suction from the mouthpiece, enabling air flow through the air channel (16). FIG. 8D shows the region of the bottom of the valve mechanism (10) and the air channel (16), showing the path of the airflow (101) from the piston, through the lower air passage and towards the nosepiece (not shown). FIG. 8E shows the same region as FIG. 8D prior to the initiation of suction. Spring 11 (not shown) forces air regulator 10 down, sealing air channel 16 and preventing flow of air (101).

Also illustrated in FIGS. 8a-8c is the nosepiece capsule (21).

Figure 9A:
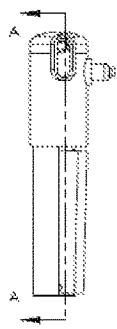
Figure 9B:
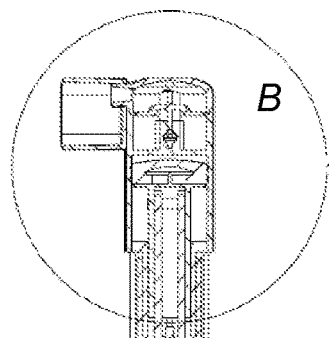
Figure 9C:
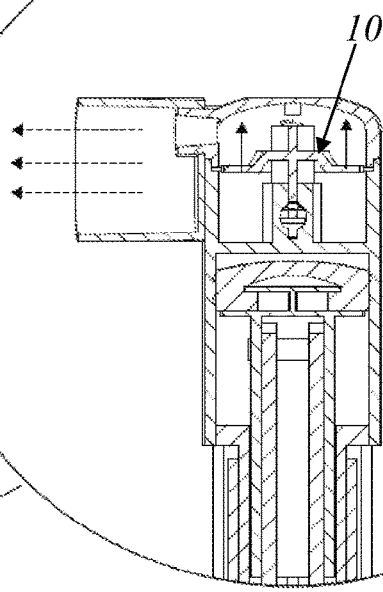

FIG. 9 illustrates suction on the device. The device (1) is illustrated in FIG. 9A, showing line A-A. FIG. 9B illustrates a cross-section along line A-A, including the distal end of the device and part of the proximal end. FIG. 9C illustrates a close-up of the region inside circle B in FIG. 9B. The broken arrows in FIG. 9C illustrate suction through the mouthpiece. This suction forces valve mechanism 10 upward (solid arrows), thereby enabling air flow through air channel 16 (not shown).

Figure 10:
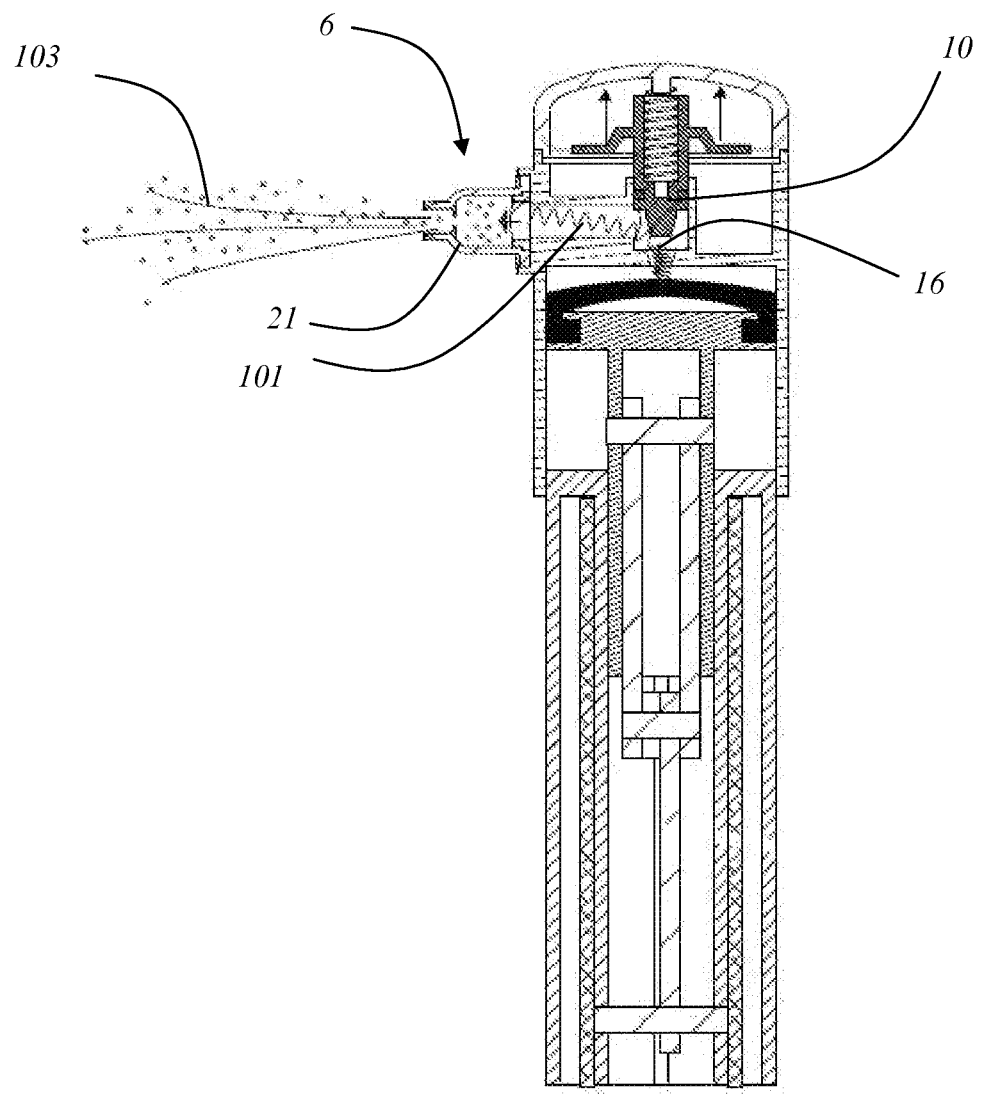

FIG. 10 illustrates the air flow through the device while suction is applied to the mouthpiece. Air (101, wavy lines) under pressure flows from the piston chamber through air channel 16, past valve mechanism 10, through flowable substance capsule 21, and through nosepiece 6, emerging into the nostril as an aerosolized mist (103).

Once air flow has been initiated by raising valve mechanism 10 and unsealing air channel 16, air flow through air channel 16 will keep air channel 16 open until the pressure in the piston chamber has been exhausted. Therefore, prolonged suction is not necessary to deliver the flowable substance to the nostril, only sufficient suction to open air channel 16, thereby enabling use of the device by persons such as severe asthmatics or persons with emphysema, who are unable to breathe in for prolonged periods of time.

In the preferred embodiment, firing of the device is enabled by suction on the mouthpiece as described hereinabove. In other embodiments, suction is provided by auxiliary means such as, but not limited to, a pump. In other embodiments, suction is provided by squeezing a hollow flexible tegument with a single opening, sealingly connecting said opening to the mouthpiece bore, and releasing the tegument such that suction is provided by air sucked into the tegument as it regains its unsqueezed shape. In other embodiments, valve mechanism 10 is raised by a means such as, but not limited to, a compressible spring, a magnetic field, an electric field or a piezoelectric device, said means activated by means such as, but not limited to, a pressable button, flippable switch, rotatable knob or movable lever. As an illustrative example, firing is accomplished by means of a spring, said spring attached at one end to the valve mechanism (1), and at the other end to the cap (9). The spring is held in the extended position by a catch. Pressing a button located on the enclosure releases the catch, whereupon the spring contracts and raises valve mechanism 10. In another illustrative example, a handle is attached to the top of valve mechanism 10, with a portion of the handle extending through the cap (9). Pulling up on the handle raises valve mechanism 10. Many other methods of raising valve mechanism 10 will be obvious to persons with ordinary skill in the art.

In all embodiments, the handle is designed so that the force needed to extend and retract the handle is sufficiently large that accidental activation is obviated, but sufficiently small that small children or weak adults can operate it. In the best embodiment, control of the charging force is provided by friction between the seal (8) and the enclosure (2). In other embodiments, friction between the upper and lower parts of the piston driver (13) enables control of the charging force. In yet other embodiments, the size of the air channel (16) enables control of the charging force. In yet other embodiments, a spring, elastic band or other elastic means attached to either the piston (7) or the piston driver (13) enables control of the charging force. In yet other embodiments, the charging force is adjustable, said adjustment controlled by a force adjustment means, as is well known in the art.

The device of the present invention has considerable flexibility, and can be manufactured in many variants, said variants tailored to provide optimal delivery of a flowable substance, said variants depending both on the flowable substance and the patient.

In the best embodiment, the device is tuned to provide the optimum delivery of the flowable substance, where optimum delivery includes, but is not limited to, such factors as ensuring that the dose is (1) delivered in its entirety to (2) the desired regions of the nose, while (3) causing the minimum of discomfort to the patient. Delivery factors that are tuned in order to adapt the device for the desired drug and the intended target population include, but are not limited to, the length of time over which the delivery occurs, the air speed at the nostril during delivery, the air speed in the region of the flowable substance during delivery, the volume of air entering the nostril, the excess air pressure at the nostril, the presence or absence of turbulence in the region of the flowable substance, the presence or absence of turbulence in the rest of the air channels within the device, the presence or absence of turbulence within the nasal passages.

Adaptations to the device which are adjustable to provide an optimum delivery of the desired drug to the target population include, but are not limited to, the size of the chamber, the strength of the spring, the strengths of any adjustable means, the diameter and length of the lower air chamber, the travel of the piston, frictional force between the piston seal (8) and the enclosure, the diameter of the air channel 16, and the diameters of the inlet and outlet openings.

Medicaments may be supplied as liquids, as powders, or as aerosols. In the preferred embodiment, the medicament is supplied in a single-dose capsule. In other embodiments, the medicament is supplied in a multi-dose containment means, the containment means adapted to provide a single dose per activation.

In another embodiment, the flowable-substance capsule has a plurality of compartments, each containing a different medicament, with the plurality of medicaments delivered to the nostril in a single dose. In this manner, a plurality of medicaments may be supplied to the nostril in a single injection, without interactions occurring between the medicaments prior to application.

According to another embodiment, the capsule can enable combining medicament with formulation solely during the activation procedure, thus eliminating interactions between the medicaments and the formulations prior to activation and release to the nasal cavity.

In another embodiment of the device, it is adapted to hold a canister of medication adapted for use in a metered-dose inhaler. In this embodiment, retracting the handle also induces the canister of medication to discharge its dose into a flowable substance capsule, from which the device entrains the aerosolized medication and delivers it.

In another embodiment of the device, the device is adapted for one-step operation. In this embodiment, extending the handle (4) draws external air into the device, as described hereinabove. In this embodiment, retracting the handle delivers the external air through the valve mechanism, through the flowable substance capsule and into the nasal passages. This embodiment has no mouthpiece, as activation is enabled by means of the handle (4), not by means of inhalation through a mouthpiece.

Figure 11:
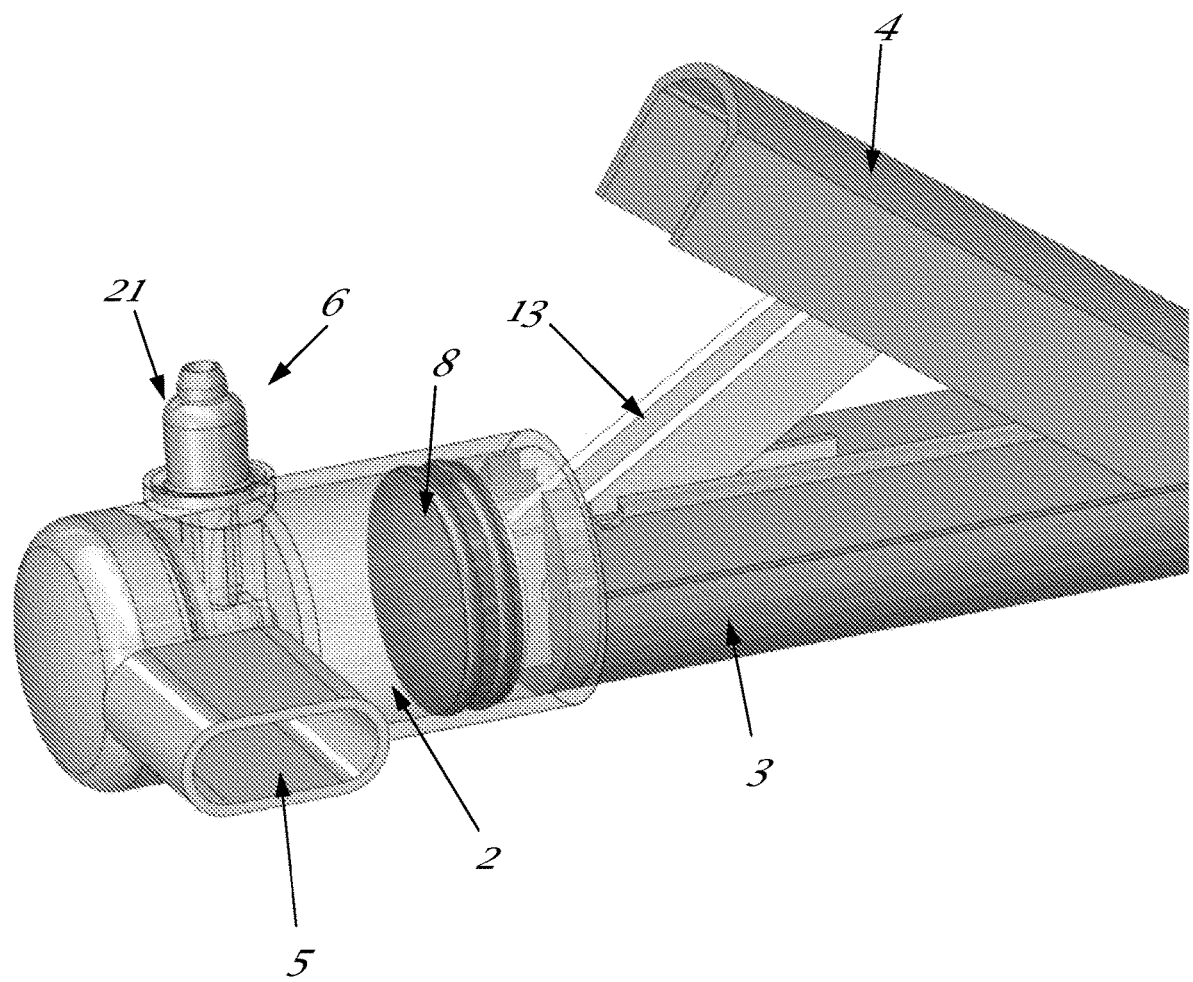
FIGS. 11-17 schematically illustrate another embodiment of the present invention.

In another embodiment of the device, illustrated in FIG. 11, the nosepiece (6), the capsule (21) and the mouthpiece (5) are removable, and the handle (4) pivots about the lower end of the proximal end (3) rather than about the upper end, simplifying the design of the piston driver (13). In this embodiment, the piston driver (13) does not comprise a hinge, enabling it to be manufactured as a single piece.

In FIG. 11, the handle (4) is illustrated in the open position (i.e., the extended position).

Figure 12:
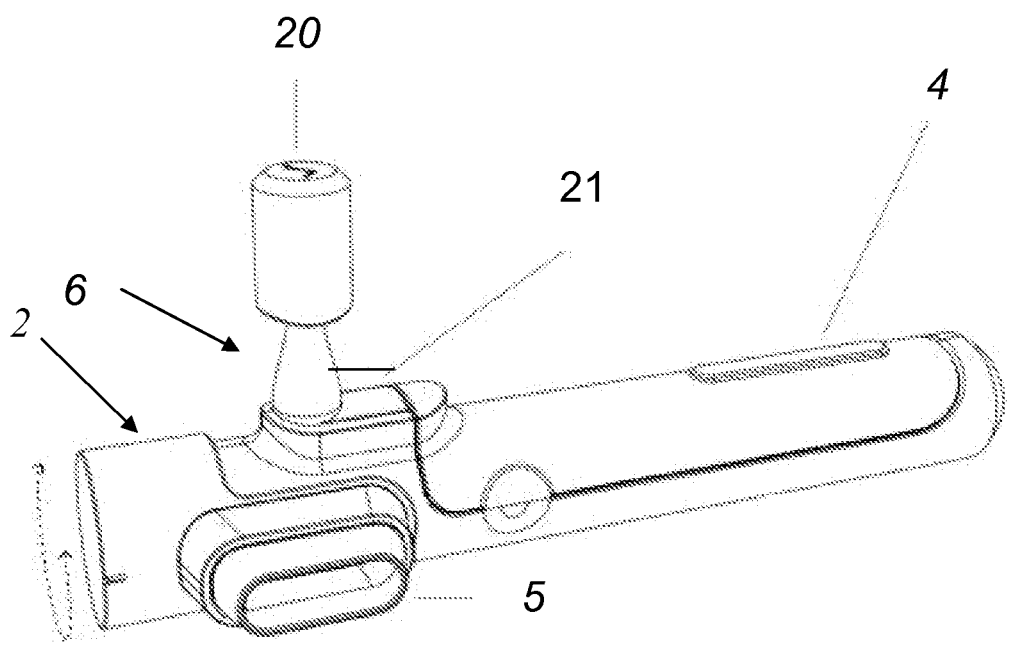

FIG. 12 illustrates another embodiment of the device, shown with the handle (4) in the closed position (i.e., the retracted position). In this embodiment, the mouthpiece (5), which is removable, is enabled to rotate, with the enclosure (2), around the body of the device, as shown by the dotted arrow.

As further illustrated in FIG. 12, the nosepiece (6) has a cap (20), enabled to protect the nosepiece when it is not in use. The cap (20) is shown partially covering the nosepiece (6), allowing the nosepiece (6) to be seen. The nosepiece (6) and medicine compartment (21) are a single unit, the nosepiece unit (43, see FIG. 14) which is removable and replaceable. In some embodiments, the nosepiece unit (6) and medicine capsule (not shown) form a single-use unit (43, see FIG. 14), where the medicine capsule (not shown) is integral with the medicine compartment (21), and the medicine compartment (21) is not refillable, the unit being discarded after use. In other embodiments, the medicine compartment (21) is refillable; an exhausted medicine capsule being replaceable by an unused one. In yet other embodiments, the medicine compartment (21) comprises a cartridge of medicine capsules, with means to replace an exhausted capsule with an unused one. In other embodiments, the cartridge is single-use, the nosepiece unit (43) being discarded when the cartridge is exhausted. In yet other embodiments, the cartridge is replaceable. In yet other embodiments, the nosepiece (43 or 6) and medicine compartment (21) form two units, enabling replacement of the nosepiece (6, or 43) and continued use of the medicine compartment (21).

The cartridge can be single-use, comprising the substance alone, a mixture of different substances, a mixture of one or more substances and one or more carriers, and any combination thereof. Similarly, a multi-dose cartridge can comprise multiple cartridges, each cartridge comprising, the substance alone, a mixture of different substances, a mixture of one or more substances and one or more carriers, and any combination thereof. The device can open a single capsule each time it is used, or a plurality of capsules, with the capsules being opened with each use of the device being any of the combinations described hereinabove.

Figure 13:
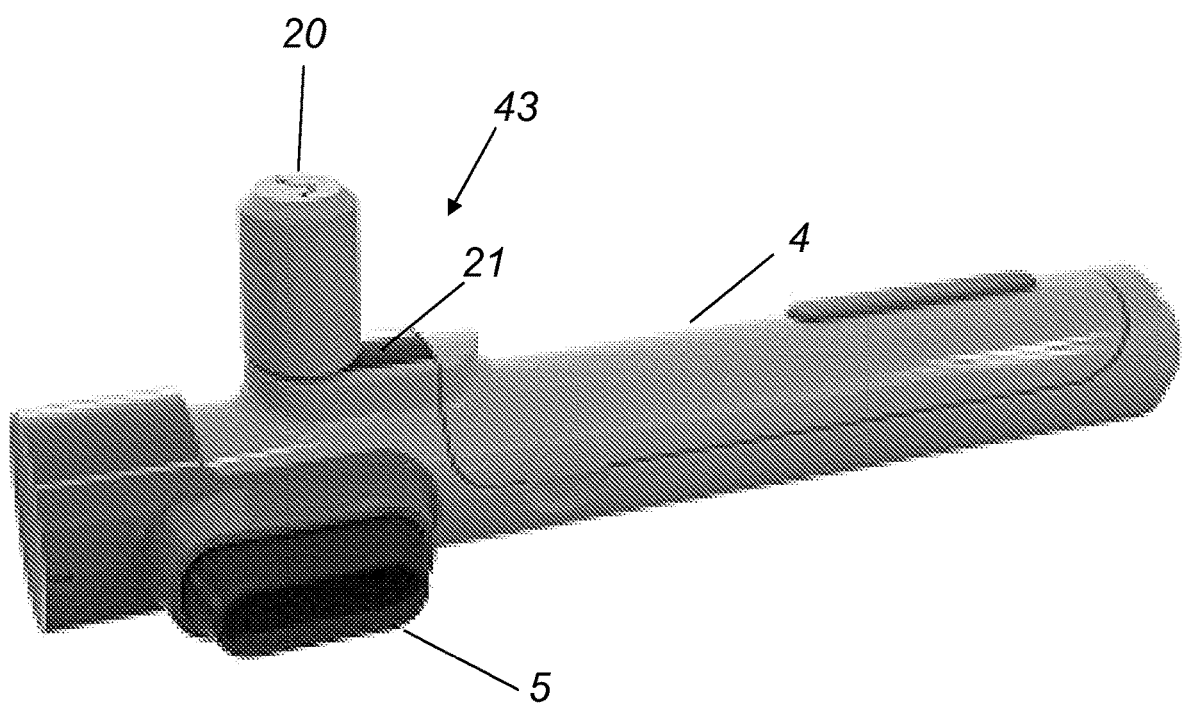

FIG. 13 illustrates an embodiment of the device in its rest position, when not in use. When the device is not in use, the cap (20) fully covers the nosepiece (6, not shown). The handle (4), when in the closed position, prevents the nosepiece unit (43) from being removed from the device. The mouthpiece (5) is visible. In other embodiments of the device, the mouthpiece (5) also has a removable cover.

Figure 14:
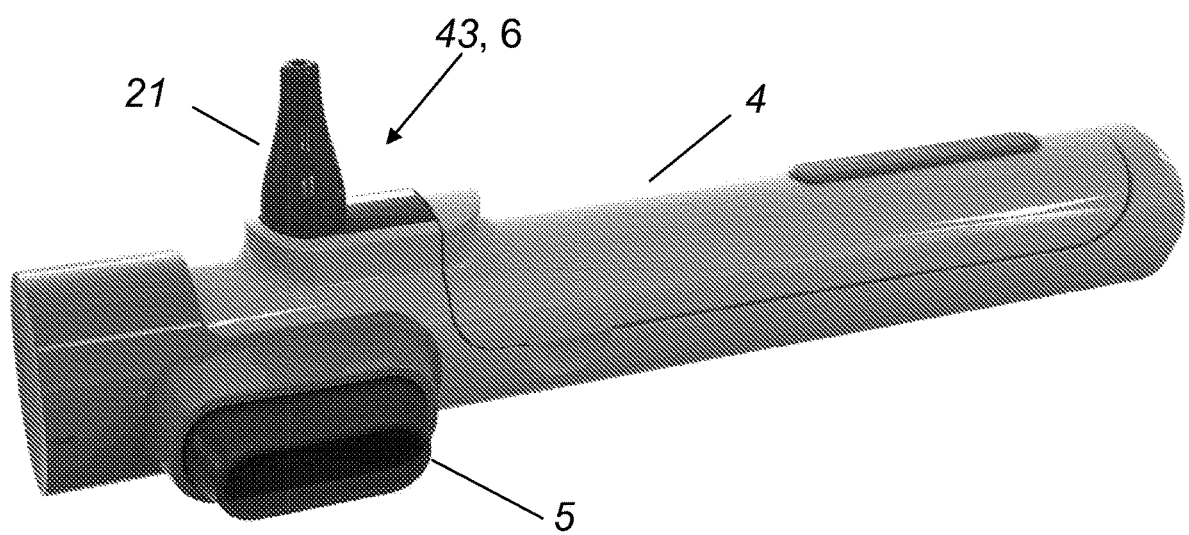

FIG. 14 illustrates the device of FIG. 12 in the closed position with the cap (20) fully removed so that the nosepiece (6 or 43) is visible. The handle (4) prevents the nosepiece unit (6 or 43) from being removed from the device. FIG. 14 illustrates the appearance of the device both preparatory to being inserted in the mouth and a nostril.

Figure 15:
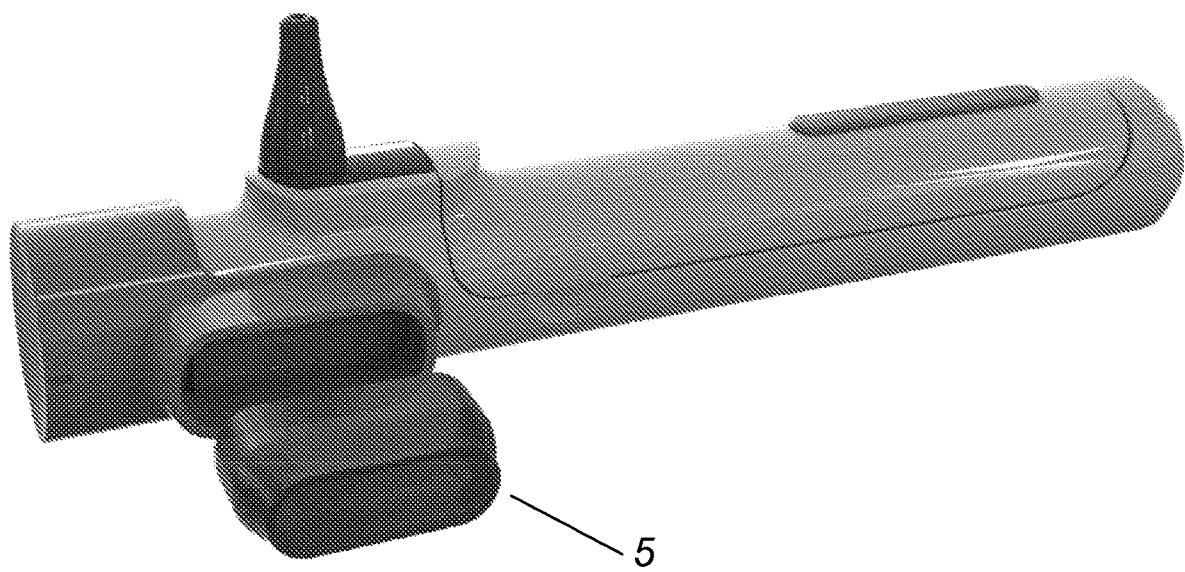

FIG. 15 illustrates removal of the mouthpiece (5) from the device of FIG. 12.

Figure 16:
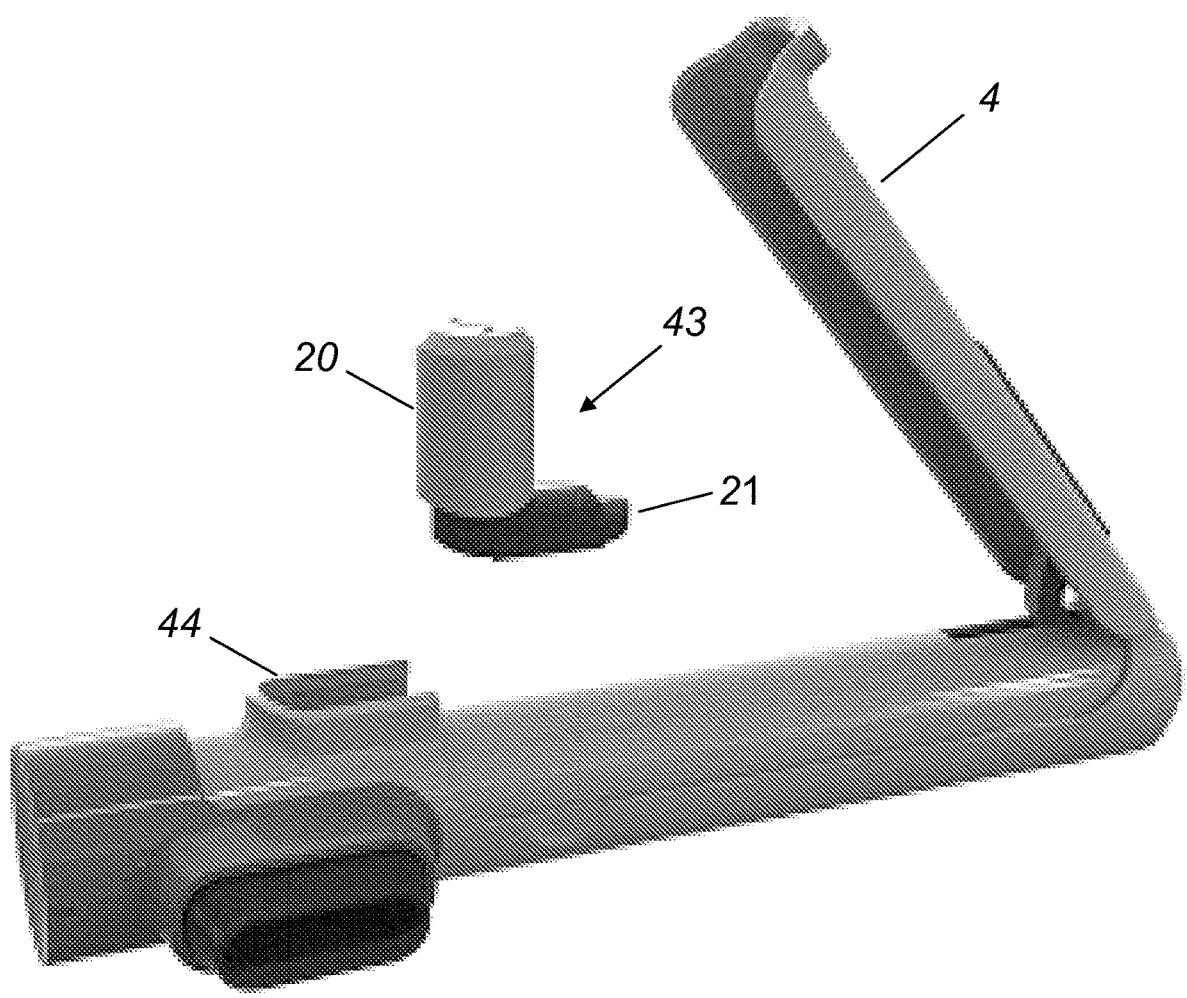

FIG. 16 illustrates the device of FIG. 12 with the handle (4) in the open position, allowing removal of the nosepiece unit (43), either for replacement of the nosepiece unit or for emplacement of a fresh medicine capsule within the nosepiece unit. In FIG. 16, the cap (20) is shown fully covering the nosepiece (6, not shown). The nosepiece unit retainer (44) is visible. In this embodiment, the nosepiece unit (43) is emplaced by sliding it along the nosepiece unit retainer; mating ridges and grooves on the mating faces of the nosepiece unit retainer (44) and the medicine compartment (21) enabling the nosepiece unit (43) to be affixed to the device firmly and removably.

Figure 17:
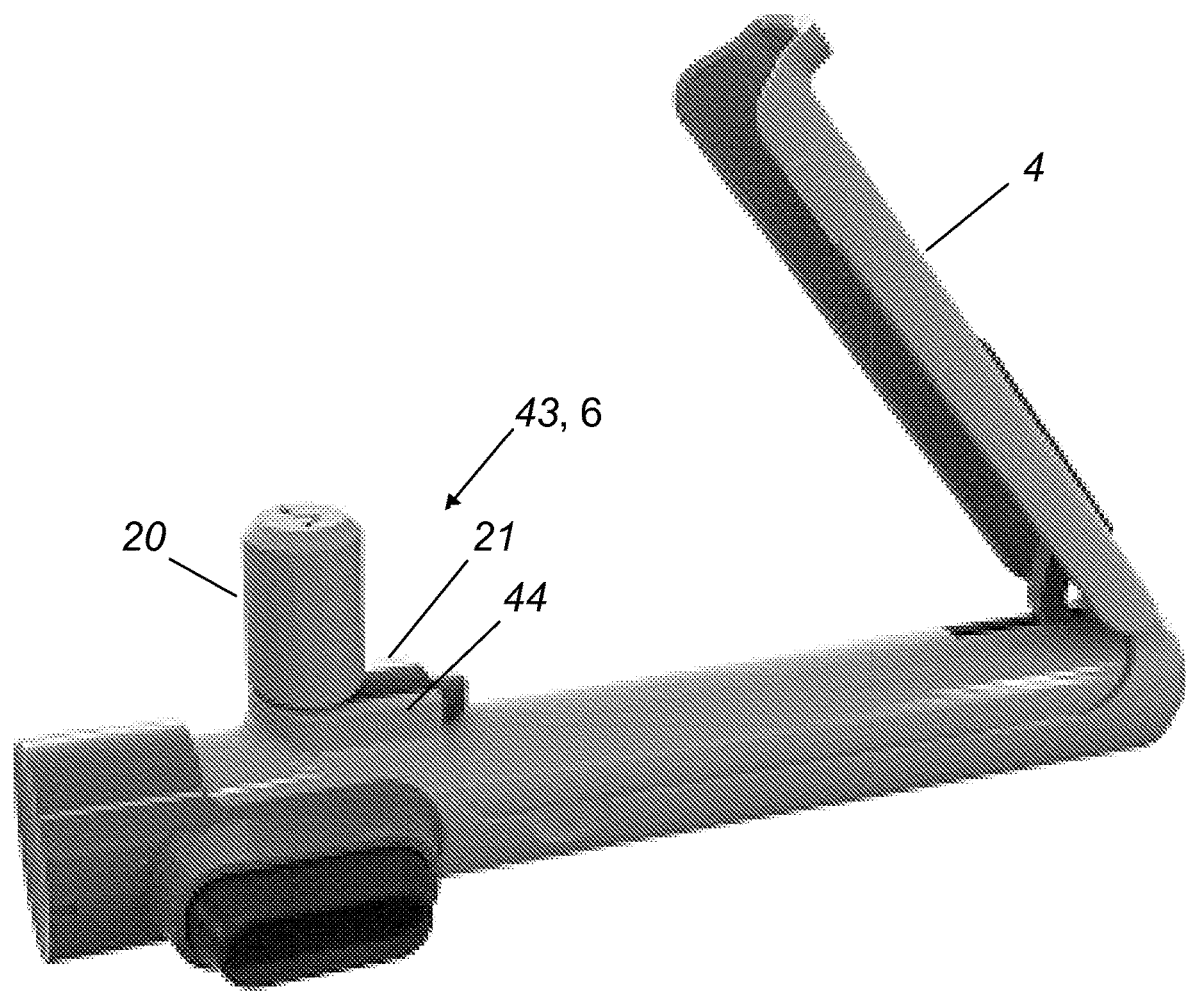

FIG. 17 illustrates the device of FIG. 12 with the handle (4) in the open position, after emplacement of the nosepiece unit (43). The cap (20) covers the nosepiece (6, not shown). The nosepiece unit (43) is firmly and removably held by the nosepiece unit retainer (44), a portion of which surrounds the medicine compartment (21).

In some embodiments, an air filter is incorporated into the air inlet that enables entry of atmospheric air into the space above the piston so that the air entering the patient's nostril has been filtered before entrainment of the substance to remove undesirable elements such as, but not limited to, particulates, bacteria, viruses, moisture and undesired particles from the air entering the patient's nostril. In preferred embodiments, the air filter is removable and replaceable. In other embodiments, the air filter is incorporated into the air channel 16 between the piston chamber and the lower air passage. In preferred embodiments, the air filter is removable and replaceable. According to another embodiment, the air filter is positioned in the air chamber part in the lower area where the piston reaches the chamber at is most open position (most extended position of the handle).

In some embodiments, an auxiliary air filter is incorporated into the mouthpiece. In some of the embodiments with auxiliary air filter, the auxiliary air filter is removable and replaceable. In other embodiments with an auxiliary air filter, the air filter and the mouthpiece form a single, replaceable unit.

In all embodiments, the valve mechanism 10 forms a unidirectional valve. Air can flow from the piston chamber (the charging mechanism) into the lower air passage, and from thence to the nasal passages, but not from the lower air passage (or the nasal passages) into the piston chamber. Valve mechanism 10 also prevents air from flowing from the upper air passage to the lower air passage; it is not possible for aerosolized drug to pass from the lower air passage to the upper air passage, and from thence to the mouth, during the suction that fires the device, by raising valve mechanism 10 and unsealing air channel 16.

In some embodiments, the handle (4) has two extended positions, a fully-extended position which enables removal and replacement of the flowable substance capsule, the nosepiece unit, or the integral nosepiece unit and flowable substance capsule, and a second extended position.

From the fully-extended position (i.e., the open position of the handle), the device can be fully charged.

From the second extended position, a partially-extended position, the nosepiece or nosepiece unit is locked in place, and the device is enabled to further initiate charging. From this position, activation of the device (and thus, release of the flowable substance to the nasal cavity) is not possible as the piston has not yet reached its fully open position so that the piston has not yet received its full charge of atmospheric air.

This embodiment ensures that the flowable substance is in the correct position during charging and during firing, thereby ensuring delivery of the complete dose under the correct conditions as to air speed, pressure, air volume, and duration of flow.

In another embodiment, the flowable substance capsule comprises at least two compartments. At least one compartment contains medicament, while at least one other compartment contains compressed air (air compartment). In this embodiment, charging is enabled by causing the compressed air to flow from the at least one compressed air compartment into a compressed air chamber in the device, said compressed air chamber fluidly connected to air channel 16. An illustrative example of a method of causing the compressed air to flow from the at least one compressed air compartment into the compressed air chamber in the device comprises a port on the enclosure such that, when the flowable substance chamber is mounted to the enclosure, the port is enabled to fluidly connect the at least one compressed air compartment to the compressed air chamber. Retracting the handle (4) or placement of the capsule in its capsule retainer position (44) causes a piercing means to pierce a wall of the at least one compartment of the capsule, causing the air to flow from the at least one compressed air compartment into the at least one flowable substance chamber of the capsule. Many other methods of causing the compressed air to flow from the at least one compressed air compartment into the compressed air chamber in the device will be obvious to persons with ordinary skill in the art.

In another embodiment, the compressed air compartment is a unit separate from the flowable substance chamber, said compressed air compartment being sealingly placed in the proximal end of the device, or sealingly attached to the proximal end of the device.

According to the embodiments described hereinabove, the activation mechanism comprises a mouthpiece and activation is accomplished by sucking on the mouthpiece to lift the valve from its seat and initiate delivery of the substance. In other embodiments, the activation mechanism comprises a non-suction means for lifting the valve and initiating delivery of the substance.

This non-suction means (e.g., voice, mechanical, press on a button) of activating the device is preferred for a target population comprising persons with limited physical strength, such as, for non-limiting example, the frail elderly, children, and disabled people such as people lacking hands or people with nerve damage to the arms or hands. A non-suction means is also preferred for people who have difficulty coordinating breathing with firing the device, such as, for non-limiting example, people with severe COPD, children, and people with mental disabilities.

Figure 18:
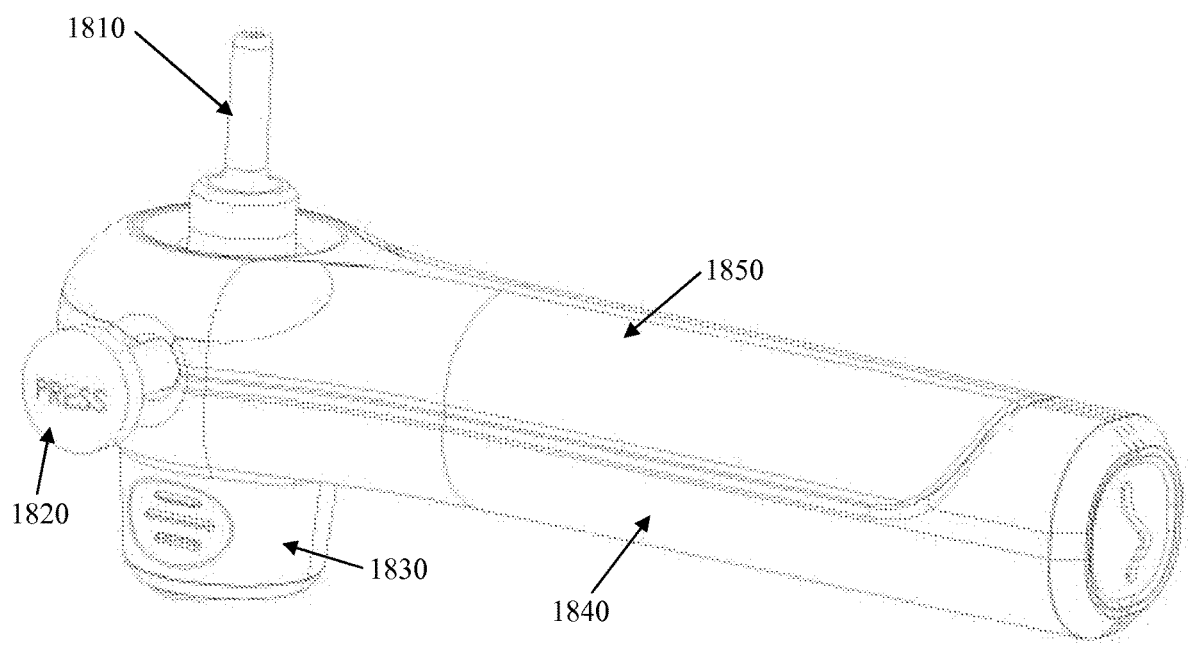
FIG. 18 schematically illustrates another embodiment of the present invention.

The embodiment shown in FIG. 18 is a non-limiting example of a preferred embodiment of this non-suction means of activating the device. The activating mechanism of the embodiment of FIG. 18 comprises a button. The user places the nosepiece in a nostril and depresses the button, thereby activating the device and initiating delivery of the substance. The means of converting the button press into the lifting of the valve can be any mechanism known in the art; the simplest example of which is attaching a lever mechanism to the button and to the spring mechanism which returns the valve to its rest position. Depressing the button compresses the spring, thereby initiating delivery.

The embodiment of FIG. 18 comprises an all-or-nothing activation mechanism, enabling reproducible and precise dose delivery, thus improving efficacy by increasing the probability of drug uptake in the nose; increasing safety, by eliminating drug contamination in lungs and gastrointestinal tract; and improving the user's experience by preventing the user from tasting the drug, as many drugs do not taste good.

Non-limiting examples of embodiments of non-suction activation mechanisms include, but are not limited to a button, voice activation, a lever, a slider, a catch, a predetermined sound pattern, a knob, a latch, a predetermined light pattern, and suction applied by a pump.

According to another embodiment, shown in FIG. 18, activation is by means of a button (1820). In some variants of this embodiment, the device is charged using a lever (1850) driving a piston (not shown) inside the handle (1840). The nosepiece (1810) is inserted into a nostril and the device is activated by pressing button 1820. The embodiment shown in FIG. 18 can compress a volume of up to 50 cc of air to a pressure of up to 10 bar, enabling a strong driving force to entrain the medication in capsule 1830. Other variants of this embodiment use the charging mechanisms described hereinbelow.

In other embodiments, a button activation mechanism such as is shown in FIG. 18 can be used with any of the charging mechanism described herein, including piston mechanisms and compressed-air driven mechanisms.

Another embodiment of an activation mechanism is voice activation, where activation occurs when a predetermined sound pattern is sensed by the activation mechanism.

Non-limiting examples of embodiments of activation mechanisms comprise activation by suction alone, where a user sucking on a mouthpiece activates the device, as discussed hereinabove; depressing a button, as discussed hereinabove; a combination of suction and depressing a button; and a combination of suction and voice activation. Other activation mechanisms and combinations thereof will be obvious to one skilled in the art.

Other embodiments of activation mechanisms include, but are not limited

The embodiments of FIGS. 3-18 comprise an all-or-nothing activation mechanism, enabling reproducible and precise dose delivery.

Figure 19:
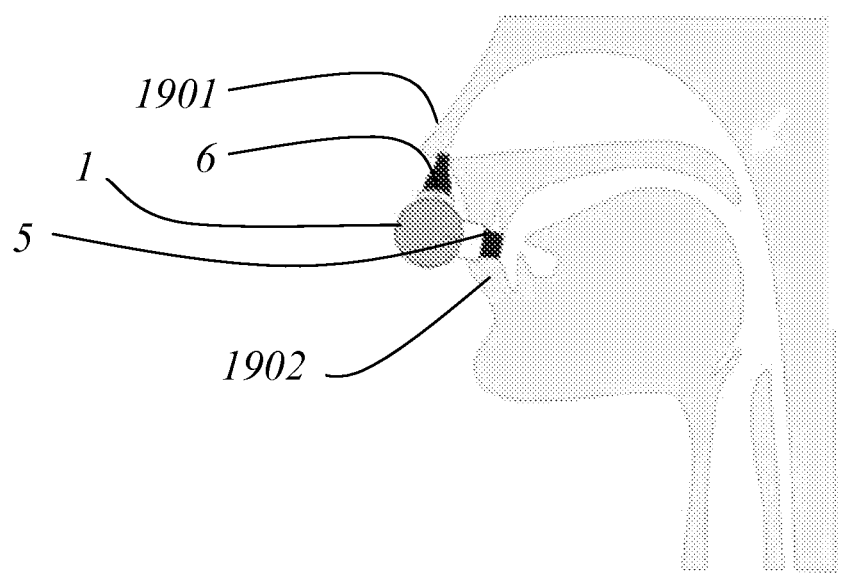
FIG. 19 schematically illustrates an embodiment of the present invention in use.

FIG. 19 illustrates the device in position for use. The device (1) is positioned between the nose 1901 and the mouth 1902 of a user, with the nosepiece (6) in a nostril and the mouthpiece (5) in the mouth. The user inhales through the mouth, causing suction in the mouthpiece, said suction, as described hereinabove, firing the device into the nostril.

The mouthpiece is in fluid connection with the valve mechanism 10 within the device such that suction on the mouthpiece opens valve mechanism 10, thereby enabling flow of compressed air through the device and from thence to the nostril and the nasal passages.

In some embodiments, the charging mechanism comprises a pump in fluid connection with valve mechanism 10 within the device such that suction on said mouthpiece opens valve mechanism 10, thereby enabling flow of predetermined amount of compressed gas with predetermined pressure from the pump through said device and from thence to the nostril and the nasal passages.

In some embodiments, the charging mechanism comprises a pressurized gas, contained within a gas enclosure adapted to enclose pressurized gas. The gas enclosure can be separate from the device and connectable to it via, for non-limiting example, a hose fluidly connected to a pump or compressed-gas storage means such as a gas bottle; or it can be emplaceable within the handle when the handle is in the extended position such that retracting the handle enables the predetermined amount of compressed gas with predetermined pressure within to be deliverable to the nasal passages; or it can be a part of the medication capsule, emplaceable within the handle when the handle is in the extended position such that retracting the handle enables the predetermined amount of compressed gas with predetermined pressure within to be deliverable to the nasal passages. The gas is preferably air, but can be nitrogen, oxygen, helium, neon, xenon, carbon dioxide, or any mixture thereof.

The pressurized gas enclosure can have a single compartment or a plurality of compartments.

In some embodiments, the charging mechanism comprises a mechanism selected from a group consisting of a catch, a button, a predetermined sound pattern, a lever, a slider, a rotatable knob, a latch, a predetermined light pattern, suction applied by a pump, and any combination thereof. The predetermined sound pattern can be, for example, a voice command, a whistle of a particular pitch, a constant tone, a fragment of a tune, or any other sound pattern. The predetermined light pattern can be the blocking of a light beam, so that a sensor becomes dark, shining a light on a sensor, a blinking light falling on a sensor, such as the third time light falls on a sensor within a second, the device fires, or any other light pattern not likely to occur by accident.

In some embodiments, the activation mechanism comprises a mechanism adapted to initiate delivery of the flowable substance to the nasal passages. The mechanism can be any combination of a releasable catch, a depressible button, a detectable predetermined sound pattern, a movable lever with a first position and a second position where moving the lever from a first position to a second position initiates activation, a movable slider where moving the slider from a first position to a second position initiates activation, a rotatable knob, a releasable latch, a detectable predetermined light pattern, and suction applied by a pump.

In preferred embodiments, if the activation mechanism is a lever, movement of the lever from a first position to a second position charges the device, while movement from the second position to the first position activates it. Activation can either be automatic or manual. If the mechanism is a button, for non-limiting example, depression of the button charges the device, raising the button activates it. Again, raising the button can be either manual or automatic.

In preferred embodiments, the capsule is removably emplaceable within the device, as described hereinabove.

In some embodiments, the charging mechanism is adapted to open the medication capsule. In other embodiments, the means to open the capsule is independent of the charging mechanism. In these embodiments, the opening means can be activated by the activation mechanism, or by an independent mechanism such that the device has three-step operation, with the device charged in a first step, the flowable substance capsule opened in a second step, and the flowable substance delivered to the nasal passages in the third step. In these embodiments, the opening means can be activated by pressing a button, by turning a knob, by emitting a predetermined sound pattern (such as uttering a voice command), by emitting a predetermined light pattern, such as shining a light on a predetermined spot or placing a hand over (and thereby darkening) a predetermined spot), by moving a slider, by flipping a lever, or by any other means known in the art for initiating an action.

In embodiments where the charging mechanism opens the capsule, the flowable substance capsule can be opened at the or before the beginning of the charging process, at the time the charging mechanism begins its transformation from the extended position to the retracted position, or the flowable substance capsule can be opened at some time during the transformation from the extended position to the retracted position, or the flowable substance capsule can be opened at or after the end of the transformation from the extended position to the retracted position.

The means to open the flowable substance capsule can be selected from a rod, a spear, a needle, a knife, a peel-off portion attached to said capsule, any other means known in the art for opening sealed capsules, and any combination thereof.

In some embodiments shown hereinabove, the nosepiece is fully removable from the device. In other embodiments shown hereinabove, the nosepiece is permanently attached to the device. In yet other embodiments, only a portion of the nosepiece is removable.

Similarly, the mouthpiece can be fully removable, be partially removable, with a portion thereof removable, or be fully permanently attached to the device.

Criteria of the device can be optimized to include: ensuring that a single dose of the substance is delivered in its entirety, ensuring that the single dose contains the predetermined amount of the substance, ensuring that the dose is delivered to the desired region of the nose, and ensuring that delivery of the dose causes the minimum possible discomfort to the patient. Any combination of these criteria can be optimized for; each particular combination giving rise to a different embodiment of the device.

In preferred embodiments of the device, the nosepiece is removably emplaceable in the nostril.

In some embodiments of the device, the nosepiece is emplaced within the nostril; either sealingly or such that air can enter the nostril while the nosepiece is emplaced therein. In other embodiments, the nosepiece is emplaced against the opening of the nostril. Again, it can be sealingly emplaced thereunto, or air can enter the nostril while the nosepiece is emplaced thereon.

In some embodiments, the charging mechanism comprises a filter adapted to remove from the external air at least one selected from a group consisting of particulates, bacteria, viruses, moisture, and undesired gases before the air reaches the flowable substance.

In some embodiments, the flowable substance capsule comprises a filter adapted to remove from the external air at least one selected from a group consisting of particulates, bacteria, viruses, moisture, and undesired gases before the air reaches the flowable substance. This filter will be upstream of the flowable substance capsule.

In some embodiments, the mouthpiece comprises a filter adapted to remove from the air at least one selected from a group consisting of particulates, bacteria, viruses, moisture, and undesired gases before the air reaches the user's mouth. Such a filter, by preventing unpleasant odors or tastes from reaching the user and by preventing particulates from entering the user's mouth, can make the experience of using the device much more pleasant for the user. By removing bacteria and viruses, infection of the user can be prevented.

In embodiments comprising a filter, the filter can be comprised within the piston, filtering the air as it enters the piston chamber or as it exits the piston chamber; or in any other appropriate position within the charging mechanism, the filter can be positioned in the region connecting the air or gas enclosure and the valve mechanism; or it can be comprised within the medicament capsule. If desired, a filter can be comprised within the mouthpiece. Such a mouthpiece filter will not affect the quality of the air entering the nasal passages. As described hereinabove, it can make the experience of using the device much more pleasant for the user by preventing particulates or unpleasant odors from the interior of the device from entering the patient's mouth.

In some embodiments, the nosepiece is at least partially removably and at least partially replaceably attachable to the device, such that a clean and/or sterile nosepiece can be emplaced in or against the user's nostril. Such embodiments reduce the risk of the nosepiece becoming blocked by nasal secretions and also reduce the chance of the user becoming infected (or re-infected) by matter remaining on the nosepiece after use.

In some embodiments, the mouthpiece is at least partially removably and at least partially replaceably attachable to the device, such that a clean and/or sterile mouthpiece can be placed in the user's mouth. Such embodiments reduce the risk of the mouthpiece becoming blocked by saliva or other matter in the user's mouth and also reduce the chance of the user becoming infected (or re-infected) by matter remaining on the mouthpiece after use.

In some embodiments, the container contains only a single dose of the substance, the container or the device being replaced after each use. In other embodiments, the container or the device contains multiple doses of the substance, preferably packed separately, so that the dose is fresh for each use.

According to another embodiment the device of the present invention additionally comprises indicating means adapted to provide an indication the user if said entrain of said flowable substance within said enclosed air and transport the same from said container to said nasal passages has been successful. In such a manner, the user will be informed whether or not the delivery of said substance was made.

According to said embodiment, the indication is visible by means of a change of color, audible by means of a predetermined sound pattern and any combination thereof.

Many factors need to be considered when optimizing the device. Among them are the comfort of the user, efficient delivery of the substance to the desired location, lack of dripping during or after delivery, and the nature of the substance to be delivered. An optimized delivery will be defined by a complex interplay of these factors. Many factors will determine optimum delivery. Delivery factors that need to be considered in adapting the device to provide optimum delivery of the substance are selected from a group consisting of the length of time over which the delivery occurs, the air speed in the nostril during delivery, the air speed in the nostril during delivery of the gas with entrained substance, the volume of air entering the nostril, the excess air pressure in the nostril, the presence of turbulence in the region of the substance, the absence of turbulence in the region of the substance, the presence turbulence in the air channels within the device, the absence of turbulence in the air channels within the device, the presence of turbulence in the nostril, the absence of turbulence within the nostril, the presence of turbulence in the nasal passages, the presence of turbulence in the nasal passages, and any combination thereof.

In some embodiments, the activation mechanism comprises a hollow flexible tegument, and compressing and releasing the tegument opens the valve mechanism, thereby enabling flow of compressed air through the device. The air can be compressed by compression of the tegument, or compressing the tegument can open the valve, thereby releasing compressed air confined, for example, within a chamber.

In some embodiments, the activation mechanism comprises one of a group consisting of a compressible spring, a magnetic field, an electric field and a piezoelectric device, the activation mechanism activated by means selected from a group consisting of a pressable button, a flippable switch, a rotatable knob and a bendable lever, the activation mechanism opening the valve mechanism, thereby enabling flow of compressed air through said device.

The device takes air or another gas from a predetermined position, compresses it during the charging step, then, during the activation step, uses the compressed air to entrain a flowable substance, usually a medicament, in the compressed air, and deliver the compressed air with entrained medicament to the nasal passages via a nostril.

In some embodiments, the predetermined position of the compressed air is a pressurized gas enclosure adapted to enclose pressurized gas, in fluid connection with the nosepiece. In other embodiments, the predetermined position is an air-tight enclosure within the device, the air-tight enclosure charged when the charging mechanism is transformed from the extended position to the retracted position, the charging mechanism adapted to pressurize external air into the air-tight enclosure.

In some embodiments, as described hereinabove, the pressurized gas enclosure is within the handle of the device. In other embodiments, the pressurized gas enclosure and the flowable substance capsule form a single unit. In yet other embodiments, the pressurized gas enclosure and the flowable substance capsule form separate units.

In the embodiments described hereinabove, the aerosol is created during activation, by the entrainment of the flowable substance in the predetermined amount of compressed gas as the gas passes through or by the flowable substance during activation.

In other embodiments, an aerosol is created before activation, during the charging process or suing any process known in the art to create an aerosol.

In yet other embodiments, the aerosol is created by a separate device and is provided to the device of the present invention. The aerosol from the separate device can be created by the separate device during activation or before activation.

In some embodiments of the two-step mechanism, the activation mechanism comprises a pump in fluid connection with a valve mechanism within the device such pre-activation opens the valve mechanism, thereby enabling flow through said device of air compressed by the pump.

In some embodiments of the two-step mechanism, the activation mechanism comprises a hollow flexible tegument, and compressing and releasing the tegument opens the valve mechanism, thereby enabling flow of compressed air through the device. The air can be compressed by compression of the tegument, or compressing the tegument can open the valve, thereby releasing compressed air confined, for example, within a chamber.

In some embodiments of the two-step mechanism, the activation mechanism comprises one of a group consisting of a spring, a magnetic field, an electric field and a piezoelectric device, the activation mechanism activated by means selected from a group consisting of a button, a switch, a knob, a lever, and suction applied by a pump, the activation mechanism opening the valve mechanism, thereby enabling flow of compressed air through said device.

In some embodiments of the two-step mechanism, the predetermined position of the compressed air is a pressurized air container adapted to enclose pressurized air, in fluid connection with said nosepiece.

It should be emphasized that any embodiment of the present invention and any variant thereof can be used for both for humans (medical use) and animals. Thus, any of the devices as disclosed above and any variant thereof can be used for veterinary applications as well as (human) medical applications.

EXAMPLES

Examples are given in order to prove the embodiments claimed in the present invention. The examples, which comprise pre-clinical, lab tests and clinical tests, describe the manner and process of the present invention and set forth the best mode contemplated by the inventors for carrying out the invention, but are not to be construed as limiting the invention.

Example 1

Distribution of a liquid aerosol in a glass maze model was measured for the device of the present application and commercial devices and a comparison of the distributions was made. The applicators were applied to the open end of the glass maze model and the aerosol passed through the internal glass maze to a tube container at the end of the glass maze section. The application was repeated four times for each applicator.

The applications were performed with a dye solution.

Results were measured as the amount of dye that was able to cross through the glass maze section and deposit in the tube container at the end of the glass maze section.

Measurements were made with a spectrophotometer: UV-2401-PC, UV Vis recording spectrophotometer, Shima D2U). Wave lengths: 300 nm; 665 nm.

Figure 20:
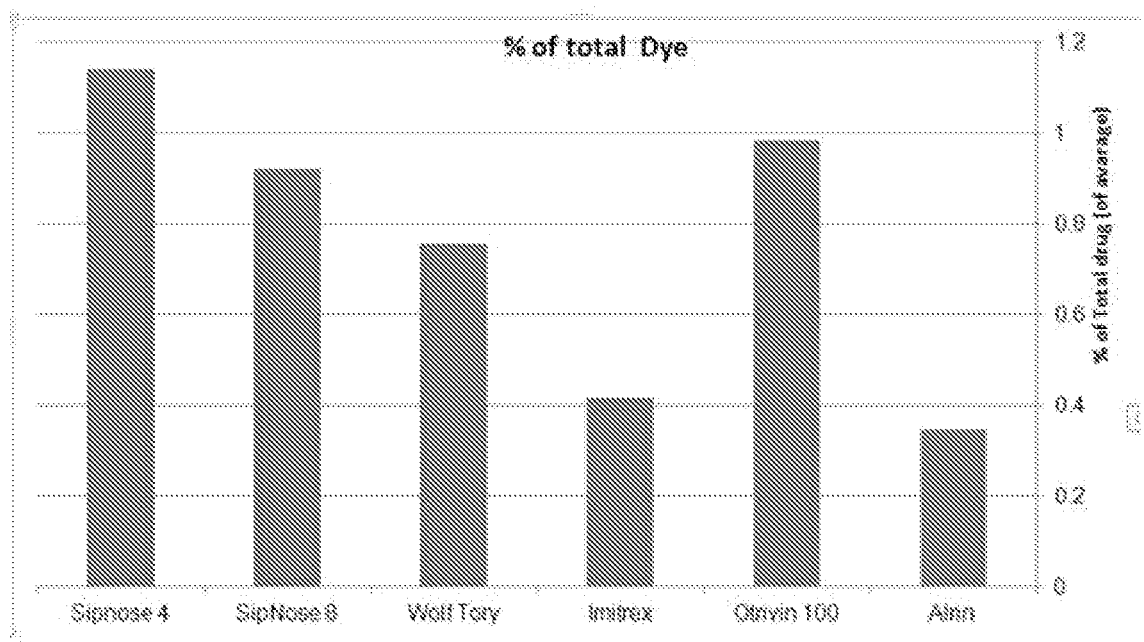
FIG. 20 illustrates a comparison of the present device with commercially available devices.

FIG. 20 shows the percentage of liquid aerosolized dye that crossed through the glass maze and deposited in the tube container at the end of the glass maze following applications with the present device following charging the device with condensed air (either with a pressure of 4 bars, SipNose 4, or with a pressure of 8 bars, SipNose 8), with the Wolf Tory device, the Imitrex device, the Otrivin 100 device and the Alrin device.

The present device shows better results at 4 bars pressure than all the other nasal applicators in terms of percentage of drug that has reached the tube (which correlates with reaching the inner and furthest nasal cavity areas). At 8 bars pressure, the present device shows better results than all the other devices except for the Otrivin 100.

Example 2

Distribution of a liquid aerosol in a 40 cm long glass tube was measured for the device of the present application and commercial devices and a comparison of the distributions was made.

The applications were performed with a dye solution. Each application comprised 100 microliter of dye solution.

FIG. 21 shows a comparison of the distribution for a standard applicator (2110) with the present device (2120). The distribution is much more even with the present device and extends much further into the tube. An enlarged view of the distribution of aerosolized dye for the present device at a distance of approximately 22 cm from the beginning of the tube is shown on the right (2130).

Example 3

Distribution of a dry powder in a glass maze model was measured for the device of the present application and commercial devices and a comparison of the distributions was made. The applicators were applied to the open end of the glass maze model and the aerosol passed through the internal glass maze to a tube container at the end of the glass maze section. The application was repeated four times for each applicator.

The applications were performed with a dye, Methylene Blue (MB) (CAS-61-73-4), MW: 319.85

Results were measured as the amount of dye that was able to cross through the glass maze section and deposit in the tube container at the end of the glass maze section.

Measurements were made with a spectrophotometer: UV-2401-PC, UV Vis recording spectrophotometer, Shima D2U). Wave lengths: 300 nm; 665 nm.

Measurements were made with a spectrophotometer: UV-2401-PC, UV Vis recording spectrophotometer, Shima D2U). Wave lengths: 300 nm; 665 nm.

As shown in FIG. 22, the device of the present invention, the SipNose enabled nearly 4 times as much dry powder to go through the glass maze and reach the final container when compared to the best commercial devices, one that simulates the DirectHaler and/or OptiNose that are based on exhaled air activation.

Note that the DirectHaler, OptiNose, SNBL and APTAR are represented by models that simulate their technology.

Example 4

Distribution of a dry powder in a model of the human nasal passages was measured for the device of the present application and a commercial applicator representing the DirectHaler technology. Dye powder was detected at each nose layer of the model (1 cm apart) and a comparison of the distributions was made. The application was repeated five times for each applicator.

Results were measured as the amount of dye that deposited in each nose layer of the model (1 cm apart). In order to measure the amount of dye powder that had deposited in each nose layer of the model, the dye in the tube container was solubilized with saline solution, as described above for Example 1.

Figure 23:
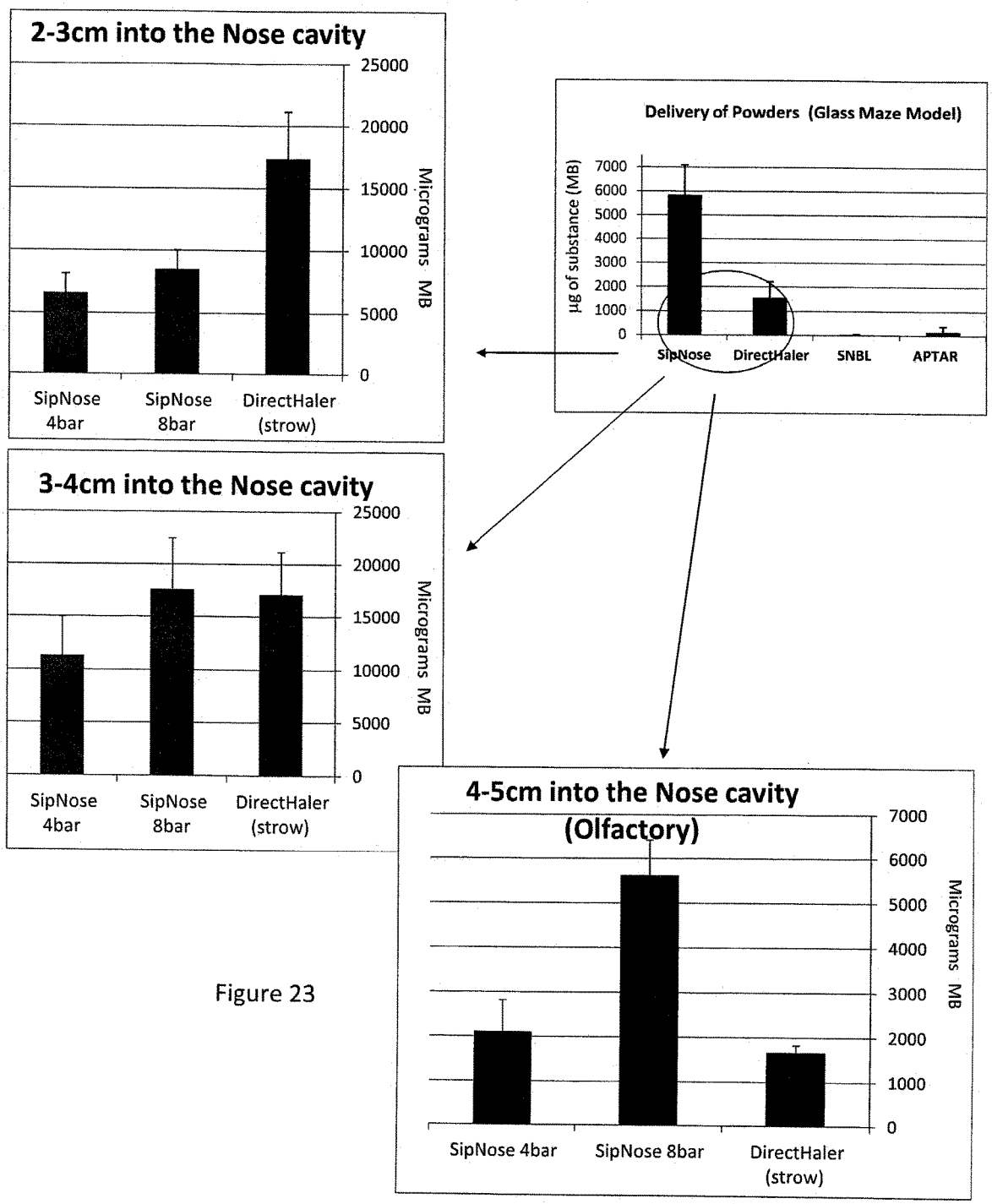
FIG. 23 illustrates a comparison of the present device with commercially available devices.

FIG. 23 shows a comparison of the powder deposition in the nasal cavity model between SipNose (4 and 8 Bars) and the straw model that represents the DirectHaler. Deposition of the powder in the lower layers of the nose (layers 2-3 cm and 3-4 cm) are comparable between SipNose and DirectHaler. For the inner layer at 4-5 cm that includes the olfactory epithelium, there is a significantly higher concentration, about 4 times as much, for the application with SipNose (8 Bar) versus the DirectHaler.

Example 5

Particle size distributions were compared for aerosols produced by commercial available nasal applicators and the present device.

Analysis was carried out with the Malvern Instrument MasterSizer.

Particle size distributions for 100 microliter of original formulations were compared to particle size distributions for Saline solution, as described below. The saline solution was 0.9 NaCl (B. Braun Melsungen AG, Germany).

Figure 24A:
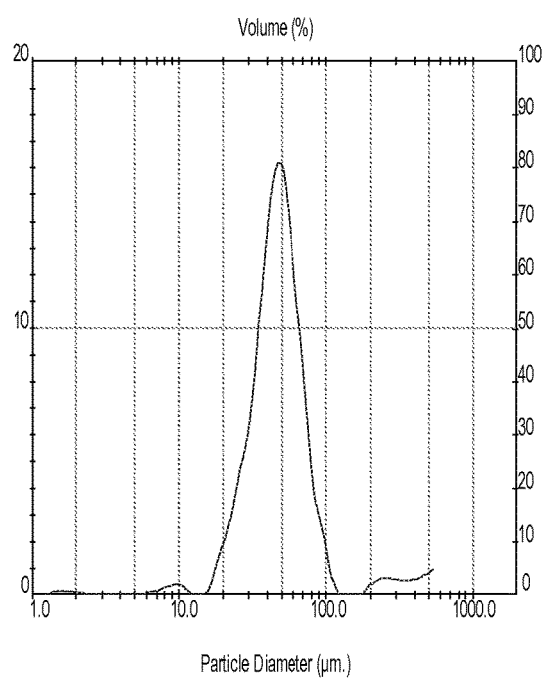
FIGS. 24-25 illustrate droplet sizes for commercial devices.
Figure 24B:
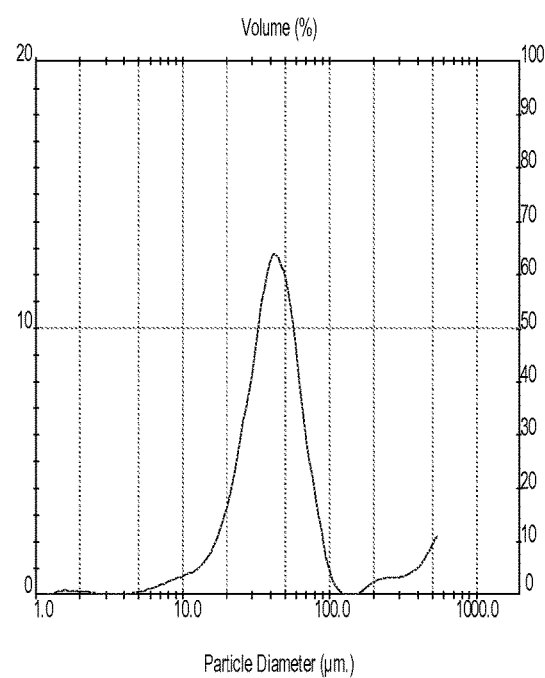

FIGS. 24A and 24B show particle size distributions for the Minirin Nasal Spray. FIG. 24A shows the distribution with saline solution (average diameter 47.3 μm) and FIG. 24B shows the distribution with Minirin solution (average diameter 73.7 μm).

Figure 25A:
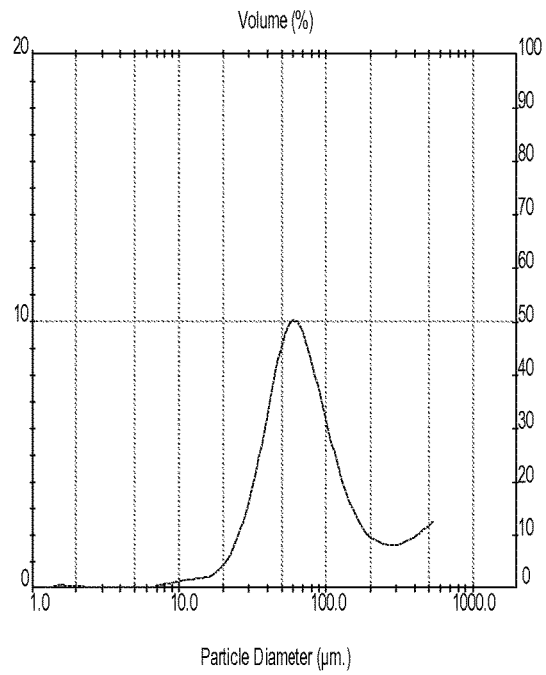
Figure 25B:
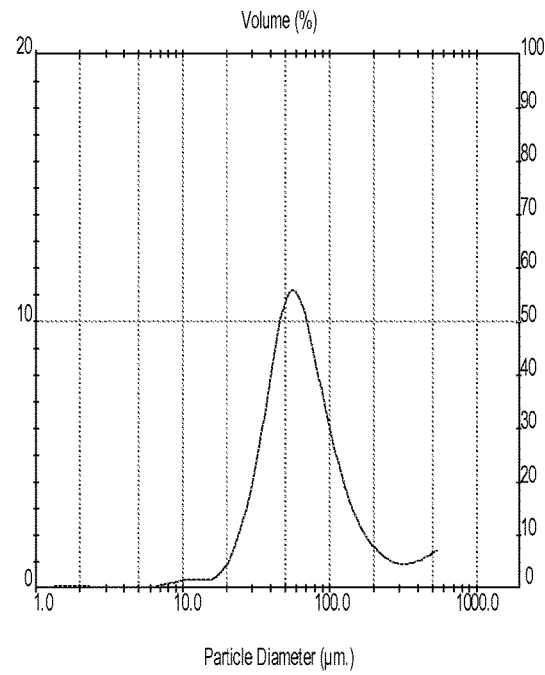
Figure 25C:
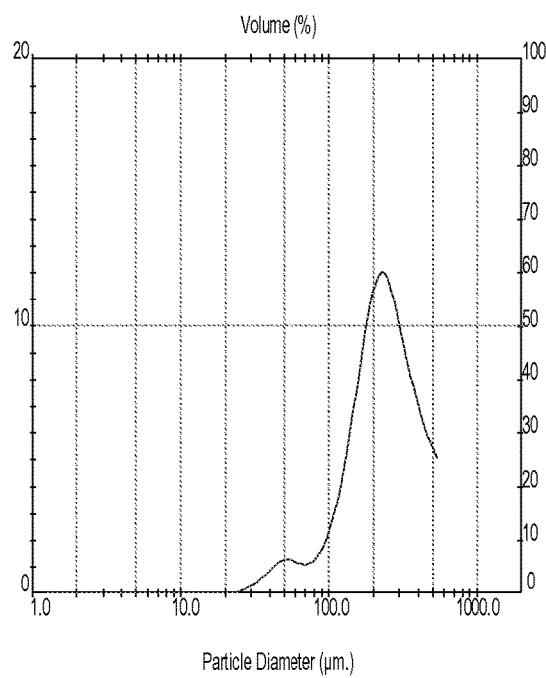

FIGS. 25 A-C show the particle size distributions for the Wolf Tory MAD 300, with three different applications of the same saline solution, the first saline application resulted in average diameter of 114 μm, the second saline application resulted in an average diameter of 94.8 μm and third in an average diameter of 254 μm.

Figure 26A:
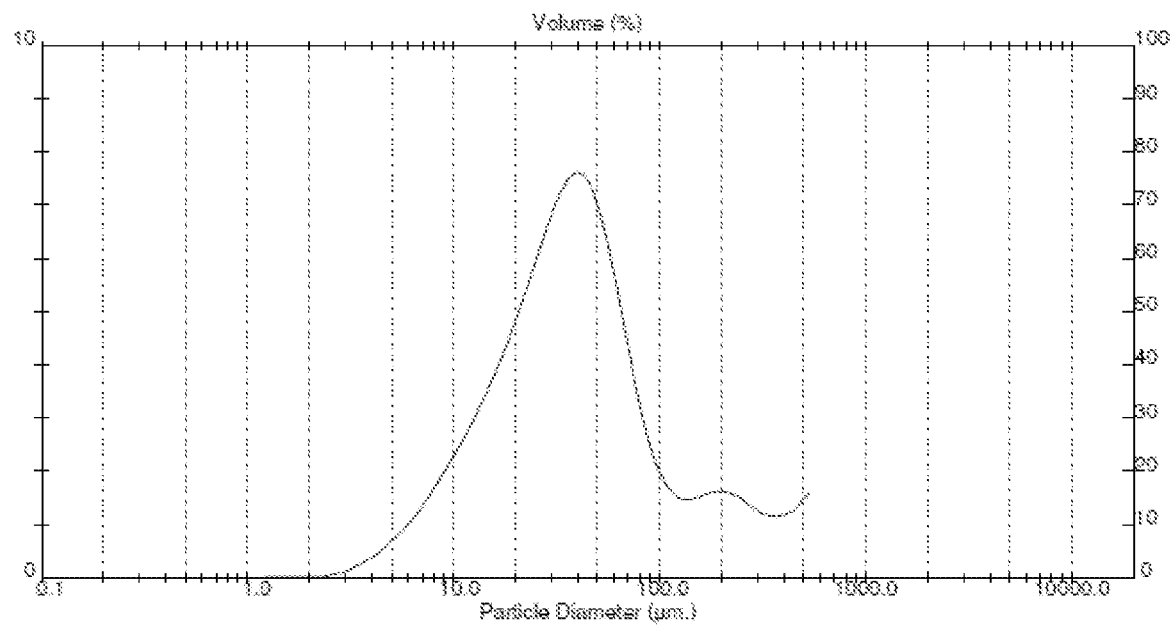
FIG. 26 illustrates droplet sizes for the present device.
Figure 26B:
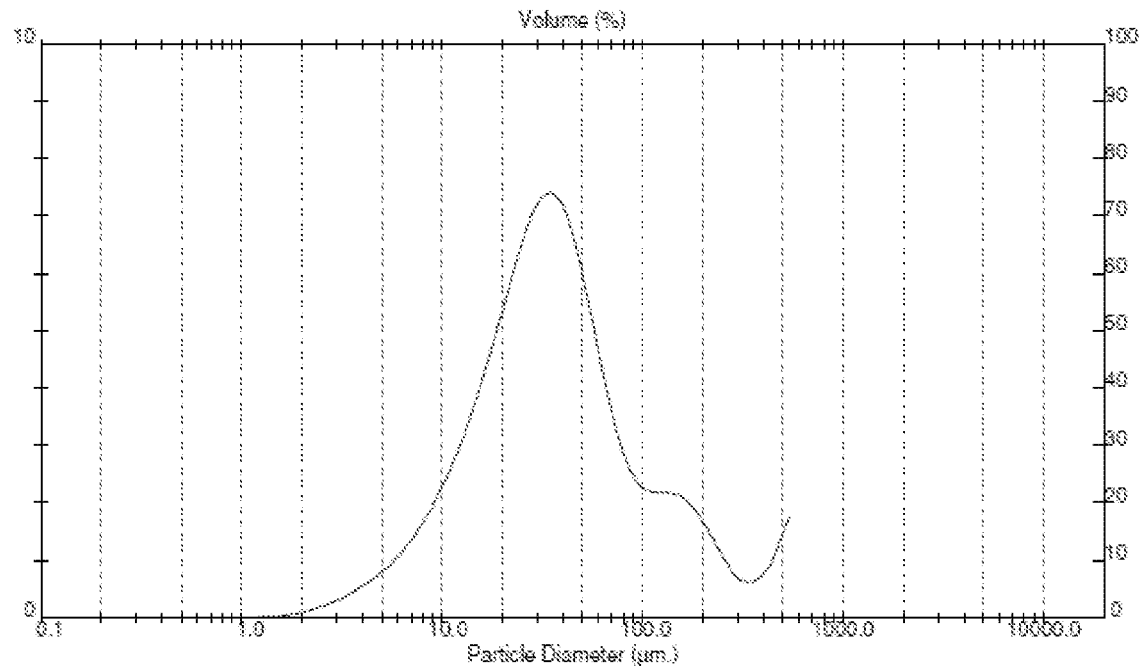

FIGS. 26A and B show the particle size distributions for the present device, for two applications. The particle diameters are 75.8 μm and 71.3 μm, showing a much narrower distribution than the Wolf Tory MAD 300 (FIGS. 25 A and B).

Figures 27, 28A, 28B:
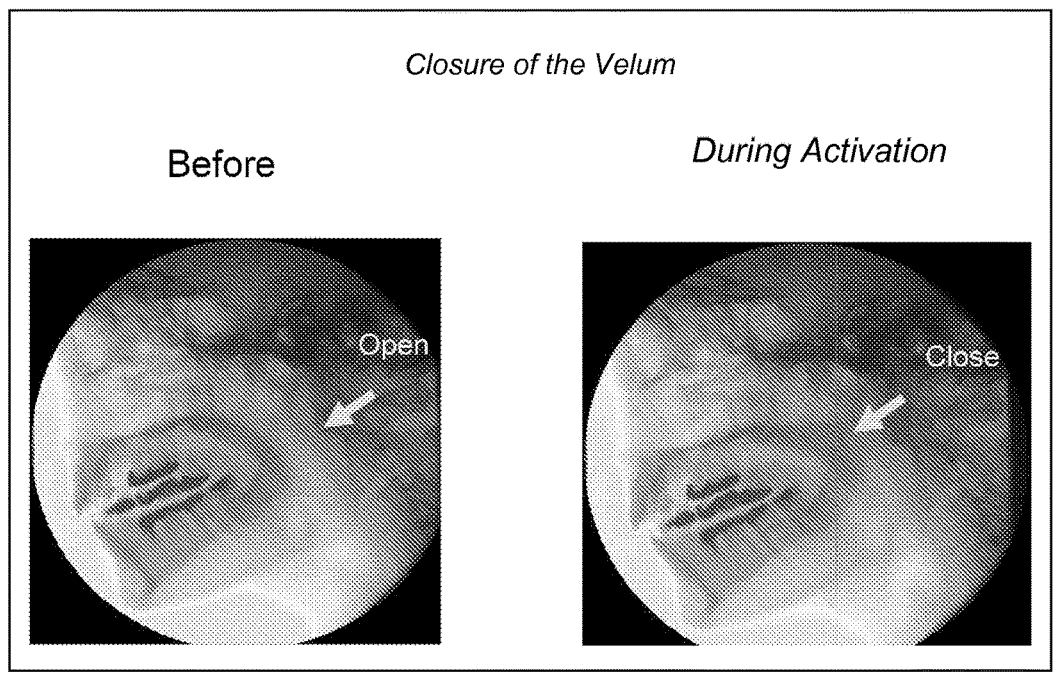
FIG. 27 illustrates a comparison of droplet sizes between commercial devices and the present device.

These data are summarized in FIG. 27, which tabulates the average particle diameters for the Minirin and Wolf Tory applicators and the present device.

The characterization of the aerosols and the comparison to commercial available nasal applicators as shown above demonstrates that applicators such as the Minirin and the Wolf Tory are affected by the user's strength and speed when activating those pump and syringe based applicators.

With the present device, as the activation is based on a mechanism of an all or nothing character, the reproducibility of the sample discharged will be much greater and the characteristics of its aerosol will be much more reproducible. The present device can be optimized for aerosol diameters as small as 1 μm and up to 50 μm in accordance to the specific needs of the specific fit for each drug-device combination product.

Example 6

Closure of the velum (soft palate) during use of the present applicator. X-Ray recordings were made and shots were taken (as single shots and as continuous video frames) before and after application of 100 μl iodine salt solution (Ultravist® 300 solution).

Tests were made on 2 healthy volunteers.

As a result of straw sucking action (which is the action that serves as the activation trigger in the present device), the soft palate (velum) closes and closes the passage between the nasal cavity, the pharynx and the airways to the lungs, as shown in FIG. 28A (before, open) and FIG. 28B (during, closed).

Example 7

X-Ray recordings were made and shots were taken (as single shots and as continuous video frames) before and after application of 100 μl iodine salt solution (Ultravisit 300 solution).

Tests were made on 2 healthy volunteers.

Figures 29A, 29B:
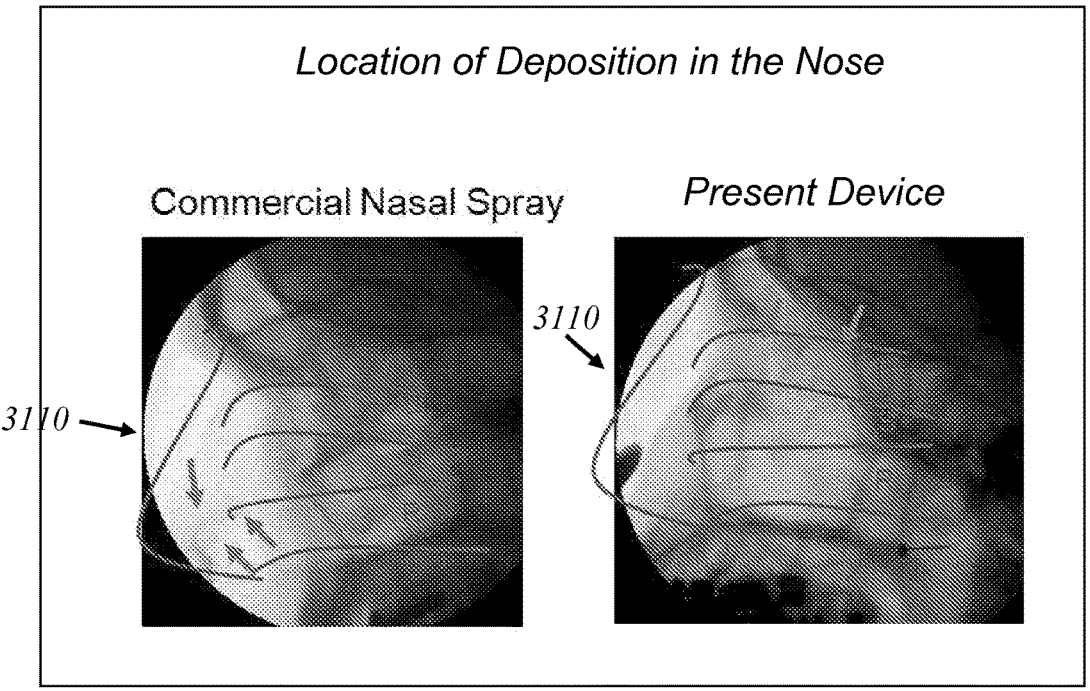
FIGS. 29-30 illustrate location of deposition of material in the nasal passages after application with the present device.

The location of the deposition was measured. FIGS. 29A and 29B show X-rays of the location of deposition for a healthy volunteer, for a commercial nasal spray (FIG. 29A) and the present device (FIG. 29B). The edge of the nose (2910) is marked for easy identification.

Figures 30A, 30B:
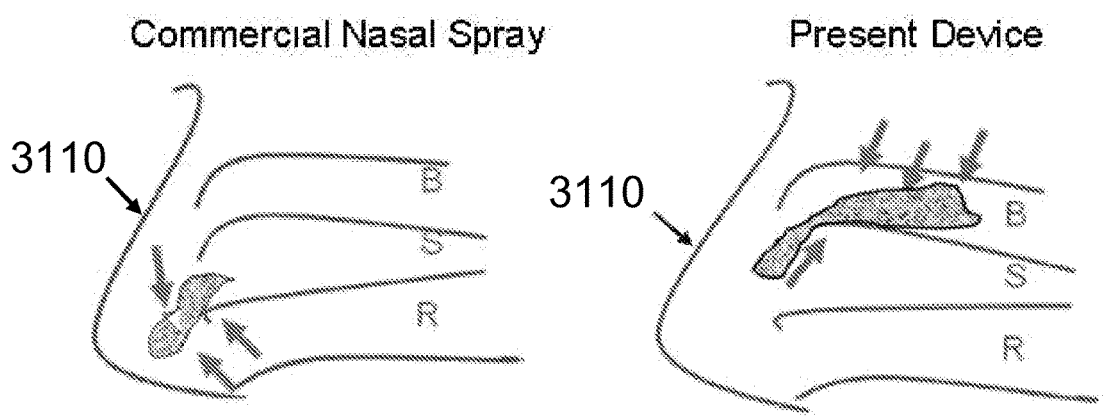

The location of the deposition is more easily seen in FIGS. 30A and 30B, where details have been removed and only the edge of the nose (2910) and the regions of the nasal passages (R, S, B) are shown. In FIG. 30, the deposition is shown in grey.

Aerosol released from a standard pump nasal spray applicator (the commercial example) distributed mostly at the peripheral area, close to the nostril and mostly around the applicator tip.

Aerosol released from present (SipNose) device distributed mostly in the inner upper area (at the area of the olfactory epithelium).

Example 8

Dye deposition in the olfactory epithelium following application with the present device.

Methylene Blue solution (as in Example 1) was applied to the rat nose with the present device. 15 microliter was applied to one nostril and immediately after that the animal was sacrificed and the nasal and brain tissue were exposed to follow the dye deposition.

FIG. 31A shows the location of $^{11}$C-choline with a PET-CT scan method, in a live rat and FIG. 31B shows the location of the dye following exposure of the nasal cavity epithelium post mortem. In both FIGS. 31A and 31B, dye deposition is concentrated at the olfactory epithelium. Some dye is shown at the area of the respiratory epithelium.

Example 9

Brain uptake of a compound with low blood-brain barrier (BBB) penetration $^{11}$C-choline, was applied by the device of the present application (refers also as SipNose). 33.2 µCi/5.3 µmol (approx. 0.551 mg) of $^{11}$C-choline was applied by the device of the present application to a 381 gm rat. A 45 min. dynamic PET scan was performed followed by a CT scan.

FIG. 32 shows locations of uptake. FIG. 32A shows uptake in the olfactory epithelium (upper curve) and the pharynx (lower curve, triangles), FIG. 32B shows uptake to the brain (upper curve, diamonds) and the lungs (lower curve, squares). It can be clearly seen that the deposition is greatest in the olfactory epithelium and least in the lungs (FIG. 32B, lower curve), with about 0.5% depositing in the brain very shortly following administration, increasing gradually thereafter to 0.6%. (These values of % ID/ml represents ~1.2% of the total drug administrated.)

Figure 33:
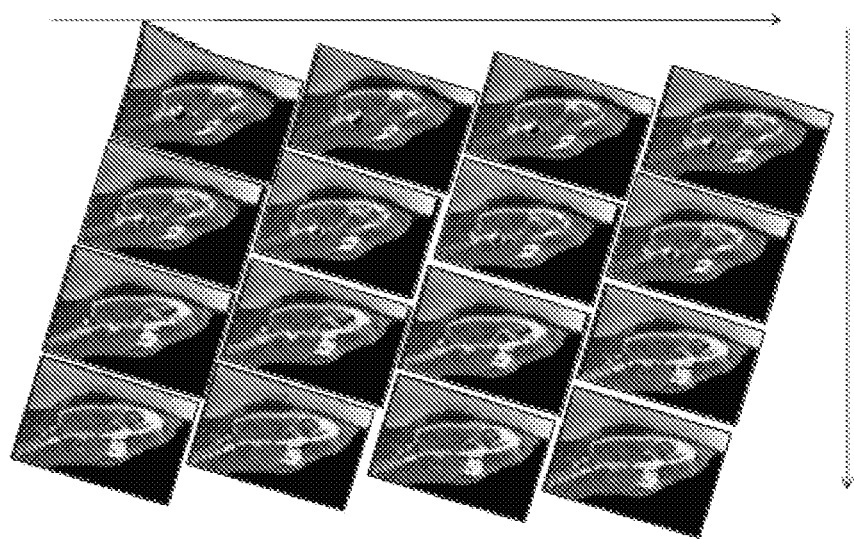

FIG. 33 shows successive sagittal image slices of the rat brain demonstrating radioactive uptake in the olfactory epithelium between 40 and 45 minutes after administration. The radioactive material (red) is clearly seen to be concentrated in the olfactory epithelium.

Figure 34:
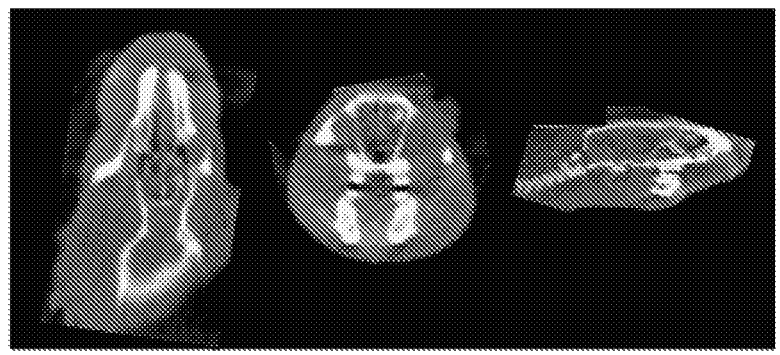

FIG. 34 shows coronal (FIG. 34A), axial (FIG. 34B) and sagittal (FIG. 34C) image slices demonstrating radioactive uptake in the olfactory epithelium between 40 and 45 minutes after administration. Radioactivity is clearly present, limited to the nostril on the right where the drug was administered in FIGS. 34A and 34B.

It should be noted that in the above mentioned examples, the compressed gas is in volumes of about 15 ml and compressed to about 7 bar.

Example 10

Comparison of brain uptake of a compound with low blood-brain barrier (BBB) penetration, when applied to the nasal cavity with the device of the present application to deposition in the respiratory epithelium in the nasal cavity.

Figure 35:
FIGS. 35-36 illustrate the location of deposition of material in the rat after application via a conventional device.

FIG. 35 shows coronal (FIG. 35A), axial (FIG. 35B) and sagittal (FIG. 35C) image slices demonstrating uptake of radioactivity in the animal after administration. Although the nasal cavity is loaded with the radiolabeled drug the drug has deposited in the respiratory epithelium and other nasal cavities, but little has deposited in the olfactory epithelium. This example demonstrates the need to enable deposition at the desired olfactory epithelium when direct nose to brain delivery is desired.

Figure 36:
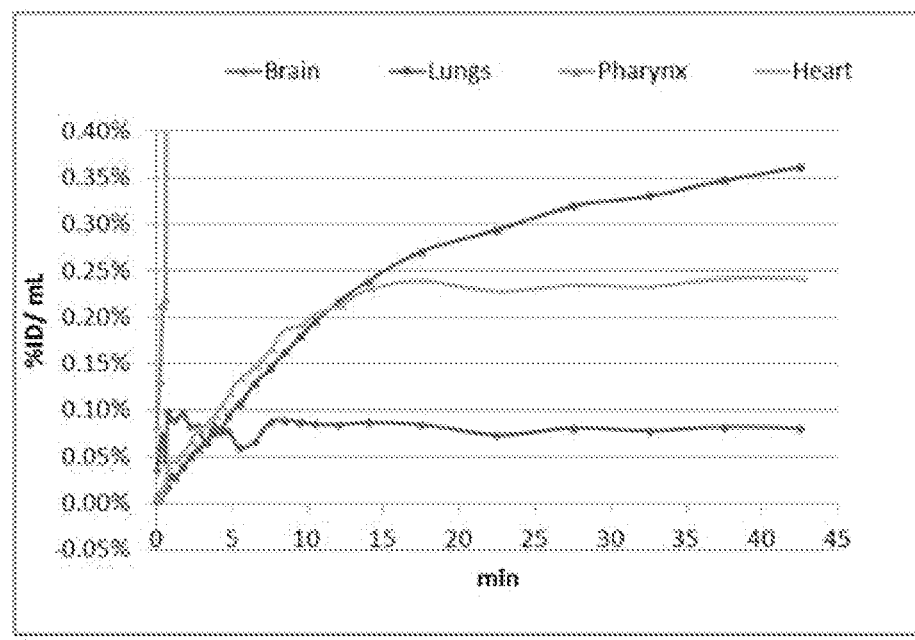

FIG. 36 shows uptake of the radioactivity in the brain (diamonds), lungs (squares), pharynx (triangles) and heart (no symbol). Uptake to the pharynx is greatest; more than 0.4% less than a minute after activation. Uptake to the brain is least, less than 0.1% even 45 minutes after activation, clearly demonstrating that, in this case of no olfactory deposition, there is virtually no brain uptake.

It should be noted that in the above mentioned examples, the compressed gas is in volumes of about 5 ml and compressed to about 4 bar. Thus, the device is used to deposit the drug in the respiratory epithelium.

Thus, it is emphasized that the device as provided by the present invention can tailored to deliver the medication to either the brain, lungs, pharynx or heart and not only to the olfactory epithelium, depending on the parameters that the device is tuned to. With different volumes and pressures, the medicament will reach different locations.

If there are large volumes under high pressure, the same will uptake to the brain; under relatively small volumes and low pressures, the medicament will reach the respiratory epithelium.

Example 11

Comparison of brain uptake of a compound with low blood-brain barrier (BBB) penetration, when applied with the present device versus intravenous (I/V) injection.
I/V Injection FIG. 37A shows fused PET-CT image slices. Locations of uptake are bright. Little uptake to the brain is visible (dark areas, arrows).

FIG. 37B shows uptake of $^{11}$C choline injected intravenously (I/V). Uptake is mostly to the liver (triangles), with about 0.1% ID/ml (diamonds) to the brain.
Present Device FIG. 38A-38B shows uptake of $^{11}$C choline applied with the present device. Uptake is mainly to the olfactory epithelium (FIG. 38A, arrows), with more than 0.5% ID/ml entering the brain (FIG. 38B, diamonds), more than 6 times as much as with the I/V application (FIG. 37B).

Figure 39:
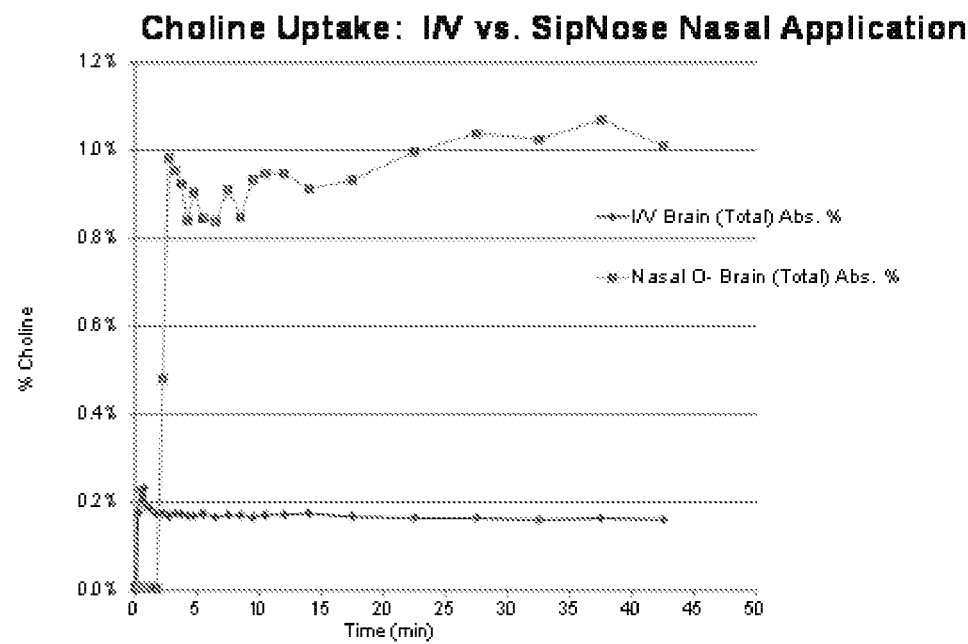
FIG. 39 shows a comparison of uptake to the brain between I/V administration and administration via the present device.

A direct comparison of the uptake via I/V and uptake via the present device is shown in FIG. 39. Uptake to the brain from the I/V injection (diamonds) is less than 0.2% of the administered dose, while uptake to the brain from the present device is more than 1% of the administered dose.

Figure 40:
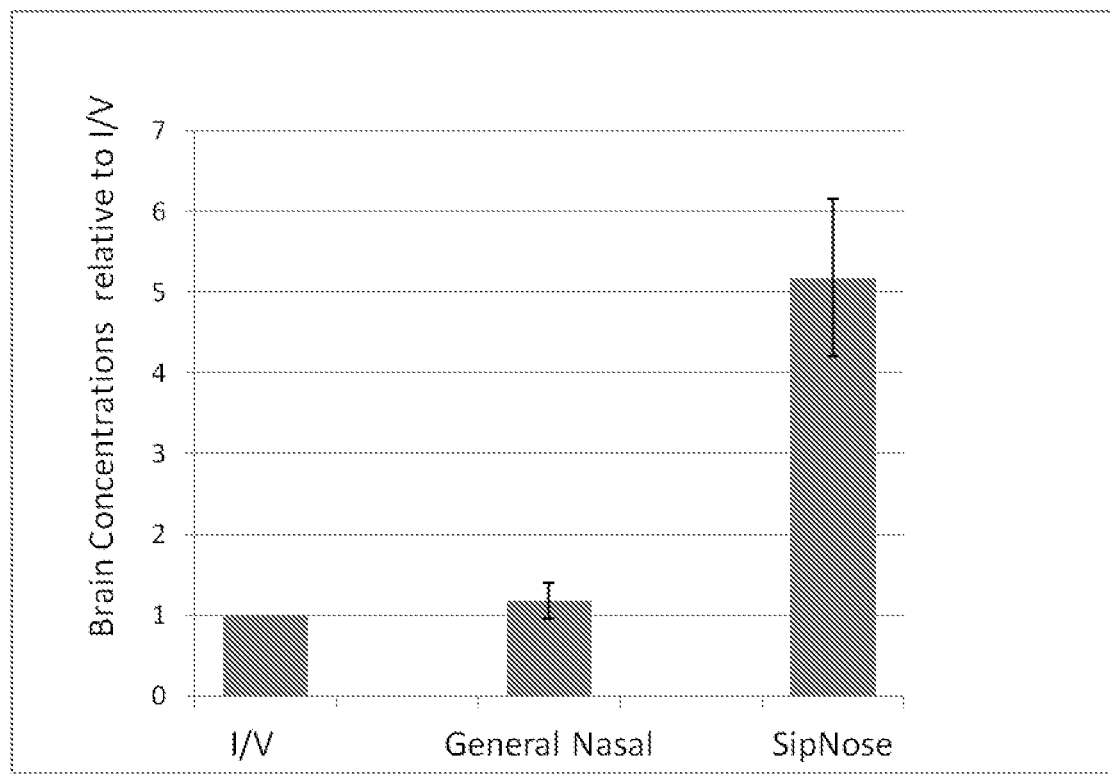
FIG. 40 shows a comparison of uptake to the brain between I/V administration, general nasal administration and administration via the present device.

FIG. 40 shows uptake of choline to the rat brain following administration I/V, via general nasal application, and via the present device (SipNose). The data shown are the average of three trials for the present device, and the average of two trials for each of the I/V administration and the general nasal administration. The bar heights are relative to the brain concentration of $^{11}$C choline after I/V administration. It can be seen that the brain concentration of $^{11}$C choline after general nasal application is the same or slightly more, than that for I/V administration, while the $^{11}$C choline concentration in the brain after administration using the present SipNose device is more than five times as great as the $^{11}$C choline concentration after I/V administration, thereby showing the advantages of the present device over prior art.

Example 12

Figure 41:
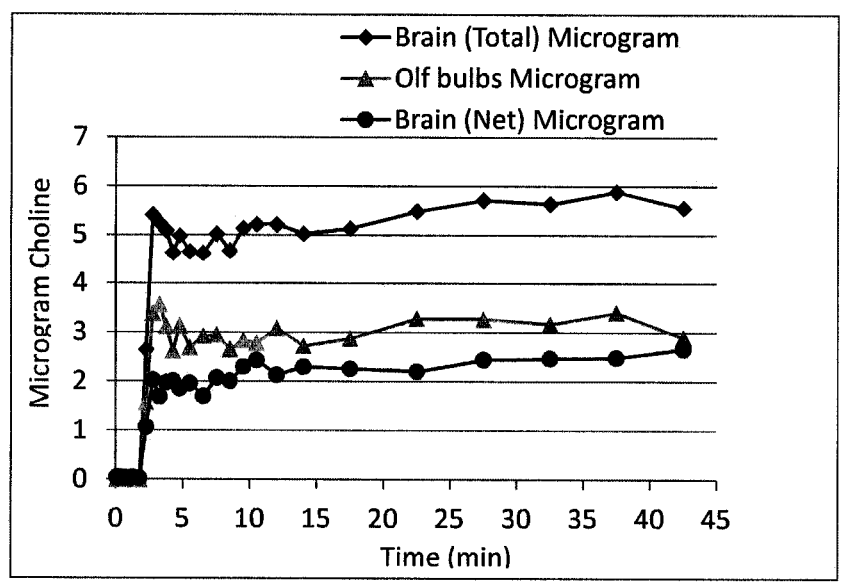
FIG. 41 shows locations of deposition of material in the brain for the present device.

FIG. 41 shows uptake via the present device to different regions of the rat brain. The total uptake to the brain (diamonds) is nearly 6 µg of choline, uptake to the olfactory bulbs (diamonds) is about 3 µg, so that net uptake to non-olfactory brain tissues is about 2.5 µg.

Example 13

F-DOPA Nasal Administration with SipNose Device Versus I/V Administration
Background:

L-DOPA represents the most clinically useful drug in the treatment of Parkinson's (PD) disease and for many years is the gold standard treatment for PD. Unfortunately; the clinical response to oral L-DOPA is variable and unreliable as a result of the inconsistent of its oral absorption and firs path metabolism. Major peripheral side effects are well-known during the treatment with L-DOPA and include among others nausea, vomiting and cardiac irregularity. Decarboxylase inhibitors (as Carbidopa) are co-administered with L-DOPA to decrease its side effects and allow L-DOPA to be transported through the blood brain barrier (BBB) to its target in the brain to exert its effect. With no co-administration of decarboxylase inhibitor, L-DOPA is decarboxylated in the periphery to dopamine, and, as dopamine is unable to cross the BBB, almost no brain uptake of the dopamine is seen and no effect is seen.

Intravenous infusion of L-DOPA (with or without co treatment with decarboxylase inhibitor) was found to dramatically improve the outcome of the L-DOPA treatment, but is inconvenient and impractical as a routine clinical use.

Objectives:

The objective of the experiment was to compare nasal application with SipNose device to a systemic application by IV administration of F-DOPA (that corresponds to the drug L-DOPA) by means of brain absorption (namely the target tissue) and systemic absorption (namely non relevant tissues contamination).

F-Dopa was chosen for this experiment both as a direct model for L-DOPA, which is a known gold standard drug with well known inconsistency and unwanted sides effects that mainly results from its delivery route; the oral route. Also, it was chosen as a model for CNS drugs that do have BBB permeability, but an alternative route of administration that will increase its CNS absorption and will decrease its peripheral tissue uptake will reduce its adverse side effects and will extend its therapeutic window.

Animals:

Rats

Strain: Sprague Dawley

Weight: 200 to 250 gr

Procedure:
  Animals were anesthetized with a Ketamine-Xylazine cocktail.
  Animals were treated according to the 2 groups as below:
    1. Systemic administration of F-DOPA by I/V injection of 1 ml. Administration doses were between 17 and 83 µg, and injected radioactivity dose was around 1000 µCi.
    2. Nasal application of F-DOPA by SipNose device application of 13-20 µl. Administration doses were between 1.2 and 2.8 µg, and injected radioactivity doses were around 26 µCi. All I/V administered animals and part of the Nasal applied animals (as will be indicated) were pre-treated with 10 mg/kg Carbidopa (by IP administration) 30 min prior to L-DOPA administration to eliminate peripheral conversion to dopamine.
      Animals were subjected to Micro-PET-CT. PET scans were done for 45 min following L-DOPA administration by I/V or Nasal route.

Analysis of F-DOPA absorption in the following tissues was tested:
  Brain, Heart, Lungs, liver.

Figure 42:
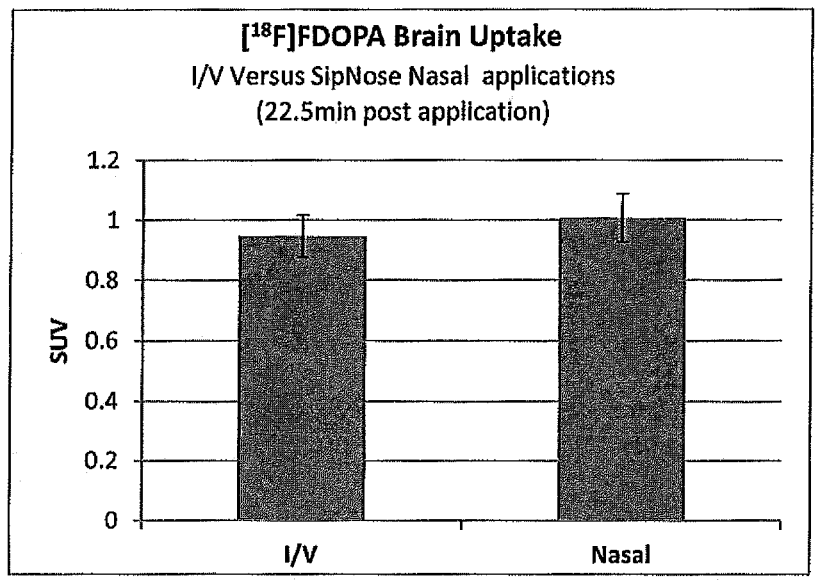
FIG. 42 show a comparison of uptake to the brain via I/V administration and via administration to the nose via the present device.
Figure 43:
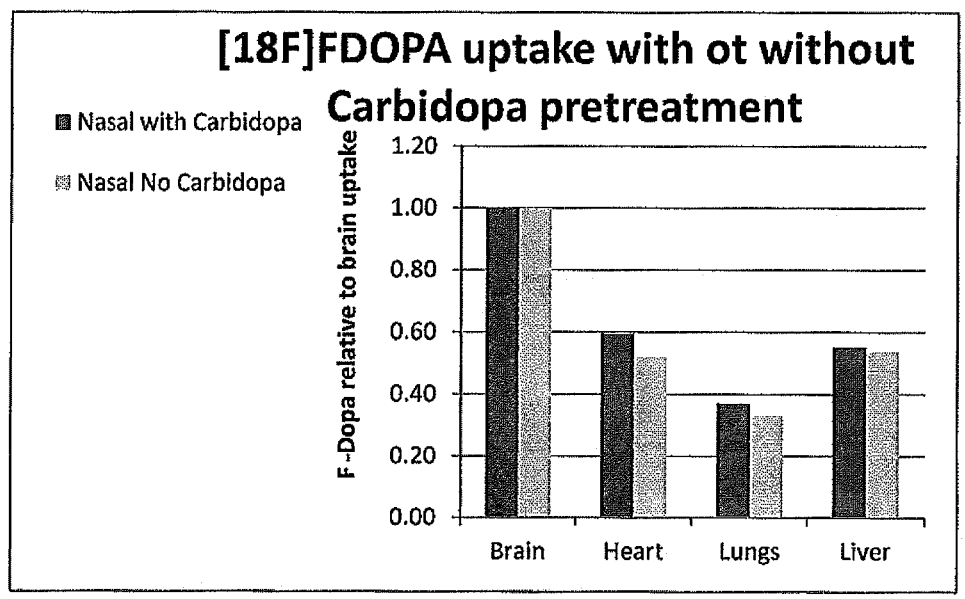
FIG. 43 shows a comparison of uptake of F-DOPA to the brain, heart, lungs and liver via nasal administration with and without Carbidopa pretreatment.

Results:

In reference to FIGS. 42 and 43, comparison of brain uptake between the I/V treated animals and the animals treated with SipNose nasal application 22.5 min post treatment ($t_{50}$ of the PET scan), points out that the brain concentrations are comparable between the nasal and the I/V treated animals.

Comparison of the peripheral uptake of F-Dopa to its brain uptake reveals that
A. Nasal application resulted in lower peripheral concentrations than the brain F-Dopa concentrations.
B. In all peripheral tissues, the percentage of F-Dopa absorption relative to brain absorption is lower in the nasal treated animals than in the I/V treated animals.

Figure 44:
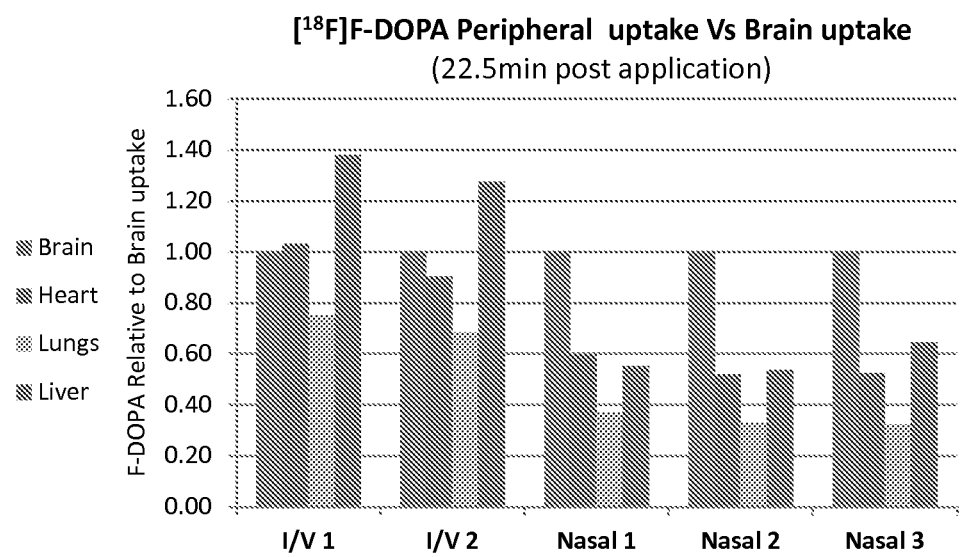
FIGS. 44-45 show a comparison of uptake of F-DOPA to the brain, heart, lungs and liver via I/V administration and via administration to the nose via the present device.
Figure 45:
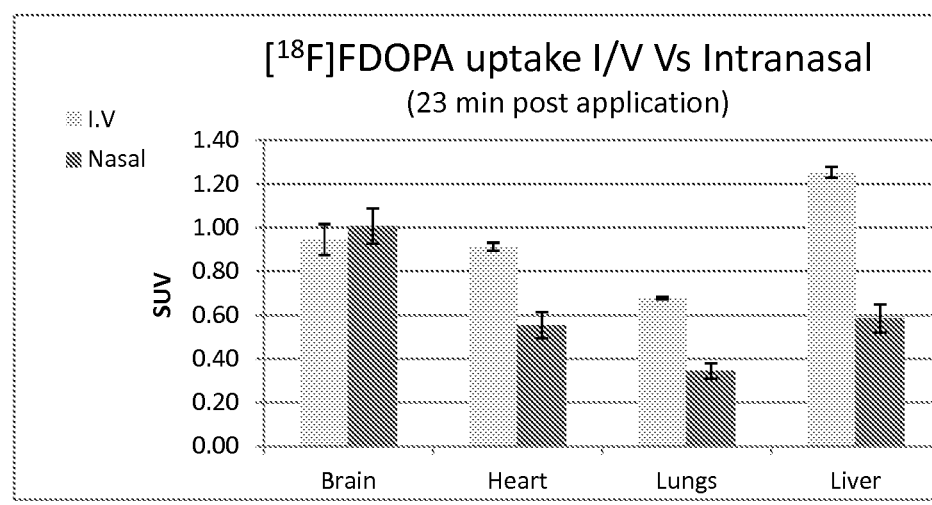

FIG. 44 shows normalized values of F-Dopa in all tissues relative to the brain values in each animal. In the figure, the leftmost bar in each group (blue) shows uptake to the brain, the bar at second left in each group (red) shows uptake to the heart, the bar at second right in each group (green) shows uptake to the lungs, and the bar on the right in each group (purple) shows uptake to the liver, FIG. 45 shows a comparison between uptake to the brain, heart, lungs and liver for the I/V treated group. The comparison shows clear differences between the tissue uptakes for the two groups.

Conclusions:
1. SipNose Nasal delivery device is capable of delivering F-Dopa, and potentially CNS drugs into the brain.
2. Application of F-Dopa (and potentially other CNS drugs) with SipNose device resulted in comparable brain concentrations as I/V administration. I/V administration is known to be efficient and improved when compared to the oral administration of L-DOPA. Thus, as SipNose Nasal delivery is comparable to I/V administration in its brain absorption and show lower systemic distribution, its advantages upon the standard of care oral application is obvious.
3. It is well known that I/V administration of L-DOPA with no pre-treatment with Carbidopa results with very poor brain uptake of the drug. Interestingly enough, the SipNose nasal application in this experiment gave same results whether a pre-treatment with Carbidopa was given or not. This phenomenon although should be further examined, may reflect the fact that the olfactory epithelium rout serves as a bypass rout to the BBB for that drug and potentially other. Although massive decarboxylation my occurred when no Carbidopa was given in the nasal application, brain absorption is comparative to I/V administration that was done following the pre-treatment with Carbidopa. SipNose nasal application which improves olfactory epithelium deposition of aerosol enabled the distribution of the F-Dopa aerosol to allow this interesting occurrence.

Example 14

The device of the present invention can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

Thus, according to one embodiment of the present invention, the use of compressed air to entrain the flowable substance enables delivery the substance to the olfactory epithelium and from there to the brain. In most embodiments, the substance will be a medicament.

Examples of types of drugs and materials to be delivered to or through the nose are, but not limited to: treatments for allergic rhinitis; treatments for osteoporosis; vaccinations and immunizations; sexual dysfunction drugs; treatments for B12 deficiency; smoking cessation; treatment of gynecological problems; treatment of other women's health issues; general anesthetics; local anesthetics; opioid analgesics; agonist-antagonists and antagonists; antitussives; drugs used in the treatment of motor disorders; antiepileptics; drugs used in affective disorders; antipsychotics (neuroleptics); sedative-hypnotics, anxiolytics, and centrally acting muscle relaxants; treatments for anxiety disorders; skeletal muscle relaxants; treatments for Parkinson's disease; treatments for Alzheimer's disease;

Medicaments for treatment of allergic rhinitis include, but are not limited to: steroids, including corticosteroids, Flonase, Patanase, Beconase, antihistamine, Astelin, Otrivin, Livostin, Theramax, Avamys, Luffeel, Sinofresh, Nasonex, Nasocort and Veramyst.

Medicaments for treatment of osteoporosis include, but are not limited to, Miacalcin, Fortical and Stadol.

Medicaments for vaccinations and immunizations include, but are not limited to: Lavin, and influenza vaccines including FluMist.

Medicaments for smoking cessation include, but are not limited to: NasalFent.

Other medicaments which can be delivered include, but are not limited to, calcitonin and parathyroid hormone.

Neurotransmitters and neuromodulators that can be delivered include, but are not limited to: acetylcholine (ACH), anticholinergic drugs, adenosine triphosphate (ATP), aspartate (Asp), beta-amyloid, beta-endorphin, bradykinin, dopamine (DA), L-DOPA, carbidopa, epinephrine, dynorphins, endomorphins, enkephalins, 5-hydroxytryptamine (5-HT), sumatriptan, Imitrex, Migranal, zolmitriptan, Zomig, Gamma-aminobutyric acid (GABA), glutamate (glu), glycine, histamine, leptin, nerve growth factor and other growth factors), norepinephrine, nitric oxide, and Substance P.

General anesthetics which can be delivered include, but are not limited to: alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, Sublimaze, and thiopental.

Local anesthetics which can be delivered include, but are not limited to: benzocaine, bupivacaine, cocaine, lidocaine, prilocaine, procaine, ropivacaine, and tetracaine.

Opioid analgesics, agonist-antagonists, and antitussives which can be delivered include, but are not limited to: agonists, codeine, diphenoxylate, fentanyl, heroin and other opioids, hydrocodone, 1-alpha-acetyl-methadol, levomethadyl acetate, loperamide, meperidine, methadone, morphine, oxycodone, d-propoxyphene, combinations of opioids plus acetaminophen and asa, and tramadol.

Agonist/antagonists and antagonists which can be delivered include, but are not limited to: buprenorphine, butorphanol, nalbuphine, nalorphine, naloxone, naltrexone, nalmefene, pentazocine, codeine, dextromethorphan, and hydrocodone.

Drugs used in the treatment of Parkinson's disease and motor disorders which can be delivered include, but are not limited to: amantadine, apomorphine, baclofen, benzodiazepines, benztropine, bromocriptine, carbidopa, cyclobenzaprine, dantrolene, dopamine, entacapone, haloperidol, L-DOPA, pergolide, pramiprexole, ropinerole, selegiline (L-deprenyl), trihexyphenidyl, rasagiline, Azilect, ladostigil, rotigotine, Neupro, mono amine oxidase inhibitor, and COMT inhibitor.

Antiepileptics which can be delivered include, but are not limited to: acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin and midazolam.

Drugs used in affective disorders which can be delivered include, but are not limited to: antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate and valproic acid.

Antipsychotics (neuroleptics) which can be delivered include, but are not limited to: chlorpromazine (CPZ), clozapine, fluphenazine, haloperidol, olanzapine, quetiapine, risperidone, sertindole, thioridazine, thiothixene and ziprasidone.

Sedative-hypnotics, anxiolytics, and centrally acting muscle relaxants which can be delivered include, but are not limited to: alprazolam, chloral hydrate, diphenhydramine, flumazenil, flurazepam, hydroxyzine, lorazepam, oxazepam, phenobarbital, temazepam, triazolam, zaleplon and zolpidem.

Anxiety disorders and skeletal muscle relaxants which can be delivered include, but are not limited to: alprazolam, chlorazepate, chlordiazepoxide, diazepam, flumazenil (antagonist), lorazepam, and oxazepam.

Other drugs which can be delivered include, but are not limited to: amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, pentobarbital, neuroprotective compounds, neuroprotective peptides, neuroprotective factors, davunetide, anti-schizophrenic drugs, anti depression drugs, Comtan, entacapone, anti ADHD agents, anti ADHD drugs such as Methylphenidate (Ritalin), and anti-autism and anti-autism symptoms drugs.

Treatment of Alzheimer's disease which can be delivered include, but are not limited to: donepezil, galantamine, rivastigmine, tacrine, insulin, insulin detemir, Novolin, Humulin, insulin-like hormone, dopamine agonist and dopamine antagonist.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A two-step mechanism for delivering a flowable substance to the nasal passages of a patient, said two-step mechanism comprising:
   a. a nosepiece configured to be in fluid connection with said nasal passages;
   b. an openable at least one air-tight enclosure, configured to contain a predetermined amount of gas; said predetermined amount of gas compressible to a predetermined amount of pressure;
   c. a charging mechanism, fluidly connected with said at least one air-tight enclosure, characterized by at least two configurations: a retracted configuration and an extended configuration; where, when said charging mechanism is transformed from said extended configuration to said retracted configuration, said charging mechanism is configured to enable delivery of said predetermined amount of gas from at least one first predetermined position in said at least one air-tight enclosure to at least one second predetermined position, said charging mechanism comprising a member of a group consisting of a piston drivable by a lever, an openable air-tight compartment preloaded with said predetermined amount of gas compressed to said predetermined amount of pressure, and any combination thereof; and d. an activation mechanism, configured, upon activation, to release said predetermined amount of gas compressed to said predetermined amount of pressure from said at least one second predetermined position so as to entrain said flowable substance within said predetermined amount of gas and to deliver the same from said at least one second predetermined position to said nasal passages, said activation mechanism comprising a gas release mechanism selected from a group consisting of a valve mechanism, an air flow regulator, a rod configured to pierce the air-tight compartment, a spear configured to pierce the air-tight compartment, a needle configured to pierce the air-tight compartment, a knife configured to pierce the air-tight compartment, and any combination thereof;

wherein said two-step mechanism additionally comprises a mouthpiece connected to said charging mechanism; said mouthpiece connected to said activation mechanism; said activation being by application of suction to said activation mechanism through said mouthpiece.

2. The two-step mechanism of claim 1, wherein said flowable substance is deliverable to a member of a group consisting of respiratory epithelium, olfactory epithelium, brain, lungs, pharynx, heart and any combination thereof through said nasal passages.

3. The two-step mechanism of claim 1, wherein at least one of the following is being held true (a) said predetermined amount of gas is in a volume in a range of about 5-50 ml and said predetermined amount of pressure is in a range of 1.5-10 bar; (b) said two-step mechanism additionally comprises at least one flowable substance container configured to contain said flowable substance, said at least one flowable substance container in fluid connection with said charging mechanism and said nosepiece; (c) said transformation from said extended configuration to said retracted configuration is performed by applying pressure on said charging mechanism; (d) said flowable substance comprises a medicament; (e) when said charging mechanism is transformed from said retracted configuration to said extended configuration, said charging mechanism is configured to transfer said gas into said at least one first predetermined position; and (f) said flowable substance is selected from a group consisting of a liquid, a powder, an aerosol, a slurry, a gel, a suspension and any combination thereof; and any combination thereof.

4. The two-step mechanism of claim 1, wherein said charging additionally comprises a catch, a button, a predetermined sound pattern, a predetermined light pattern, slider, rotatable knob, a latch and any combination thereof.

5. The two-step mechanism of claim 1, wherein at least one of the following is being held true (a) said flowable substance is contained within at least one flowable substance container reversibly emplaceable within said two-step mechanism; (b) said piston sealingly contained in a shaft, said piston flexibly connected to said lever, and said shaft fluidly connected to said openable air-tight enclosure; (c) said shaft comprises said openable air-tight enclosure; and (d) said nosepiece is configured to be removably emplaced in juxtaposition with a nostril, in a manner selected from a group consisting of sealingly emplaced within the nostril, sealingly emplaced against an opening of the nostril, loosely emplaced within the nostril, loosely emplaced against the opening of the nostril; and (f) said charging mechanism comprises a filter, said filter configured to remove from the predetermined amount of gas at least one selected from a group consisting of particulates, bacteria, viruses, moisture, and undesired particles; and any combination thereof.

6. The two-step mechanism of claim 1, wherein at least one of the following is being held true: (i) said at least two configurations of said charging mechanism comprise three configurations, (a) a first configuration being said retracted, (b) a second configuration wherein said charging mechanism is partly extended, at least one flowable substance container is lockable in position and charging is initiatable, and (c) a third configuration being said extended configuration, wherein said at least one flowable substance container is insertable; (ii) said at least one flowable substance container comprises a cartridge, said cartridge comprising a plurality of independently-openable containers, each said independently-openable container comprising a member of a group selected from (a) a single dose of said flowable substance, (b) multiple doses of said flowable substance, (c) different flowable substances, (d) said flowable substance, (e) carrier and (f) any combination thereof; and (iii) said at least one flowable substance container comprises a filter, said filter upstream of said flowable substance, said filter configured to remove from the predetermined amount of gas at least one selected from a group consisting of particulates, bacteria, viruses, moisture, and undesired particles; and any combination thereof.

7. The two-step mechanism of claim 1, wherein at least one of the following is being held true (a) said charging mechanism is configured to open at least one flowable substance container; (b) said charging mechanism is configured to open said at least one flowable substance container during at least some portion of the time during which said charging mechanism is transformed from said extended configuration to said retracted configuration; (c) said charging mechanism is configured to open said at least one flowable substance container at the beginning of the time during which said charging mechanism is transformed from said extended configuration to said retracted configuration; (d) said at least one flowable substance container contains a single dose of said flowable substance; and any combination thereof.

8. The two-step mechanism of claim 1, wherein at least one of the following is being held true (a) at least a portion of said mouthpiece is a member of a group consisting of removable, replaceable and any combination thereof; (b) said mouthpiece comprises an auxiliary air filter, said filter configured to remove from gas passing through said filter at least one selected from a group consisting of particulates, bacteria, viruses, moisture, and undesired particles; (c) said mouthpiece is in fluid connection with said valve mechanism within said two-step mechanism such that suction on said mouthpiece opens said valve mechanism, thereby enabling flow of said predetermined amount of gas compressed to said predetermined pressure through said two-step mechanism; and (d) said activation mechanism comprises a hollow flexible tegument, wherein compressing and releasing said tegument opens said valve mechanism, thereby enabling flow of said predetermined amount of gas through said two-step mechanism; and any combination thereof.

9. The two-step mechanism of claim 1, wherein at least one of the following is being held true (a) at least one flowable substance container comprises a plurality of compartments; (b) said flowable substance comprises a first flowable substance and a second flowable substance; least one of said compartments contains said second flowable substance different from said first flowable substance in at least one other of said compartments; and any combination thereof.

10. The two-step mechanism of claim 1, wherein at least one of the following is being held true (a) said two-step mechanism is configured for a predetermined target population; (b) said predetermined target population is persons of limited physical strength; (c) delivery factors configured to provide optimum delivery of said flowable substance are selected from a group consisting of a length of time over which the delivery occurs, a gas speed in the nostril during delivery of the predetermined amount of gas with said entrained flowable substance, a volume of the predetermined amount of gas entering the nostril, an excess gas pressure in the nostril, a presence of turbulence in the region of the flowable substance, an absence of turbulence in the region of the flowable substance, a presence of turbulence in air channels within the two-step mechanism, an absence of turbulence in air channels within the two-step mechanism, a presence of turbulence in the nostril, an absence of turbulence within the nostril, a presence of turbulence in the nasal passages, an absence of turbulence in the nasal passages, and any combination thereof; (d) parameters selected from a group consisting of a size of the at least one second predetermined position, travel of the piston, frictional force between a piston seal and the at least one air-tight enclosure, diameters of air channels within the two-step mechanism, a diameter of an inlet opening, a diameter of an outlet opening, a mass of the predetermined amount of gas, a volume within which the predetermined amount of gas is contained are configured to ensure optimum delivery of said flowable substance to a predetermined location in said nasal passages; and (e) said predetermined location is selected from a group consisting of lower turbinates, middle turbinates, upper turbinates, ethmoid bone, and any combination thereof; and any combination thereof.

11. The two-step mechanism of claim 1, wherein at least one of the following is being held true (a) said two-step mechanism additionally comprises indicating means configured to provide an indication to the user if said entrainment of said flowable substance within said predetermined amount of gas, and said delivery of said flowable substance entrained within said predetermined amount of gas from said two-step mechanism to said nasal passages has been successful; wherein said indication is visible by means of a change of color, audible by means of a predetermined sound pattern and any combination thereof; (b) said predetermined amount of gas is inert and will not react with said flowable substance; (c) said flowable substance is a medicament selected from a group consisting of saline, an opioid, an agonist, an agonist-antagonist, an antagonist, an antitussive, an antiepileptic, an antipsychotic, a neuroleptic, a sedative-hypnotic, an anxiolytic agent, a centrally-acting muscle relaxant, a steroid, a corticosteroid, fluticasone propionate, olopatadine hydrochloride, Beclomethasone dipropionate, antihistamine, azelastine hydrochloride, xylometazoline hydrochloride, levocabastine hydrochloride, fluticasone furoate, mometasone furoate monohydrate, triamcinolone acetonide, calcitonin-salmon, calcitonin-salmon [rDNA origin], butorphanol tartrate, sofalcone, a combination of Influenza Virus H1N1 Influenza Virus H3N2 Influenza virus Victoria and Influenza virus Yamagata, fentanyl citrate, calcitonin, parathyroid hormone, a neurotransmitter, a neuromodulator, acetylcholine (ACH), an anticholinergic drug, adenosine triphosphate (ATP), aspartate (Asp), beta-amyloid, beta-endorphin, bradykinin, dopamine (DA), L-DOPA, epinephrine, a dynorphin, an endomorphin, an enkephalin, 5-hydroxytryptamine (5-HT), sumatriptan, dihydroergotamine mesylate, zolmitriptan, Gamma-aminobutyric acid (GABA), glutamate (glu), glycine, histamine, leptin, nerve growth factor, norepinephrine, nitric oxide, Substance P, alfentanil, desflurane, enflurane, etomidate, fentanyl, halothane, isoflurane, ketamine, methohexital, methoxyflurane, midazolam, morphine, nitrous oxide ($N_2O$), propofol, sevoflurane, sufentanil, thiopental, benzocaine, bupivacaine, cocaine, lidocaine, prilocaine, procaine, ropivacaine, tetracaine, codeine, diphenoxylate, heroin, hydrocodone, 1-alpha-acetyl-methadol, levomethadyl acetate, loperamide, meperidine, methadone, oxycodone, d-propoxyphene, a combination of at least one opioid with acetaminophen and asa, tramadol, buprenorphine, butorphanol, nalbuphine, nalorphine, naloxone, naltrexone, nalmefene, pentazocine, dextromethorphan, hydrocodone, amantadine, apomorphine, baclofen, a benzodiazepine, benztropine, bromocriptine, cyclobenzaprine, dantrolene, entacapone, haloperidol, pergolide, pramiprexole, ropinirole, trihexyphenidyl, rasagiline, ladostigil, rotigotine, monoamine oxidase inhibitor, Catechol-O-methyl transferase (COMT) inhibitor, acetazolamide, carbamazepine, clonazepam, diazepam, ethosuximide, felbamate, gabapentin, lamotrigine, lorazepam, phenobarbital, phenytoin, primidone, tiagabine, topiramate, valproic acid, vigabatrin, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, lithium carbonate chlorpromazine (CPZ), clozapine, fluphenazine, haloperidol, olanzapine, quetiapine, risperidone, sertindole, thioridazine, thiothixene, ziprasidone, alprazolam, chloral hydrate, diphenhydramine, flumazenil, flurazepam, hydroxyzine, oxazepam, temazepam, triazolam, zaleplon, zolpidem, chlorazepate, chlordiazepoxide, flumazenil, amphetamine, caffeine, ephedrine, methamphetamine, methylphenidate, phentermine, sibutramine, disulfiram, ethanol, methanol, atropine, scopolamine, ketamine, lysergic acid diethylamide (LSD), methylene dioxy-methyl amphetamine (MDMA), mescaline, phencyclidine (PCP), dronabinol, marijuana, Tetrahydrocannabinol (THC), nicotine, pentobarbital, davunetide, methylphenidrate, donepezil, galantamine, rivastigmine, tacrine, insulin, insulin detemir, insulin-like hormone, dopamine agonist, dopamine antagonist and any combination thereof.

12. A method for delivering a flowable substance to the nasal passages of a patient, comprising steps of:

i. providing a two-step mechanism for delivering said flowable substance to the nasal passages, said two-step mechanism comprising:
   1. a nosepiece configured to be in fluid connection with said nasal passages;
   2. an openable at least one air-tight enclosure, configured to contain a predetermined amount of gas; said predetermined amount of gas compressible to a predetermined amount of pressure;
   3. a charging mechanism fluidly connected with said at least one air-tight enclosure, characterized by at least two configurations: a retracted configuration and an extended configuration; where, when said charging mechanism is transformed from said extended configuration to said retracted configuration, said charging mechanism is configured to deliver said predetermined amount of gas from at least one first predetermined position in said at least one air-tight enclosure to at least one second predetermined position; said charging mechanism comprising a member of a group consisting of a piston drivable by a lever, an openable air-tight compartment containing said predetermined amount of gas compressed to said predetermined amount of pressure, any combination thereof; and, 4. an activation mechanism, configured, upon activation, to release said predetermined amount of gas compressed to said predetermined amount of pressure from said at least one second predetermined position so as to entrain said flowable substance within said predetermined amount of gas and to deliver the same from said at least one second predetermined position to said nasal passages, said activation mechanism comprising a gas release mechanism selected from a group consisting of a valve mechanism, an air flow regulator, a rod configured to pierce the air-tight compartment, a spear configured to pierce the air-tight compartment, a needle configured to pierce the air-tight compartment, a knife configured to pierce the air-tight compartment, and any combination thereof;

ii. providing said flowable substance, contained within a container;

iii. fluidly connecting said container with said charging mechanism and said nosepiece;

iv. charging said two-step mechanism by transforming said charging mechanism from said extended configuration to said retracted configuration; thereby delivering said predetermined amount of gas from at least one first predetermined position in said at least one air-tight enclosure to at least one second predetermined position;

v. emplacing said nosepiece in juxtaposition with a nostril in fluid connection with said nasal passages; and vi. activating said two-step mechanism; thereby entraining said flowable substance within said predetermined amount of gas and delivering the same from said at least one second predetermined position to said nasal passages wherein said two-step mechanism additionally comprises a mouthpiece connected to said charging mechanism; said mouthpiece connected to said activation mechanism; said activation being by application of suction to said activation mechanism through said mouthpiece.

13. The method of claim 12, additionally comprising a step of configuring said two-step mechanism to provide said predetermined amount of gas in volumes of about 5-50 ml and compressed to about 1.5-10 bar.

* * * * *